US012691069B2

(12) United States Patent
Shiao et al.

(10) Patent No.: US 12,691,069 B2
(45) Date of Patent: Jul. 28, 2026

(54) SYNTHETIC GLYCOLIPIDS AND GLYCOLIPOSOME COMPOSITIONS : SUITABLE FOR CARGO DELIVERY TO THE CENTRAL NERVOUS SYSTEM

(71) Applicant: KORANEX CAPITAL, Montreal (CA)

(72) Inventors: Tze Chieh Shiao, Montreal (CA); Serge Mignani, Chatenay-Malabry (FR); Rene Roy, Terrebonne (CA)

(73) Assignee: Koranex Capital, Montreal (CA)

( * ) Notice: Subject to any disclaimer, the term of this patent is extended or adjusted under 35 U.S.C. 154(b) by 181 days.

(21) Appl. No.: 18/833,456

(22) PCT Filed: Jul. 26, 2022

(86) PCT No.: PCT/CA2022/051151
§ 371 (c)(1),
(2) Date: Jul. 26, 2024

(87) PCT Pub. No.: WO2023/141693
PCT Pub. Date: Aug. 3, 2023

(65) Prior Publication Data

US 2025/0134812 A1 May 1, 2025

(30) Foreign Application Priority Data

Jan. 26, 2022 (CA) ................................ CA 3146723
Jan. 27, 2022 (WO) ................ PCT/CA2022/050110

(51) Int. Cl.
*A61K 9/1272* (2025.01)
*A61K 38/16* (2006.01)
*C07H 15/18* (2006.01)

(52) U.S. Cl.
CPC ............ *A61K 9/1272* (2013.01); *A61K 38/16* (2013.01); *C07H 15/18* (2013.01)

(58) Field of Classification Search
CPC ...... A61K 9/1272; A61K 38/16; A61K 47/26; C07H 15/18; A61P 25/00
See application file for complete search history.

(56) References Cited

FOREIGN PATENT DOCUMENTS

| | | | |
|---|---|---|---|
| EP | 2255787 | A1 | 12/2010 |
| JP | 2006335652 | A | 12/2006 |
| JP | 2007269768 | A | 10/2007 |

OTHER PUBLICATIONS

The International Search Report and Written Opinion, mailed on Sep. 22, 2022, in the corresponding PCT Appl. No. PCT/CA2022/051151.
Azefu et al., "Facile Synthesis of Stable Lipid Analogues Possessing a Range of Alkyl Groups: Application to Artificial Glycolipids", Bioorg. Med. Chem., Dec. 2002 vol. 10, Issue 12, pp. 4013-4022.
Guggi et al., "Comparative evaluation of cytotoxicity of a glucosamine-TBA conjugate and a chitosan-TBA conjugate," Int. J. Pharm. 278 (2004) 353-360.
Dhaware et al., "Synthesis and Self-assembly of Amphiphilic Homoglycopolypeptide," Langmuir. (2013), 29, 5659-5667.
Diroll et al., "Polycatenar Ligand Control of the Synthesis and Self-Assembly of Colloidal Nanocrystals," J. Am. Chem. Soc. (2016), 138, 10508.
El-Faham et al., "Peptide Coupling Reagents, More than a Letter Soup", Chem. Rev. 2011, 111, 6557-6602.
Goyard et al., "Expedient synthesis of functional single-component glycoliposomes using thiol-yne chemistry," J. Mater. Chem. B. (2016), 4, 4227.
Grabosch et al., "Glyco-SAMs by 'Dual Click': Thiourea-Bridged Glyco-OEG Azides for Cycloaddition on Surfaces," Synthesis, 2010, 0828-0836.

(Continued)

*Primary Examiner* — Jessica Worsham

(57) ABSTRACT

The present disclosure relates to synthetic glycolipids of the formula (I): wherein • A represents $(CH_2)_n$ with n being an integer from 2 to 10 or $CH_2—CH_2—[O—CH_2—CH_2]m$ with m being an integer from 1 to 5; • B represents $NR^3$ or $OCH_2$, with $R^3$ representing H, Me, Et or n-Pr; • "Sugar" represents formulas (A) or (B) where $R^1$ represents OH and $R^2$ represents H, or where $R^1$ represents H and $R^2$ represents OH; • Y represents H when X and Z which are identical represent $O—(CH_2)p-CH_3$, or Z represents H when X and Y which are identical represent $O—(CH_2)_p—CH_3$, with p being an integer from 5 to 18. Glycoliposomes comprising the synthetic glycolipids can be used for the delivery of a therapeutic or diagnostic agent to the central nervous system. Glycoliposomes comprising the synthetic glycolipids can be used to treat a CNS-related disease or disorder.

(I)

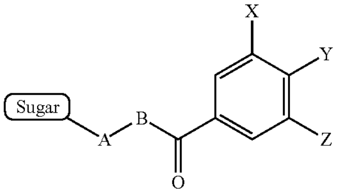

(A)

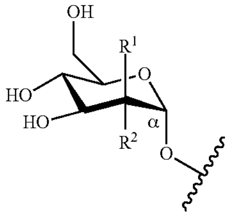

(B)

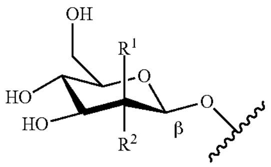

20 Claims, 13 Drawing Sheets

(56) References Cited

OTHER PUBLICATIONS

Lewicky et al., "Mannosylated glycoliposomes for the delivery of a peptide kappa opioid receptor antagonist to the brain," European Journal of Pharmaceutics and Biopharmaceutics, 154; 290-296, 2020.
Lewicky et al., "Improving the Utility of a Dynorphin Peptide Analogue Using Mannosylated Glycoliposomes," Int. J. Mol. Sci., 22, 7996, 1-13, Jul. 27, 2021.
Lewicky et al., Strengthening peptide-based drug activity with novel glyconanoparticle; PLOS ONE | https://doi.org/10.1371/journal.pone.0204472 Sep. 27, 2018.
Mousavifar et al., "Recent Development in the Design of Neoglycoliposomes Bearing Arborescent Architectures," Molecules, 2021, 26, 4281.
Lindhorst et al., "Trivalent-D-mannoside clusters as inhibitors of type-1 fimbriaemediated adhesion of *Escherichia coli*: structural variation and biotinylation," J. Chem. Soc., (2001), 823-831.
Mousavifar et al., "Synthesis & Evaluation of Novel Mannosylated Neoglycolipids for Liposomal Delivery System Applications," Pharmaceutics 2022, 14, 2300.
Percec et al., "Modular Synthesis of Amphiphilic Janus Glycodendrimers and Their Self-Assembly into Glycodendrimersomes and Other Complex Architectures with Bioactivity to Biomedically Relevant Lectins," J. Am. Chem. Soc., (2013), 135, 9055-9077.
Takekawa et al., "Novel Carbohydrate-binding Activity of Pancreatic Trypsins to NLinked Glycans of Glycoproteins", Journal of Biological Chemistry (2006), 281(13), 8528-8538.
Tosin et al., "Synthesis of r-Glucuronic Acid and Amide Derivatives in the Presence of a Participating 2-Acyl Protecting Group," Org. Lett., (2002), 4, 3675-3678.
Tamiaki et al., "Oligomethylene spacer length dependent interaction of synthetic galactolipids incorporated in phospholipid layers with ricin," Colloids Surf. B Biointerfaces, 53, 87-93, 2006.
Adrie W. Bruijnzeel, "Kappa-opioid receptor signalling and brain reward function," Brain Res. Rev. 62, 127-146, Dec. 11, 2009.
Omokawa et al., "Effect of the incorporation of glycolipid analogues into the vesicle membrane composed of nonionic surfactant Span80 on the vesicle characteristics", Maku (2007), 32(5), pp. 302-310. (The English abstract included.).

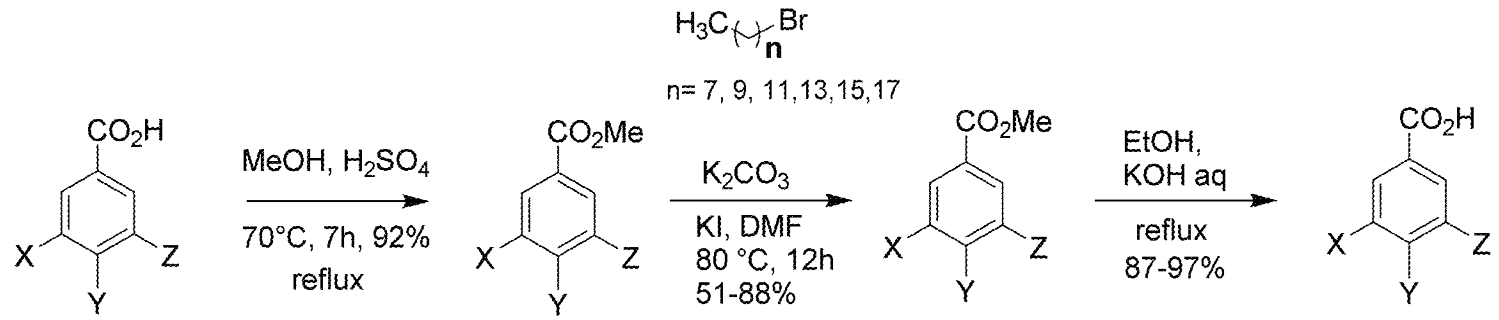

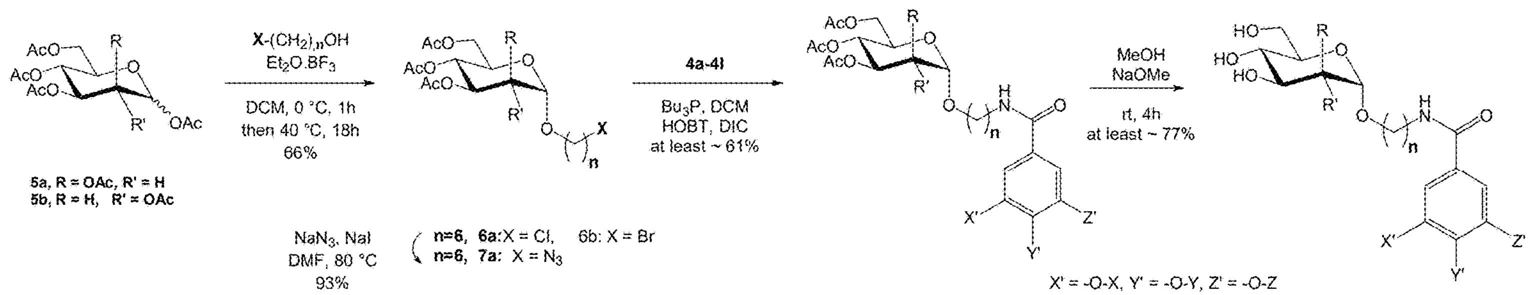

5a, R = OAc, R' = H
5b, R = H, R' = OAc $NaN_3$, NaI
DMF, 80 °C
93%
n=6, 6a:X = Cl, 6b: X = Br
n=6, 7a: X = $N_3$ $NaN_3$, NaI
DMF, 80 °C
93%
n=2, 8a: X = Cl, 8b: X =Br
n=2, 9a: X = $N_3$

X' = -O-X, Y' = -O-Y, Z' = -O-Z n = 6
R = OAc
R' = H

10a: X=Z = $C_8H_{17}$ , Y=H
10b: X=Z = $C_{10}H_{21}$ , Y=H
10c: X=Z = $C_{12}H_{25}$ , Y=H
10d: X=Z = $C_{14}H_{29}$ , Y=H
10e: X=Z = $C_{16}H_{33}$ , Y=H
10f: X=Z = $C_{18}H_{37}$ , Y=H
10g: X= H, Y=Z= $C_8H_{17}$
10h: X= H, Y=Z= $C_{10}H_{21}$
10i: X= H, Y=Z= $C_{12}H_{25}$
10j: X= H, Y=Z= $C_{14}H_{29}$
10k: X= H, Y=Z= $C_{16}H_{33}$
10l: X= H, Y=Z= $C_{18}H_{37}$ n = 2
R = OAc
R' = H

11a: X=Z = $C_8H_{17}$ , Y=H
11b: X=Z = $C_{10}H_{21}$ , Y=H
11c: X=Z = $C_{12}H_{25}$ , Y=H
11d: X=Z = $C_{14}H_{29}$ , Y=H
11e: X=Z = $C_{16}H_{33}$ , Y=H
11f: X=Z = $C_{18}H_{37}$ , Y=H
11g: X= H, Y=Z= $C_8H_{17}$
11h: X= H, Y=Z= $C_{10}H_{21}$
11i: X= H, Y=Z= $C_{12}H_{25}$
11j: X= H, Y=Z= $C_{14}H_{29}$
11k: X= H, Y=Z= $C_{16}H_{33}$
11l: X= H, Y=Z= $C_{18}H_{37}$ n = 6
R = H
R' = OAc

10'a: X=Z = $C_8H_{17}$ , Y=H
10'b: X=Z = $C_{10}H_{21}$ , Y=H
10'c: X=Z = $C_{12}H_{25}$ , Y=H
10d: X=Z = $C_{14}H_{29}$ , Y=H
10'e: X=Z = $C_{16}H_{33}$ , Y=H
10'f: X=Z = $C_{18}H_{37}$ , Y=H
10g: X= H, Y=Z= $C_8H_{17}$
10'h: X= H, Y=Z= $C_{10}H_{21}$
10'i: X= H, Y=Z= $C_{12}H_{25}$
10'j: X= H, Y=Z= $C_{14}H_{29}$
10'k: X= H, Y=Z= $C_{16}H_{33}$
10'l: X= H, Y=Z= $C_{18}H_{37}$ n = 2
R = H
R' = OAc

Mannose, 5a, 6a, 7a 1a, 2a, 3d, 4d 7a, 4d, 10d, 12d

Reagents and conditions: (i) $Ac_2O$, pyridine (rt, 12h); (ii) $Cl(CH_2)_6OH$, $Et_2O.BF_3$, DCM (0 °C, 1h then 40 °C, 18h); (iii) $NaN_3$, NaI, DMF (80 °C, 24h then rt, 16h); (iv) MeOH, conc. $H_2SO_4$ (70 °C, 7h); (v) $CH_3(CH_2)_{13}Br$, $K_2CO_3$, KI, DMF (80 °C, 12h); (vi) EtOH, KOH, $H_2O$ (reflux, 4h); (vii) $Bu_3P$, DCM, HOBT, DIC (0 °C, 2h then rt, 67h); (viii) MeONa, MeOH, pH 8.0 (rt, 4h).

SYNTHETIC GLYCOLIPIDS AND GLYCOLIPOSOME COMPOSITIONS : SUITABLE FOR CARGO DELIVERY TO THE CENTRAL NERVOUS SYSTEM

CROSS-REFERENCE TO RELATED APPLICATIONS

This application is a National Stage Application of PCT/CA2022/051151 filed Jul. 26, 2022, which claims priority from Canadian Patent Application No. 3,146,723 filed on Jan. 26, 2022, and PCT Application No. PCT/CA2022/050110, filed on Jan. 27, 2022. The priority of said Canadian and PCT Applications are claimed. Each of the prior mentioned applications is hereby incorporated by reference herein in its entirety.

FIELD

The present invention relates to synthetic glycolipids, a process for the synthesis thereof, and glycoliposomal delivery systems formed from these synthetic glycolipids. The glycoliposomes are useful for delivering a therapeutic or diagnostic agent to the central nervous system.

BACKGROUND

In recent years, various nanotechnology platforms in the area of medical biology, including both diagnostics and therapy, have gained remarkable attention. Nanomedicine is an umbrella term and is defined as a specific branch of medicine that uses nanotechnology techniques for the prevention and treatment of disease through the development of biocompatible nanoscale materials with overall dimensions in the nanoscale for diagnosis, imaging, drug delivery, sensing or actuation purposes in a living organism. Nanodelivery platforms can help to improve solubility and bioavailability, as well to reduce off-target effects for the delivery of small molecules, genes and vaccines/drugs. Several approved formulations were described encompassing liposomal (e.g. Abelect®, lipid amphotericin B formulation), PEGylated liposomes (e.g. Doxil®, PEGylated liposomal doxorubicin), nanocrystal (e.g. Emend®), nanoparticles (e.g. Abraxane®, paclitaxel albumin-bound particles), dendrimer (Vivagel). Doxil® was the first FDA-approved nanodrug in 1995, and recently a generic named Lipodox™ (Sun Pharmaceutical Industries LTD), has been FDA-approved. Treatment of CNS diseases, such as Alzheimer's disease (AD), Parkinson's disease (PD), Huntington's disease (HD), head trauma, brain tumor, and epilepsy, requires efficient delivery across the blood brain barrier (BBB). Various strategies have been developed to overcome the barriers to CNS delivery including 1) intracranial delivery, 2) transient BBB disruption; 3) chemical structure modification of molecules; 4) co-administration of P-glycoprotein inhibitors; 5) intranasal delivery; and 6) nanotechnology for CNS delivery including liposomes, nanoemulsions, nanoparticles, micelles, nanocrystals, and dendrimers. Nevertheless, delivery systems capable of efficient and safe delivery across the BBB are limited and challenging to produce. There is therefore a growing need for novel CNS delivery systems for the treatment of CNS diseases and disorders.

SUMMARY

According to one aspect, described herein is a synthetic glycolipid having the formula (I)

(I)

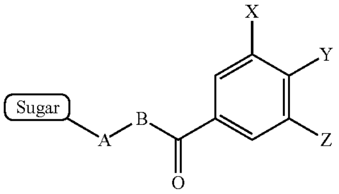

wherein

A represents $(CH_2)_n$ with n being an integer from 2 to 10 or $CH_2—CH_2—[O—CH_2—CH_2]_m$ with m being an integer from 1 to 5;

B represents $NR^3$ or $OCH_2$, with $R^3$ representing H, Me, Et or n-Pr;

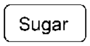 represents

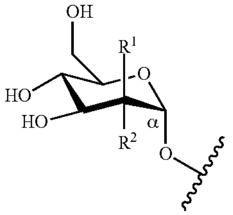

or

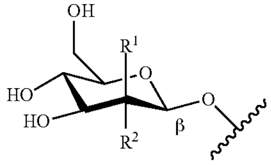

where $R^1$ represents OH and $R^2$ represents H, or where $R^1$ represents H and $R^2$ represents OH;

Y represents H when X and Z which are identical represent $O—(CH_2)_p—CH_3$, or X represents H when Y and Z which are identical represent $O—(CH_2)_p—CH_3$, with p being an integer from 5 to 18;

with the proviso that the synthetic glycolipid of formula (I) is different than the compound of formula (II) or (III)

(II)

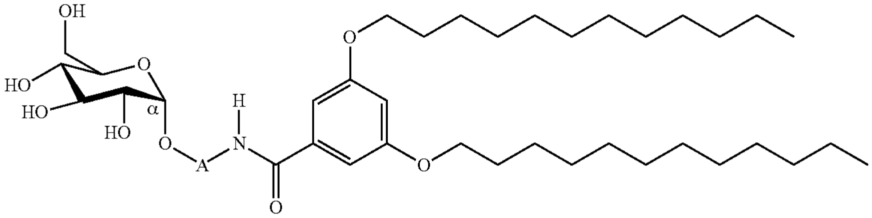

-continued (III)

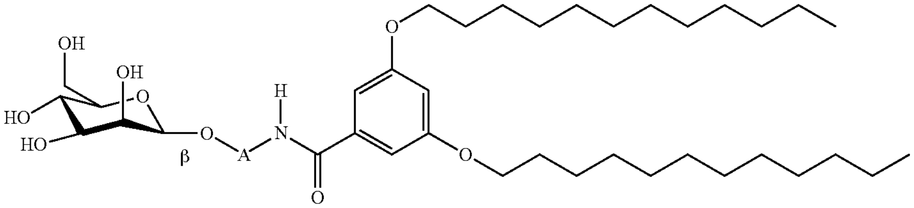

where $A=(CH_2)_{n'}$ with n'=2, 6, 10;

and with the proviso that the synthetic glycolipid of formula (I) is different than the compound of formula (IV)

(IV)

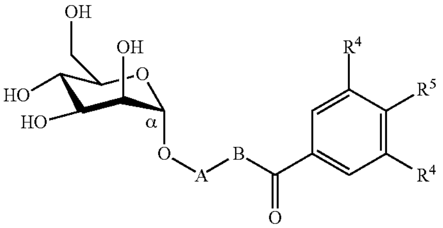

where A represents $CH_2—CH_2$;

and

B represents NH, $R^4$ is H and $R^5$ is $OC_{18}H_{37}$; or

B represents NH, $R^5$ is H and $R^4$ are identical $OC_xH_y$ groups with x is 12, 14, 16, or 18 and y is 2x+1; or B represents NH, $R^4$ and $R^5$ are identical and represent $OC_{18}H_{37}$; or B represents NMe, $R^4$ is $OC_{18}H_{37}$ and $R^5$ is H.

In some embodiments, the synthetic glycolipid has the formula (I)

(I)

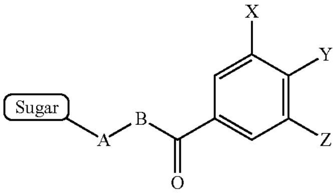

wherein

A represents $(CH_2)_n$ with n being an integer from 2 to 10 or $CH_2—CH_2—[O—CH_2—CH_2]_m$ with m being 2 or 3;

B represents $NR^3$ with $R^3$ representing H, Me, Et or n-Pr;

Sugar represents

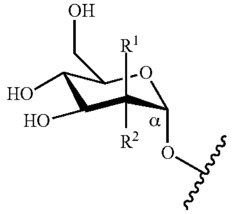

or

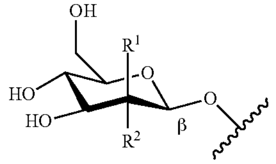

where $R^1$ represents OH and $R^2$ represents H, or where $R^1$ represents H and $R^2$ represents OH;

Y represents H when X and Z which are identical represent $O—(CH_2)_p—CH_3$, or X represents H when Y and Z which are identical represent $O—(CH_2)_p—CH_3$, with p being an integer from 5 to 18;

with the proviso that the synthetic glycolipid of formula (I) is different than the compound of formula (II) or (III)

(II)

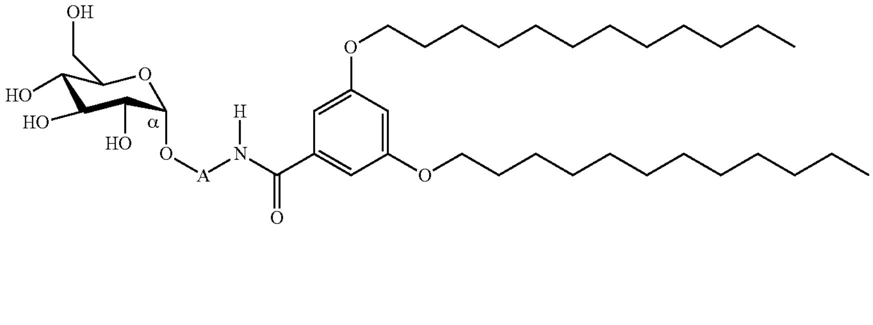

-continued (III)

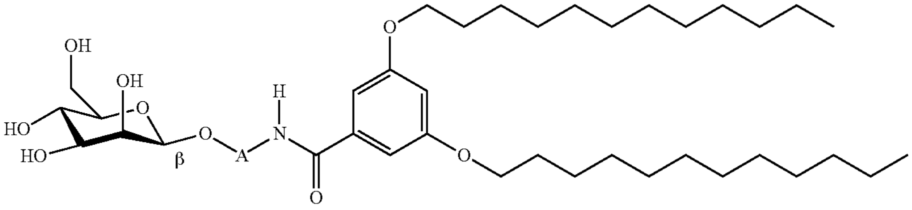

where A=$(CH_2)_{n'}$ with n'=2, 6, 10;
with the proviso that the synthetic glycolipid of formula (I) is different than the following compound

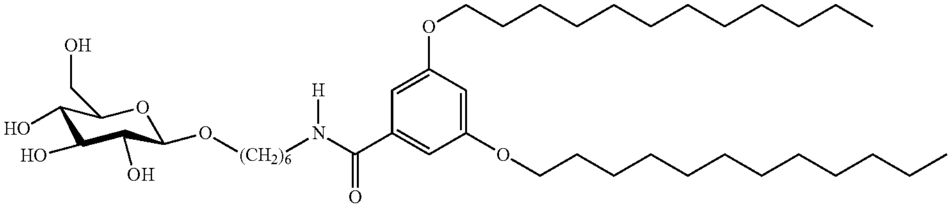;

and with the proviso that the synthetic glycolipid of formula (I) is different than the compound of formula (IV)

(IV)

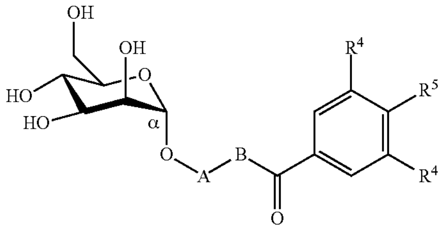

where A represents $CH_2$—$CH_2$;
and
B represents NH, R is H and $R^4$ are identical $OC_xH_y$ groups with x is 12, 14, 16, or 18 and y is 2x+1; or
B represents NMe, $R^4$ is $OC_{18}H_{37}$ and R is H;
or
where A represents —$(CH_2)_6$—, B represents NH, $R^5$ is H and $R^4$ are both $O(CH_2)_{12}H$.

In some embodiments, the synthetic glycolipid has the formula (I) described above, with the further proviso that the synthetic glycolipid of formula (I) is different than the compound of formula (IV)

(IV)

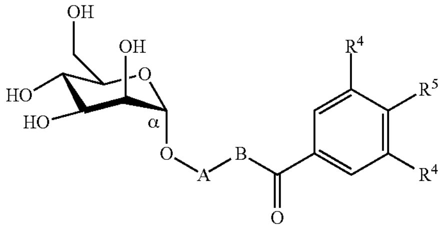

where A represents $(CH_2)_n$ with n being 2, 6 or 10; B represents NH, $R^4$ is $OC_{14}H_{29}$ and $R^5$ is H.

In some embodiments, the synthetic glycolipid can have the formula (Ia)

(Ia)

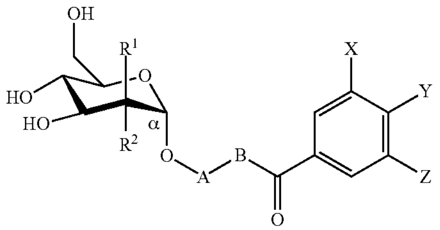

wherein
A represents $(CH_2)_n$ with n=6;
B represents NH;
$R^1$ represents OH and $R^2$ represents H;
Y represents H, and X and Z which are identical represent O—$(CH_2)_p$—$CH_3$, with p=13.

According to another aspect, described herein is a glycoliposome comprising a plurality of co-assembled synthetic glycolipids as defined herein.

According to yet another aspect, described herein is the use of the glycoliposome as defined herein, for the delivery of a therapeutic or diagnostic agent to the central nervous system.

According to yet another aspect, described herein is a glycoliposome for use in delivering a therapeutic or diagnostic agent to the central nervous system, wherein the glycoliposome comprises a plurality of co-assembled synthetic glycolipids and each synthetic glycolipid has the following formula (I)

(I)

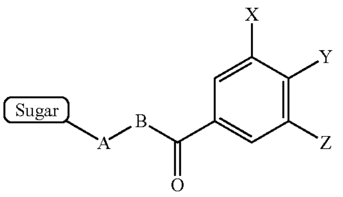

wherein

A represents $(CH_2)_n$ with n being an integer from 2 to 10 or $CH_2—CH_2—[O—CH_2—CH_2]_m$ with m being an integer from 1 to 5;

B represents $NR^3$ or $OCH_2$, with $R^3$ representing H, Me, Et or n-Pr;

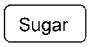 represents

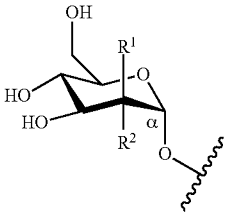

or

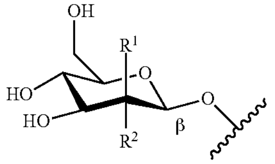

where $R^1$ represents OH and $R^2$ represents H, or where $R^1$ represents H and $R^2$ represents OH;

Y represents H when X and Z which are identical represent $O—(CH_2)_p—CH_3$, or X represents H when Y and Z which are identical represent $O—(CH_2)_p—CH_3$, with p being an integer from 5 to 18.

According to yet another aspect, described herein is a method for delivering a therapeutic or diagnostic agent to the central nervous system of a patient in need of the therapeutic or diagnostic agent, comprising:

entrapping the therapeutic or diagnostic agent into a glycoliposome comprising a plurality of co-assembled synthetic glycolipids; and administering the glycoliposome with the entrapped therapeutic or diagnostic agent to the patient;

wherein each synthetic glycolipid has the following formula (I)

(I)

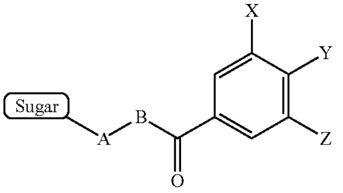

wherein

A represents $(CH_2)_n$ with n being an integer from 2 to 10 or $CH_2—CH_2—[O—CH_2—CH_2]_m$ with m being an integer from 1 to 5;

B represents $NR^3$ or $OCH_2$, with $R^3$ representing H, Me, Et or n-Pr;

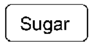 represents

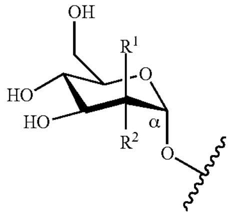

or

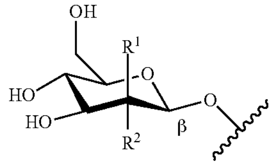

where $R^1$ represents OH and $R^2$ represents H, or where $R^1$ represents H and $R^2$ represents OH;

Y represents H when X and Z which are identical represent $O—(CH_2)_p—CH_3$, or X represents H when Y and Z which are identical represent $O—(CH_2)_p—CH_3$, with p being an integer from 5 to 18.

According to yet another aspect, described herein is the use of the glycoliposome as defined herein, for the treatment of a CNS-related disease or disorder.

According to another aspect, described herein is the use of the glycoliposome as defined herein, for the manufacture of a medicament for the treatment of a CNS-related disease or disorder.

According to another aspect, described herein is a method for treating a CNS-related disease or disorder in a patient in need thereof, said method comprising administering the glycoliposome as defined herein to the patient.

In some embodiments, the CNS-related disease or disorder is a neurodegenerative disease or disorder, depression, post-traumatic stress disorder, stress, anxiety, addiction, drug abuse or addiction, pain, eating disorder, psychiatric or mood disorders, psychosis, or schizophrenia.

According to another aspect, described herein is a process for preparing a synthetic glycolipid having the following formula (I)

(I)

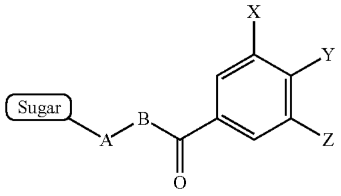

wherein

A represents $(CH_2)_n$ with n being an integer from 2 to 10 or $CH_2—CH_2—[O—CH_2—CH_2]_m$ with m being an integer from 1 to 5;

B represents NH;

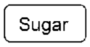 represents

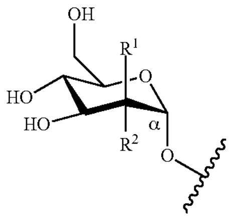

or

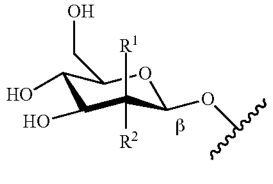

where $R^1$ represents OH and $R^2$ represents H, or where $R^1$ represents H and $R^2$ represents OH;

Y represents H when X and Z which are identical represent O—$(CH_2)_p$—$CH_3$, or X represents H when Y and Z which are identical represent O—$(CH_2)_p$—$CH_3$, with p being an integer from 5 to 18;

the process comprising:

reducing a compound of formula (V)

(V)

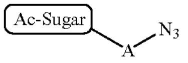

where 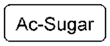 represents

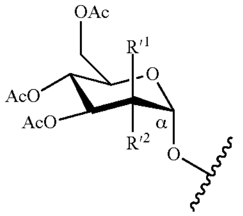

or

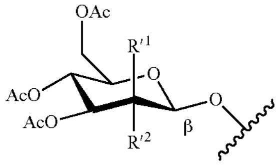

with $R'^1$ represents OAc and $R'^2$ represents H, or where $R'^1$ represents H and $R'^2$ represents OAc;

into the corresponding amine; and coupling the amine with a compound of formula (VI)

(VI)

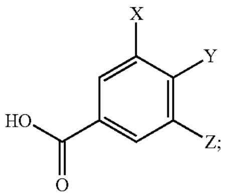

thereby forming the compound of formula ($I_{Ac}$)

($I_{Ac}$)

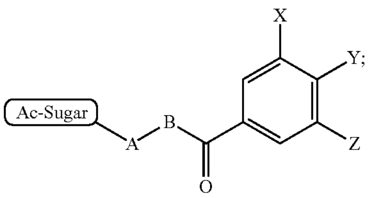

and converting the compound of formula ($I_{Ac}$) into the synthetic glycolipid of formula (I).

BRIEF DESCRIPTION OF THE DRAWINGS

In the appended drawings:

FIG. 4 shows the synthesis scheme of benzoic acid derivatives 4a-4l.

FIG. 5 shows the synthesis scheme of synthetic glycolipids 12a-13l and 12'a-13'l.

or with (bottom panels) Nile Red. Images were obtained using an inverted Olympus IX73 microscope and are merged with phase contrast and TRITC, 400× magnification. Cells were exposed at 540 nm for 2 s. Scale bar, 20 μm.

Figure 10:
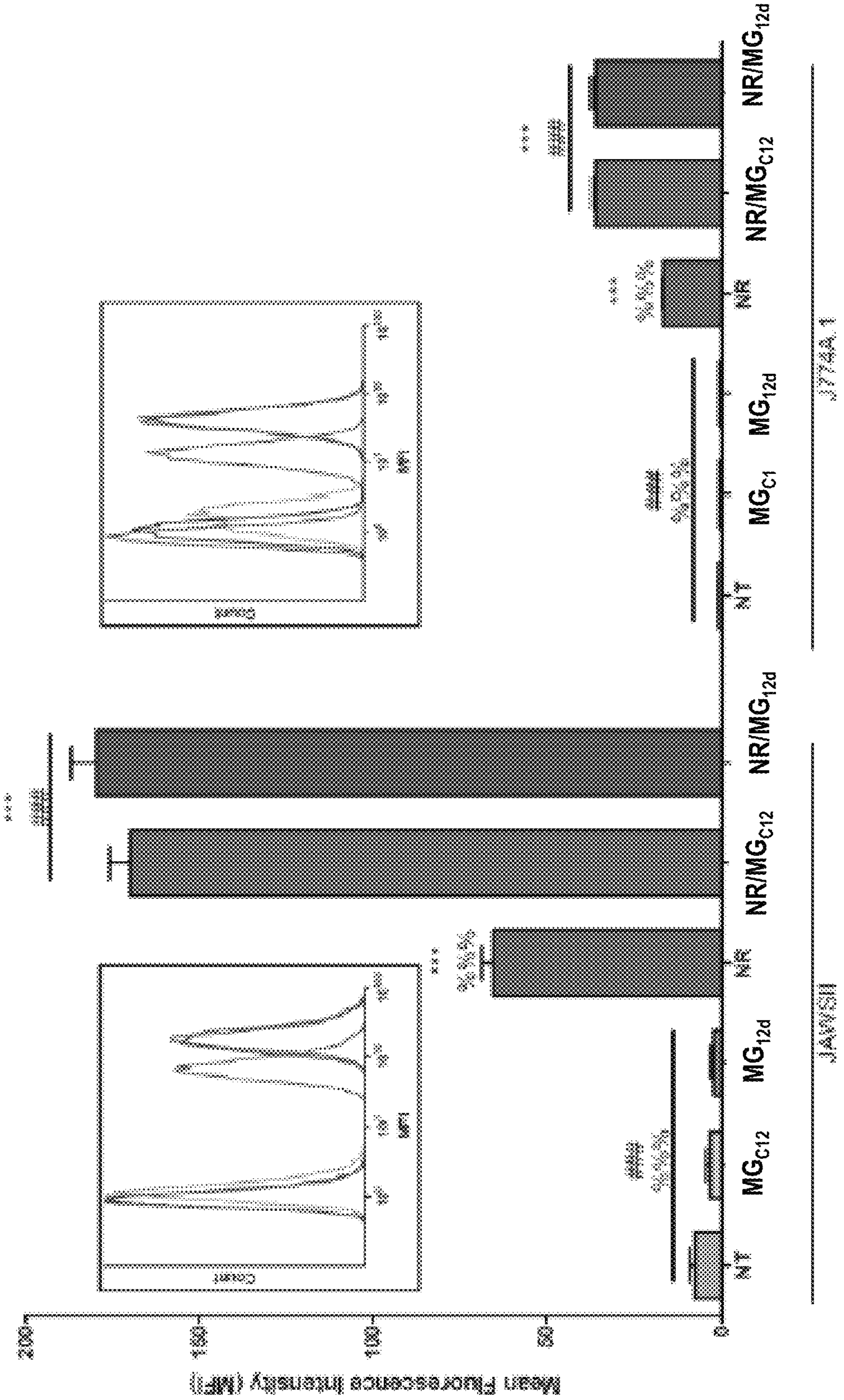

FIG. 10 shows the Nile Red uptake by JAWSII and J774A.1 cells with $MG_{C12}$ or $MG_{12d}$. JAWSII and J774A.1 cells were seeded at $3\times10^5$ cells in 300 μL in a 96 multi-well plate and were left untreated (NT) or were treated with 10 μg/mL of empty $MG_{C12}$ or $MG_{12d}$, 1 μg/mL of Nile Red (NR), or 1 μg/mL of Nile Red encapsulated in 10 μg/mL of liposome ($MG_{C12}$ or $MG_{12d}$). Cells were collected after 1 hour at 37° C., washed once with 300 μL of PBS, and suspended in 300 μL of PBS. A. Nile Red fluorescence was measured by flow cytometry and 104 events were measured. Histogram representative of a triplicate from one experiment is represented for each cell line (inset). The average mean fluorescence intensity is shown for each treatment where ***p<0.001 as compared to NT, $MG_{C12}$ or $MG_{12d}$, ###p<0.001 as compared to NR alone, and %%% p<0.001 as compared to $MG_{C12}$ or $MG_{12d}$. Data are shown as the average SEM of a triplicate from one experiment.

Figure 11:
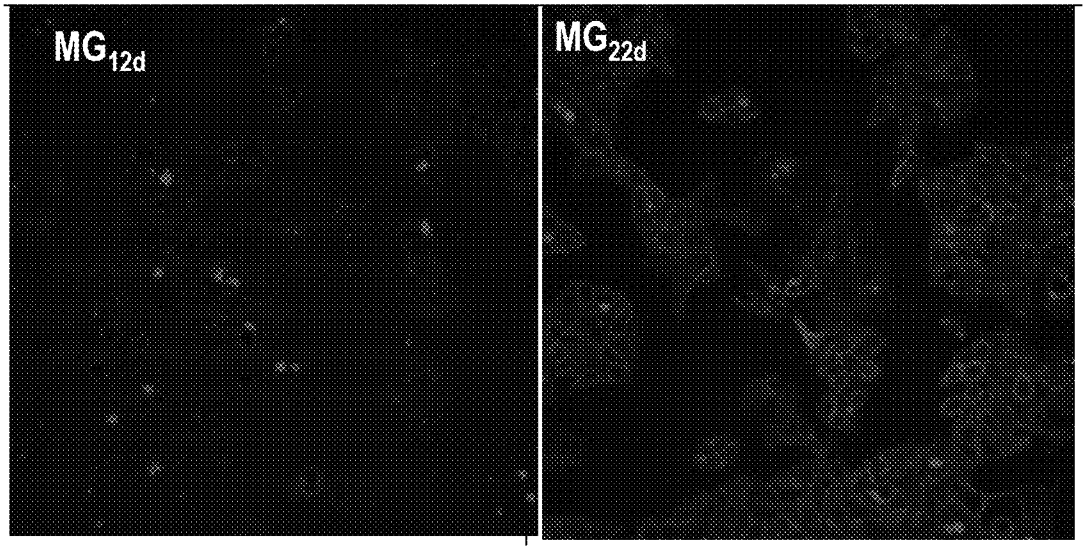

FIG. 11 shows Nile red uptake by HeLa cells with $MG_{12d}$ (left) and $MG_{22}a$ (right) (no staining with Nile Red alone or pegylated liposomes deprived of mannose (not shown).

Figure 12:
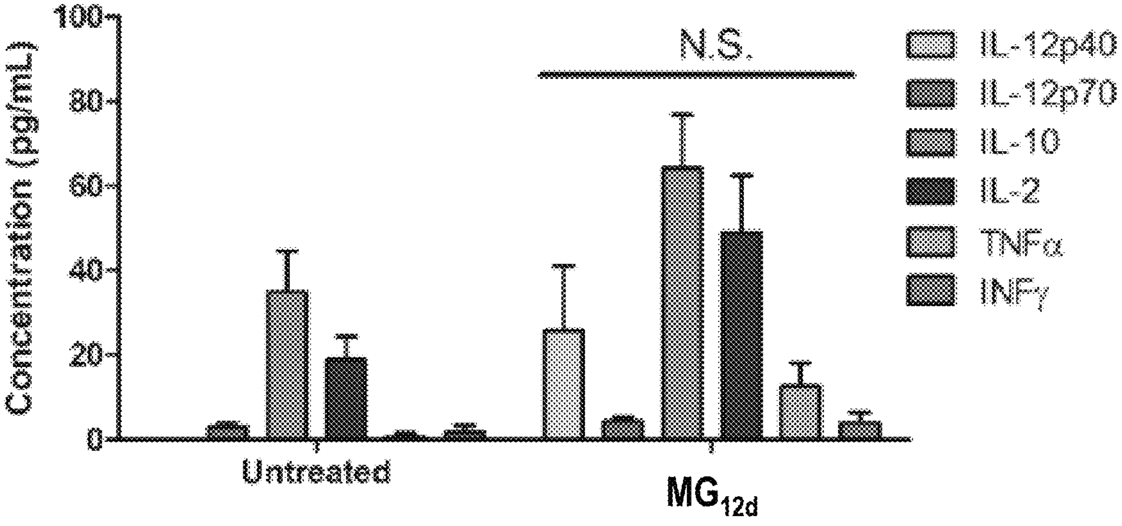

FIG. 12 shows the immunogenicity assessment of $MG_{12d}$. Immune responses in PBMCs (isolated from 3 healthy volunteers) were measured. PBMCs were seeded at $10^6$ cells/mL and left untreated or treated with glycoliposomes formed from $MG_{12d}$ (10 μg/mL). Cells were incubated for 48 hours and supernatants were analysed for the production of cytokines by ELISA. Statistical analysis in the form of an unpaired T-test was performed using GraphPad™ Prism and no significance (N.S.) was observed between the untreated and $MG_{12d}$ liposome-based treated groups for each respective cytokine.

DETAILED DESCRIPTION

Definitions

As used herein the singular forms "a", "an", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The term "about" or "approximately" or "around" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 10%, more preferably up to 5%, and more preferably still up to 1% of a given value. Where particular values are described in the application and claims, unless otherwise stated the term "about" meaning within an acceptable error range for the particular value should be assumed.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used herein, the terms "disease" and "disorder" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The term "subject" or "patient" as used herein refers to an animal, preferably a mammal, and most preferably a human who is the object of treatment, observation, or experiment.

The term "synthetic glycolipid" as used herein refers to amphiphilic glycolipidic molecules that can assemble to form a glycoliposome as defined herein. The synthetic glycolipids include a hydrophilic carbohydrate moiety and a hydrophobic lipidic moiety. The carbohydrate moiety is linked to the hydrophobic lipidic moiety through an alkyl or alkoxyl chain bearing an amide (—NHCO—), N(alkylamine)amide (—Nalkyl-CO—), or $—OCH_2—$ function, as will be detailed below.

The term "glycoliposome" as used herein refers to a vesicle or liposome formed of amphiphilic glycolipidic molecules, also referred to as "synthetic glycolipids" in the present disclosure. The glycoliposome is generally a spherical vesicle composed of a bilayer of assembled synthetic glycolipids enclosing a central cavity, which can be filled with water and/or a water miscible solvent. The bilayer of assembled synthetic glycolipids can be seen as an envelope surrounding the central cavity of the vesicle, the envelope having an external surface and an internal surface. The carbohydrate moieties of the synthetic glycolipids are present at the external and internal surfaces of the envelope and the lipidic moieties of synthetic glycolipids are present in between the external and internal surfaces. The cavity of the glycoliposome can be used to transport an agent, such as a therapeutic or diagnostic agent, to a site where the agent is needed. In some embodiments, the glycoliposome of the present disclosure can be used to transport a therapeutic or diagnostic agent to the central nervous system. In some aspects, the glycoliposome may have a diameter ranging from about 10 nm to 1000 nm. For certain applications, the glycoliposome may have a diameter ranging from about 10 nm to 600 nm.

Synthetic Glycolipids

In some aspects, the present description relates to amphiphilic molecules comprising carbohydrates (e.g., mannose or glucose) covalently linked to benzoic acid derivatives bearing hydrophobic alkoxy groups as tails, through an alkyl or alkoxyl chain. In some embodiments, the carbohydrates can be linked to the alkyl or alkoxyl chain under their alpha stereochemistry or their beta stereochemistry. The connection between the alkyl or alkoxyl chain attached to the carbohydrates and the benzoic acid can be through an amide (—NHCO—), N(alkylamine)amide (—Nalkyl-CO—), or $—OCH_2—$ function.

In some embodiments, the synthetic glycolipid can have the formula (I)

(I)

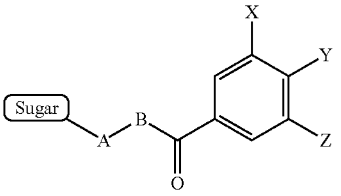

wherein

A represents $(CH_2)_n$ with n being an integer from 2 to 10 or $CH_2$—$CH_2$—[O—$CH_2$—$CH_2$]$_m$ with m being an integer from 1 to 5;

B represents $NR^3$ or $OCH_2$, preferably $NR^3$, with $R^3$ representing H, Me, Et or n-Pr;

Sugar represents

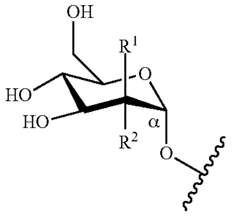

or

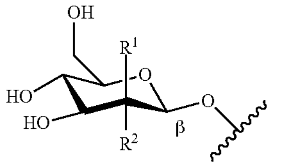

where $R^1$ represents OH and $R^2$ represents H, or where $R^1$ represents H and $R^2$ represents OH;

Y represents H when X and Z which are identical represent O—$(CH_2)_p$—$CH_3$, or X represents H when Y and Z which are identical represent O—$(CH_2)_p$—$CH_3$, with p being an integer from 5 to 18.

In some embodiments, the synthetic glycolipid of formula (I) is different than the compound of formula (II) or (III)

(II)

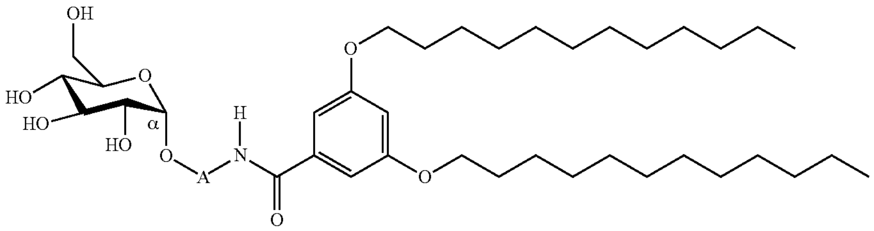

(III)

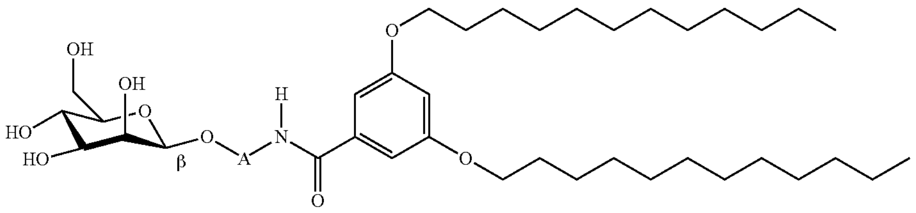

where A=$(CH_2)_{n'}$ with n'=2, 6, 10.

In some embodiments, the synthetic glycolipid of formula (I) is different than the following compound

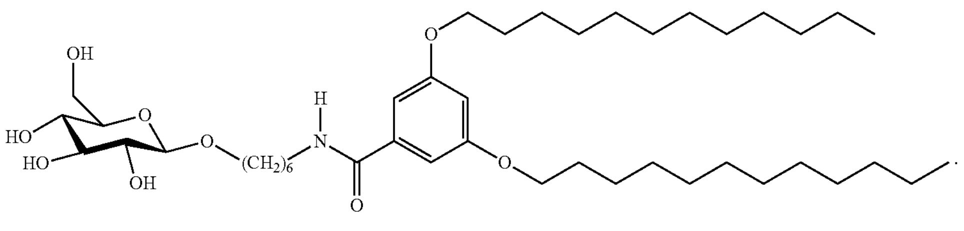

In some embodiments, the synthetic glycolipid of formula (I) is different than the compound of formula (IV)

(IV)

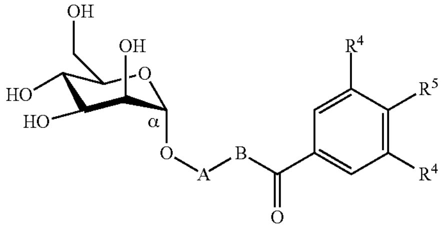

where A represents $CH_2$—$CH_2$; and

B represents NH, $R^4$ is H and R is $OC_{18}H_{37}$; or

B represents NH, R is H and $R^4$ are identical $OC_xH_y$ groups with x is 12, 14, 16, or 18 and y is 2x+1; or B represents NH, $R^4$ and R are identical and represent $OC_{18}H_{37}$; or B represents NMe, $R^4$ is $OC_{18}H_{37}$ and R is H.

In some embodiments, the synthetic glycolipid of formula (I) is different than the compound of formula (IV)

(IV)

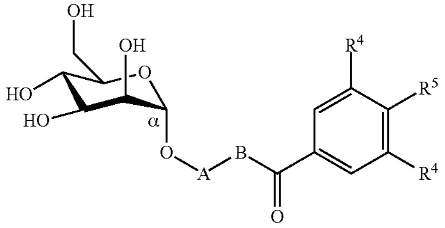

where A represents $CH_2$—$CH_2$;

and

B represents NH, R is H and $R^4$ are identical $OC_xH_y$ groups with x is 12, 14, 16, or 18 and y is 2x+1; or B represents NMe, $R^4$ is $OC_{18}H_{37}$ and R is H;

or where A represents —$(CH_2)_6$—, B represents NH, R is H and $R^4$ are both $O(CH_2)_{12}H$. In some embodiments, the synthetic glycolipid of formula (I) is different than the compound of formula (IV)

(IV)

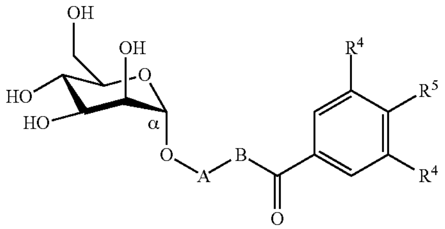

where A represents $(CH_2)_n$ with n being 2, 6 or 10; B represents NH, $R^4$ is $OC_{14}H_{29}$ and $R^5$ is H.

In some embodiments, in the formula (I), A can represent $(CH_2)_n$ with n being an integer from 2 to 10. For instance, A can represent $(CH_2)_n$ with n being 2 or 6. In some embodiments, A represents $(CH_2)_n$ with n=6.

In some embodiments, in the formula (I), A can represent $CH_2$—$CH_2$—[O—$CH_2$—$CH_2]_m$ with m being 2 or 3.

In some embodiments, the synthetic glycolipid can be represented by the formula (I) where B represents $NR^3$ where $R^3$ is as defined above. In some embodiments, B represents $NR^3$ where $R^3$ is H or Me. In some embodiments, B represents NH.

In some embodiments, the synthetic glycolipid has the formula (I) where X represents H, and Y and Z represent a group O—$(CH_2)_p$—$CH_3$, with p being an integer from 5 to 18. In other embodiments, X represents H, and Y and Z represent a group O—$(CH_2)_p$—$CH_3$, with p being 7, 9, 11, 13, 15 or 17.

In an alternative embodiment, the synthetic glycolipid can have the formula (I) where Y represents H, and X and Z then represent a group O—$(CH_2)_p$—$CH_3$, with p being an integer from 5 to 18. In some embodiments, Y represents H, and X and Z represent a group O—$(CH_2)_p$—$CH_3$, with p being 7, 9, 11, 13, 15 or 17. For instance, Y can represent H, and X and Z can represent a group O—$(CH_2)_p$—$CH_3$, with p=13.

In some embodiments, the synthetic glycolipid of the present disclosure can have the formula (I) where Sugar represents

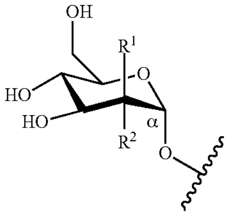

with $R^1$ representing OH and $R^2$ representing H, or with $R^1$ representing H and $R^2$ representing OH.

In some embodiments, the synthetic glycolipid of the present disclosure can have the formula (I) where Sugar represents

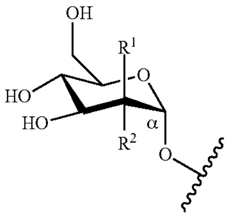

with $R^1$ representing OH and $R^2$ representing H.

In an alternative embodiment, the synthetic glycolipid of the present disclosure can have the formula (I) where Sugar represents

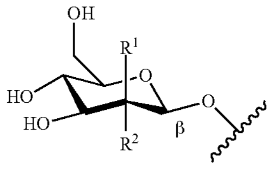

with $R^1$ representing OH and $R^2$ representing H, or where $R^1$ representing H and $R^2$ representing OH. In some embodiments, when the sugar has de beta conformation, $R^1$ represents OH and $R^2$ represents H.

In some embodiments, the glycoliposome can be a compound of formula (Ib)

(Ib)

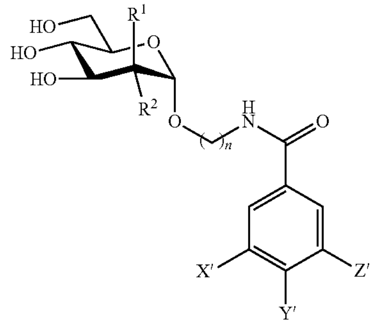

where a) $R^1$ is OH, $R^2$ is H, n=6, X'=—O—X, Y'=—O—Y, Z'=—O—Z, and
   $X=Z=C_8H_{17}$, Y=H (compound 12a), or
   $X=Z=C_{10}H_{21}$, Y=H (compound 12b), or
   $X=Z=C_{12}H_{25}$, Y=H (compound 12c), or
   $X=Z=C_{14}H_{29}$, Y=H (compound 12d), or
   $X=Z=C_{16}H_{33}$, Y=H (compound 12e), or
   $X=Z=C_{18}H_{37}$, Y=H (compound 12f), or
   X=H, $Y=Z=C_8H_{17}$ (compound 12g), or
   X=H, $Y=Z=C_{10}H_{21}$ (compound 12h), or
   X=H, $Y=Z=C_{12}H_{25}$ (compound 12i), or
   X=H, $Y=Z=C_{14}H_{19}$ (compound 12j), or
   X=H, $Y=Z=C_{16}H_{33}$ (compound 12k), or
   X=H, $Y=Z=C_{18}H_{37}$ (compound 12l);

or b) $R^1$ is OH, $R^2$ is H, n=2, X'=—O—X, Y'=—O—Y, Z'=—O—Z, and
   $X=Z=C_8H_{17}$, Y=H (compound 13a), or
   $X=Z=C_{10}H_{21}$, Y=H (compound 13b), or
   $X=Z=C_{12}H_{25}$, Y=H (compound 13c), or
   $X=Z=C_{14}H_{29}$, Y=H (compound 13d), or
   $X=Z=C_{16}H_{33}$, Y=H (compound 13e), or
   $X=Z=C_{18}H_{37}$, Y=H (compound 13f), or
   X=H, $Y=Z=C_8H_{17}$ (compound 13g), or
   X=H, $Y=Z=C_{10}H_{21}$ (compound 13h), or
   X=H, $Y=Z=C_{12}H_{25}$ (compound 13i), or
   X=H, $Y=Z=C_{14}H_{19}$ (compound 13j), or
   X=H, $Y=Z=C_{16}H_{33}$ (compound 13k), or
   X=H, $Y=Z=C_{18}H_{37}$ (compound 13l);

or c) $R^1$ is H, $R^2$ is OH, n=6, X'=—O—X, Y'=—O—Y, Z'=—O—Z, and
   $X=Z=C_8H_{17}$, Y=H (compound 12'a), or
   $X=Z=C_{10}H_{21}$, Y=H (compound 12'b), or
   $X=Z=C_{12}H_{25}$, Y=H (compound 12'c), or
   $X=Z=C_{14}H_{29}$, Y=H (compound 12'd), or
   $X=Z=C_{16}H_{33}$, Y=H (compound 12'e), or
   $X=Z=C_{18}H_{37}$, Y=H (compound 12'f), or
   X=H, $Y=Z=C_8H_{17}$ (compound 12'g), or
   X=H, $Y=Z=C_{10}H_{21}$ (compound 12'h), or
   X=H, $Y=Z=C_{12}H_{25}$ (compound 12'i), or
   X=H, $Y=Z=C_{14}H_{19}$ (compound 12'j), or
   X=H, $Y=Z=C_{16}H_{33}$ (compound 12'k), or
   X=H, $Y=Z=C_{18}H_{37}$ (compound 12'l);

or d) $R^1$ is H, $R^2$ is OH, n=6, X'=—O—X, Y'=—O—Y, Z'=—O—Z, and
   $X=Z=C_8H_{17}$, Y=H (compound 13'a), or
   $X=Z=C_{10}H_{21}$, Y=H (compound 13'b), or
   $X=Z=C_{12}H_{25}$, Y=H (compound 13'c), or
   $X=Z=C_{14}H_{29}$, Y=H (compound 13'd), or
   $X=Z=C_{16}H_{33}$, Y=H (compound 13'e), or
   $X=Z=C_{18}H_{37}$, Y=H (compound 13'f), or
   X=H, $Y=Z=C_8H_{17}$ (compound 13'g), or
   X=H, $Y=Z=C_{10}H_{21}$ (compound 13'h), or
   X=H, $Y=Z=C_{12}H_{25}$ (compound 13'i), or
   X=H, $Y=Z=C_{14}H_{19}$ (compound 13'j), or
   X=H, $Y=Z=C_{16}H_{33}$ (compound 13'k), or
   X=H, $Y=Z=C_{18}H_{37}$ (compound 13'l).

In some embodiments, the synthetic glycolipid of the present disclosure, can have the formula (Ia)

(Ia)

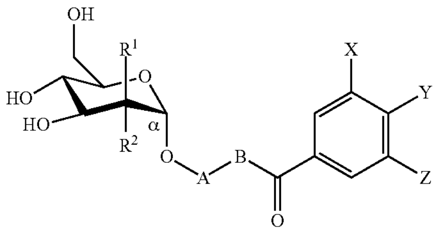

wherein

A represents $(CH_2)_n$ with n=6;
B represents NH;
$R^1$ represents OH and $R^2$ represents H;
Y represents H, and X and Z which are identical represent $O—(CH_2)_p—CH_3$, with p=13.

The above compound of formula (Ia) is also referred to as compound 12d or $MG_{12d}$ in the present disclosure.

In other embodiments, the glycoliposome can be a compound of formula (Ic)

(Ic)

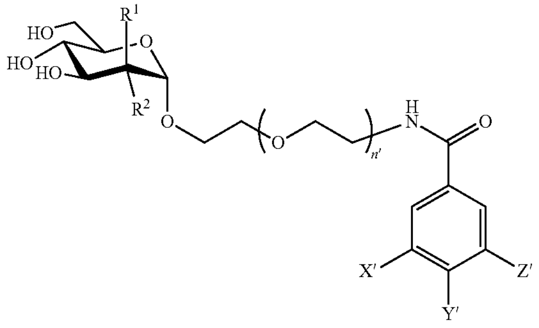

where a) $R^1$ is OH, $R^2$ is H, n'=2, X'=—O—X, Y'=—O—Y, Z'=—O—Z, and
   $X=Z=C_8H_{17}$, Y=H (compound 22a), or
   $X=Z=C_{10}H_{21}$, Y=H (compound 22b), or
   $X=Z=C_{12}H_{25}$, Y=H (compound 22c), or
   $X=Z=C_{14}H_{29}$, Y=H (compound 22d), or
   $X=Z=C_{16}H_{33}$, Y=H (compound 22e), or
   $X=Z=C_{18}H_{37}$, Y=H (compound 22f), or
   X=H, $Y=Z=C_8H_{17}$ (compound 22g), or X=H, Y=Z=$C_{10}H_{21}$ (compound 22h), or
X=H, Y=Z=$C_{12}H_{25}$ (compound 122i), or
X=H, Y=Z=$C_{14}H_{19}$ (compound 22j), or
X=H, Y=Z=$C_{16}H_{33}$ (compound 22k), or
X=H, Y=Z=$C_{18}H_{37}$ (compound 22l);

or b) $R^1$ is OH, $R^2$ is H, n'=3, X'=—O—X, Y'=—O—Y, Z'=—O—Z, and
X=Z=$C_8H_{17}$, Y=H (compound 23a), or
X=Z=$C_{10}H_{21}$, Y=H (compound 23b), or
X=Z=$C_{12}H_{25}$, Y=H (compound 23c), or
X=Z=$C_{14}H_{29}$, Y=H (compound 23d), or
X=Z=$C_{16}H_{33}$, Y=H (compound 23e), or
X=Z=$C_{18}H_{37}$, Y=H (compound 23f), or
X=H, Y=Z=$C_8H_{17}$ (compound 23g), or
X=H, Y=Z=$C_{10}H_{21}$ (compound 23h), or
X=H, Y=Z=$C_{12}H_{25}$ (compound 23i), or
X=H, Y=Z=$C_{14}H_{19}$ (compound 23j), or
X=H, Y=Z=$C_{16}H_{33}$ (compound 23k), or
X=H, Y=Z=$C_{18}H_{37}$ (compound 23l);

or c) $R^1$ is H, $R^2$ is OH, n'=2, X'=—O—X, Y'=—O—Y, Z'=—O—Z, and
X=Z=$C_8H_{17}$, Y=H (compound 24a), or
X=Z=$C_{10}H_{21}$, Y=H (compound 24b), or
X=Z=$C_{12}H_{25}$, Y=H (compound 24c), or
X=Z=$C_{14}H_{29}$, Y=H (compound 24d), or
X=Z=$C_{16}H_{33}$, Y=H (compound 24e), or
X=Z=$C_{18}H_{37}$, Y=H (compound 24f), or
X=H, Y=Z=$C_8H_{17}$ (compound 24g), or
X=H, Y=Z=$C_{10}H_{21}$ (compound 24h), or
X=H, Y=Z=$C_{12}H_{25}$ (compound 24i), or
X=H, Y=Z=$C_{14}H_{19}$ (compound 24j), or
X=H, Y=Z=$C_{16}H_{33}$ (compound 24k), or
X=H, Y=Z=$C_{18}H_{37}$ (compound 24l);

or d) $R^1$ is H, $R^2$ is OH, n'=3, X'=—O—X, Y'=—O—Y, Z'=—O—Z, and
X=Z=$C_8H_{17}$, Y=H (compound 25a), or
X=Z=$C_{10}H_{21}$, Y=H (compound 25b), or
X=Z=$C_{12}H_{25}$, Y=H (compound 25c), or
X=Z=$C_{14}H_{29}$, Y=H (compound 25d), or
X=Z=$C_{16}H_{33}$, Y=H (compound 25e), or
X=Z=$C_{18}H_{37}$, Y=H (compound 25f), or
X=H, Y=Z=$C_8H_{17}$ (compound 25g), or
X=H, Y=Z=$C_{10}H_{21}$ (compound 25h), or
X=H, Y=Z=$C_{12}H_{25}$ (compound 25i), or
X=H, Y=Z=$C_{14}H_{19}$ (compound 25j), or
X=H, Y=Z=$C_{16}H_{33}$ (compound 25k), or
X=H, Y=Z=$C_{18}H_{37}$ (compound 25l).

Synthesis of the Synthetic Glycolipids

In some aspects, the present disclosure relates to a process for the synthesis of the synthetic glycolipids described herein.

In some embodiments, the process for preparing the synthetic glycolipids of formula (I) as defined above can include a step of reducing a compound of formula (V)

(V)

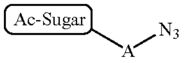

where 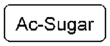 represents

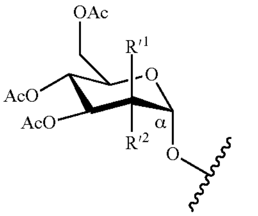

or

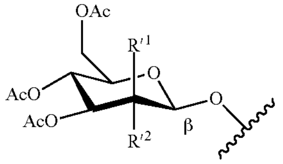

with $R'^1$ represents OAc and $R'^2$ represents H, or where $R'^1$ represents H and $R'^2$ represents OAc;

into the corresponding amine; and a step of coupling the amine with a compound of formula (VI)

(VI)

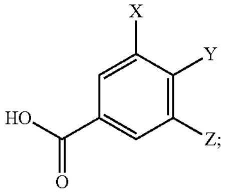

thereby forming the compound of formula ($I_{Ac}$)

($I_{Ac}$)

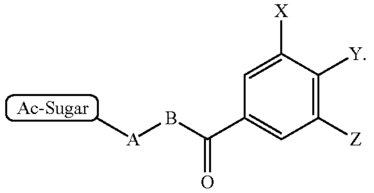

Then, the compound of formula ($I_{Ac}$) is converted into the synthetic glycolipid of formula (I).

In some particular embodiments, the process can allow to synthesize the synthetic glycolipid of formula (Ia) as defined above, by reducing the compound of formula (V) where 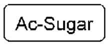 represents

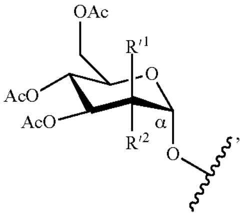

with $R'^1$ represents OAc and $R'^2$ represents H; and then coupling the resulting amino equivalent with the compound of formula (VI) where Y represents H, and X and Z which are identical represent O—$(CH_2)_p$—$CH_3$, with p=13.

The reducing and coupling steps can advantageously be performed as a one-pot synthesis without needing to isolate and purify intermediate compounds involved in these steps, still with good reaction yields.

In some embodiments, the reducing step can be performed by reacting a solution of the compound of formula (V) with a phosphine to form a first mixture comprising the amino equivalent of the compound of formula (V). Then, the coupling of the amino equivalent of the compound of formula (V) with the compound of formula (VI) can be performed by adding the compound of formula (VI) to the first mixture in the presence of a coupling agent, to form a second mixture comprising the compound of formula ($I_{Ac}$).

In the following step, the compound of formula ($I_{Ac}$) can be converted into the synthetic glycolipid of formula (I).

In another embodiment, the reducing step can be performed by reacting a solution comprising both the compound of formula (V) and formula (VI) with a phosphine to form a first mixture comprising the amino equivalent of the compound of formula (V) and the compound of formula (VI). Then, the coupling step can be performed by adding a coupling agent to the solution comprising the amino equivalent of the compound of formula (V) and the compound of formula (VI), to obtain a second mixture comprising the compound of formula ($I_{Ac}$). In the following step, the compound of formula ($I_{Ac}$) can be converted into the synthetic glycolipid of formula (I).

In some embodiments, the phosphine used for the reduction step can be a phosphine of formula $P(R'')_3$, where R'' can be a $C_5$-$C_6$aryl group, a $C_1$-$C_6$alkyl group, or $C_3$-$C_6$cycloalkyl group. In some embodiments, the phosphine can be $PPh_3$, $P(n\text{-}Bu)_3$, $P(s\text{-}Bu)_3$ or $P(t\text{-}Bu)_3$.

In some embodiments, the reduction step can involve adding the phosphine to the solution comprising the compound of formula (V), and optionally the compound of formula (VI), at low temperature, such as a temperature ranging from about 0° C. to about 10° C. for instance. A temperature of about 0° C. can be suitable.

In some embodiments, the process is performed in a solution comprising a non-aqueous polar, such as, without being limited to, $CH_2Cl_2$ (DCM), dimethylformamide (DMF), tetrahydrofuran (THF), dioxane, N, N-dimethylacetamide (DMA), N-methyl-2-pyrrolidone (NMP) or a combination thereof. In some particular embodiments, the non-aqueous polar solvent can be $CH_2Cl_2$.

In some embodiments, the coupling agent used for the coupling reaction between the amino equivalent of the compound of formula (V) and the compound of formula (VI) can be a peptide coupling agent. Any conventional peptide coupling agent can be used for the coupling step. For instance, the coupling agent can be one of the reagents cited in El-Faham et al., 2011.

In some embodiments, the coupling agent used for coupling the amino equivalent of the compound of formula (V) and the compound of formula (VI) can be selected from carbodiimides, phosphonium coupling agents, uronium coupling agents, thiouronium coupling agents, aminium coupling agents, immonium coupling agents, carbonate coupling agents, chloroformate coupling agents, imidazolium coupling agents, pyridinium coupling agents, triazole coupling agents, tetrazole coupling agents, organophosphorus agents, organosulfur agents, acid halide coupling agents, acyl azide coupling agents, acylazole coupling agents, anhydrides, active esters, and any combination thereof.

In some embodiments, the coupling agent can be selected from N,N'-diisopropylcarbodiimide (DIC), dicyclopentylcarbodiimide (CPC), dicyclohexylcarbodiimide (DCC), N-ethyl-N'-(3-dimethylaminopropyl)carbodiimide (EDC), tert-butylmethylcarbodiimide (BMC), tert-butylethylcarbodiimide (BEC), N-cyclohexyl,N'-isopropyl carbodiimide (CIC), bis[[4-(2,2-dimethyl-1,3-dioxolyl)]-methyl]-carbodiimide (BDDC), N-phenyl,N-isopropylcarbodiimide (PIC), N-ethyl,N-phenylcarbodiimide (PEC), carbonyl diimidazole (CDI), benzotriazole-1-yl-oxy-tris-(dimethylamino)phosphonium hexafluorophosphate (BOP), benzotriazol-1-yloxytri(pyrrolidino) phosphonium hexafluorophosphate (PyBOP), N-[(1H-benzotriazol-1-yl)(dimethylamino)-methylene]-N-methylmethanaminium hexafluorophosphate N-oxide (HBTU), N-[(1H-benzotriazol-1-yl)(dimethylamino)-methylene]-N-methylmethanaminium tetrafluoroborate N-oxide (TBTU), O-(7-azabenzotriazol-1-yl)-1,1,3,3-tetramethyluronium hexafluorophosphate (HATU), O-(6-Chlorobenzotriazol-1-yl)-N,N,N',N'-tetramethyluronium hexafluorophosphate (HCTU), O-(5-Norbornene-2,3-dicarboximido)-N,N,N',N'-tetramethyluronium tetrafluoroborate (TNTU), O-(1,2-Dihydro-2-oxo-1-pyridyl-N,N,N',N'-tetramethyluronium tetrafluoroborate (TPTU), O—(N-Succinimidyl)-1,1,3,3-tetramethyl-uronium tetrafluoroborate (TSTU), 1-hydroxybenzotriazole (HOBT), 1-hydroxy-7-azabenzotriazole (HOAt), 4-aza-1-hydroxybenzotriazole (4-HOAT), 5-aza-1-hydroxybenzotriazole (5-HOAT), 6-aza-1-hydroxybenzotriazole (6-HOAT), 3,4-dihydro-3-hydroxy-4-oxo-1,2,3-benzotriazine (HODhbt), 3-hydroxy-4-oxo-3,4-dihydro-5-azabenzo-1,2,3-triazene (HODhat), (HOPfp, N-Hydroxysuccinimide (HONSu), N-hydroxytetrazole, benzyltriphenylphosphonium dihydrogen trifluoride (PTF), chlorocarbonate, isopropenylchloroformate, isobutylchloroformate, and any combination thereof.

In some embodiments, the coupling agent is selected from hydroxybenzotriazole (HOBT), N,N'-diisopropylcarbodiimide (DIC), and a combination thereof.

In some embodiments, the process can further comprise recovering the compound of formula ($I_{Ac}$) from the reaction mixture and purifying the compound of formula ($I_{Ac}$) before the next step of conversion into the synthetic glycolipid of formula (I). Conventional methods can be used for isolating and purifying the compound of formula ($I_{Ac}$) such as, without being limited to, chromatography, and/or crystallisation.

In some embodiment, the conversion of the compound of formula ($I_{Ac}$) into the synthetic glycolipid of formula (I) can be performed by conventional de-O-acetylation methods. In some embodiments, the compound of formula ($I_{Ac}$) can be dissolved in an alcoholic solution (e.g., MeOH), a base (e.g., sodium methoxide) can be added to the solution, and the solution can be stirred until the compound of formula ($I_{Ac}$) is not detected anymore. The solution can then be neutralized and the synthetic glycolipid of formula (I) can be recovered from the neutralized solution.

Glycoliposomes

In some aspects, the present disclosure relates to glycoliposomes comprising or consisting essentially of the synthetic glycolipids described herein. More particularly, the synthetic glycolipids can be assembled to form a glycoliposome, e.g., a vesicle composed of a bilayer of the synthetic glycolipids enclosing a central cavity, which can be filled with water and/or a water miscible solvent, and can include the agent to be transported by the glycoliposomes. In some embodiments, the agent can be transported by the glycoliposomes through encapsulation and/or complexation.

In some embodiments, the glycoliposomes described herein are filled with water or an aqueous buffer solution. In other embodiments, the glycoliposomes are filled with a water miscible solvent, optionally with water. The water miscible solvent can be selected from tetrahydrofuran (THF), dioxane, an alcohol (e.g., ethanol, iso-propanol, tert-butanol), acetonitrile, to name a few examples. In some embodiments, the solvent can be selected to be compatible with the therapeutic or diagnostic agent to be transported into the glycoliposomes, i.e., a solvent capable of dissolving the therapeutic or diagnostic agent. In some embodiments, the solvent can be selected for biological applications. In some embodiments, the solvent can be an alcohol (e.g., ethanol, iso-propanol, tert-butanol). In some embodiments, the solvent can be phosphate-buffered saline (PBS).

In some embodiments, the preparation of the glycoliposomes can thus be performed in the presence of a therapeutic or diagnostic agent such that the therapeutic or diagnostic agent can be entrapped into the glycoliposomes. In some embodiments, more than one therapeutic or diagnostic agent can be entrapped into the glycoliposomes. For instance, the glycoliposomes can be prepared to contain a combination of two or more therapeutic or diagnostic agents.

In some embodiments, the glycoliposomes can be formed according to conventional methods. For instance, the glycoliposomes can be formed by preparing a solution of the synthetic glycolipids in water and/or solvent and supplying energy (e.g., mechanical agitation, sonication, heat) to initiate the assembling of the synthetic glycolipids into vesicles. In some embodiments, the glycoliposomes can be formed by film hydration, reverse phase evaporation, solvent injection, heating, microfluidic methods, or supercritical fluidic methods.

In some embodiments, the glycoliposomes can be subjected to post-preparation treatments, such as freeze-thawing or freeze-drying.

In some embodiments, the glycoliposomes can have a variety of diameters and can include small, large and even giant vesicles. The size of the glycoliposomes can be tailored by selecting the method of preparation. In some implementations, the glycoliposome size can be tailored by adjusting the proportion of solvents used (e.g., water to solvent ratio or different solvents ratio). In some embodiments, one can use a filter of a predetermined size to perform a screening and obtain glycoliposomes of a substantially uniform size. In some embodiments, the glycoliposomes can have a diameter ranging from about 10 nm to about 1000 nm. In some embodiments, the glycoliposomes diameter can range from about 10 nm to about 600 nm, or from about 10 nm to about 500 nm, or from 10 nm to about 400 nm, or from about 10 nm to about 300 nm, or from about 50 nm to about 300 nm, or from about 100 nm to about 300 nm, or from about 200 nm to about 300 nm. Hence, in some embodiments, the glycoliposomes can have diameters of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 325, 350, 375, 400, 450, 500, 550, and/or 600 nm.

In some embodiments, the glycoliposomes of the present disclosure may not require the use of an external stabilizer due to the (e.g., self-assembling) nature of the synthetic glycolipids, and the presence of the aromatic moiety therein, which can promote the co-assembling thereof in a substantially stable glycoliposomal structure. In some embodiments, the presence of an aromatic moiety in the synthetic glycolipids described herein may facilitate purification due to its absorbance of ultraviolet light (Tamiaki et al., 2006).

In some embodiments, if desired, the glycoliposomes can be prepared by adding a stabilizer to the synthetic glycolipids solution, thereby obtaining stabilized vesicles. In some embodiments, the stabilizer can include cholesterol, 0-sitosterol, stigmasterol, and/or phospholipids. In some embodiments, the phospholipids can be selected from 1,2-dilauroyl-sn-glycero-3-phosphocholine (DLPC), 1,2-ditetradecanoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-phosphocholine (DOPC), 1,2-Dimyristoyl-sn-glycero-3-phosphoethanolamine (DMPE), 1,2-Dipalmitoyl-sn-glycero-3-phosphoethanolamine (DPPE), 1,2-Dioleoyl-sn-glycero-3-phosphoethanolamine (DOPE), 1,2-Dimyristoyl-sn-glycero-3-phosphatidic acid, sodium salt (DMPA.Na), 1,2-Dipalmitoyl-sn-glycero-3-phosphatidic acid sodium salt (DPPA.Na), 1,2-dioleoyl-sn-glycero-3-phosphatidic acid sodium salt (DOPA.Na), 1,2-Dimyristoyl-sn-glycero-3-phospho-rac-(1-glycerol) sodium salt (DMPG.Na), 1,2-Dipalmitoyl-sn-glycero-3-phospho-rac-(1-glycerol) sodium salt (DPPG.Na), 1,2-Dioleoyl-sn-glycero-3-phospho-rac-(1-glycerol) sodium salt (DOPG.Na), 1,2-Dimyristoyl-sn-glycero-3-phospho-L-serine sodium salt (DMPS.Na), 1,2-dipalmitoyl-sn-glycero-3-phospho-L-serine sodium salt (DPPS.Na), 1,2-dioleoyl-sn-glycero-3-phospho-L-serine sodium salt (DOPS.Na), 1,2-dioleoyl-sn-glycero-3-phosphoethanolamine-N-(glutaryl) sodium salt (DOPE-Glutaryl.$(Na)_2$), 1',3'-bis[1,2-dimyristoleoyl-sn-glycero-3-phospho]-glycerol sodium salt, (Tetramyristoyl Cardiolipin.$(Na)_2$), 1,2-Distearoyl-rac-glycerol-3-Phosphoethanolamine-N-Polyethyleneglycol-2000 sodium salt (DSPE-mPEG-2000.Na), 1,2-Distearoyl-rac-glycerol-3-Phosphoethanolamine-N-Polyethyleneglycol-5000 sodium salt (DSPE-mPEG-5000.Na), and 1,2-distearoyl-sn-glycero-3-phosphoethanolamine-N-[maleimide(polyethylene glycol)-2000] sodium salt (DSPE-Maleimide PEG-2000.Na). In some embodiments, the previously listed sodium salts can be replaced with the corresponding ammonium salts. In some embodiments, the stabilizer can be N-[1-(2,3-Dioleoyloxy)propyl]-N,N,N-trimethylammonium chloride (DOTAP.Cl).

In some embodiments, the synthetic glycolipids described herein may have the ability to self-assemble into glycoliposomes upon exposure to aqueous solvent. In some embodiments, the glycoliposomes described herein may comprise one or more of the synthetic glycolipids described herein as a principal structural lipid component. As used herein, the expression "consisting essentially of" in the context of the membrane component of glycoliposomes described herein refer to the presence of one or more of the synthetic glycolipids described herein as the main or principal structural lipid component of the glycoliposomes, for example to take advantage of their self-assembling nature upon exposure to aqueous solvent. In some embodiments, the glycoliposomes described herein may comprise one or more of the synthetic glycolipids described herein as a principal structural lipid component. In some embodiments, glycoliposomes described herein may have a membrane component comprising at least 10, 15, 20, 25, 30, 35, 40, 45, 50, 55, 60, 65, 70, 75, 80, 85, 90, or 95 mol % of a single synthetic glycolipid described herein. In some embodiments, glycoliposomes described herein may have a membrane component comprising more than 10 mol % of a single synthetic glycolipid described herein. In some embodiments, glycoliposomes produced from a single type of glycolipid may be advantageous from a manufacturing and/or regulatory perspective. In some embodiments, glycoliposomes described herein seek to minimize the relative amount of naturally-derived components, such as sterols and/or amphipathic lipids (e.g., phospholipids), which may unnecessarily complexify manufacturing, purification, and/or formulation. In some embodiments, glycoliposomes described herein have a membrane component comprising less than 50, 45, 40, 35, 30, 25, 20, 15, 10, or 5 mol % of naturally-derived phospholipids (e.g., phosphatidylcholine).

Use of Glycoliposomes for Delivering Therapeutic or Diagnostic Agents to the Central Nervous System In some aspects, the glycoliposomes of the present disclosure can be used for delivering a therapeutic or diagnostic agent to the central nervous system (CNS) of a patient in need thereof, thanks to the ability of the present glycoliposomes to cross the blood brain barrier (BBB). More particularly, the therapeutic or diagnostic agent can be entrapped into the glycoliposomes, the glycoliposomes containing the entrapped therapeutic or diagnostic agent can be administered to the patient, and then the glycoliposomes can reach the CNS of the patient and deliver the therapeutic or diagnostic agent at the CNS.

In some embodiments, the therapeutic or diagnostic agent that can be entrapped into the glycoliposomes and delivered to the CNS can include a peptide, peptide analog, peptidomimetic (peptide mimetic), or small molecule. In some embodiments, the therapeutic or diagnostic agent can include a CNS receptor ligand, such as but not limited to a neurotransmitter receptor ligand, such as adrenergic, cholinergic (muscarinic or nicotinic), dopaminergic, GABAergic, glutaminergic, histaminergic, opioid, and serotonergic receptors for instance.

In some embodiments, the therapeutic or diagnostic agent can be an opioid receptor ligand, such as ligands specific to delta, kappa, mu, nociceptin receptor (NOR), or zeta opioid receptors for instance. In some embodiments, the ligand may be an agonist or an antagonist. In some embodiments, the therapeutic or diagnostic agent can be a κ-opioid receptor antagonist.

In certain embodiments, the therapeutic or diagnostic agent can include Dynantin, JVA-901, Arodyn, Cyclodyn, Zyklophin, [Pro3]- and [Pro3, Arg8]-Dyn A-(1-11)$NH_2$, Norbinaltorphimine (norBIN), 5'-Guanidinonaltrindole (GNTI), JDTic, ML140, ML140-11, Fedotozine, Asimadoline, ADL 10-1010, Salvinorin A, E-2078, SK-9709, JVA-901, or fragments or analogs thereof.

Therapeutic Treatments Using the Glycoliposomes

In some aspects, the present disclosure also relates to therapeutic treatments involving the use of the glycoliposomes described herein to deliver a therapeutic or diagnostic agent to a patient in need of such treatments. The therapeutic treatment can involve administering a dosage form containing the glycoliposomes with the therapeutic or diagnostic agent entrapped therein to the patient. Following administration, the glycoliposomes can reach the CNS of the patient where the therapeutic or diagnostic agent is delivered and allowed to treat a CNS-related disease or disorder.

The dosage forms containing the glycoliposomes can be liquid or solid dosage forms. In other embodiments, the dosage forms can be a cream or an ointment or a sprayable dosage form. The dosage form can be adapted depending on the mode of administration.

In some embodiments, the glycoliposomes can be administered parenterally, such as by subcutaneous, intravenous, intranasal, intramuscular, intrathecal, and intracranial injection techniques.

Other modes of administration also include intradermal or transdermal administration. In one particular embodiment, the glycoliposomes can be administered by intranasal, intravenous, intrathecal, or transdermal injection.

Liquid dosage forms can be used for oral administration and can include emulsions, microemulsions, solutions, suspensions, syrups and elixirs containing the glycoliposomes. In addition to the glycoliposomes containing the therapeutic or diagnostic agent(s), the liquid dosage forms may contain inert diluents commonly used in the art.

Solid dosage forms for oral administration can include capsules, tablets, pills, powders, and granules. In such solid dosage forms, the glycoliposomes can be mixed with at least one inert excipient or carrier.

Injectable preparations, for example, sterile injectable aqueous or oleaginous suspensions may be formulated according to the known art using suitable dispersing or wetting agents and suspending agents.

The glycoliposomes may also be administered by nasal aerosol or inhalation. Dosage forms for intranasal administration or inhalation can be prepared as saline solutions, employing suitable preservatives, absorption promotors to enhance bioavailability, fluorocarbons, and/or other conventional solubilizing or dispersing agents.

Dosage forms for topical administration can include ointments, pastes, creams, lotions, gels, solutions, or patches. The glycoliposomes can be admixed under sterile conditions with a suitable carrier and any needed preservatives or buffers as required.

In some embodiments, the administration of the glycoliposomes can be performed intravenously, intranasally, sublingually, orally, by inhalation, topically, intrathecally, or via transdermal administration. In particular embodiments, the glycoliposome can be administered intranasally, or by inhalation.

In some embodiments, the glycoliposomes can be used to deliver a therapeutic or diagnostic agent for the treatment of a CNS-related disease or disorder such as but not limited to a neurodegenerative disease or disorder (e.g., Parkinson's or Multiple Sclerosis), depression, post-traumatic stress disorder, stress, anxiety, addiction, drug abuse or addiction, pain, eating disorder, psychiatric or mood disorders, psychosis, or schizophrenia.

In some aspects, the present disclosure relates to a pharmaceutical composition comprising the glycoliposome defined herein and one or more pharmaceutically-acceptable excipient or carrier.

In some embodiments, the glycoliposomes or pharmaceutical composition defined herein may be used or administered in combination with known treatment regimens for the treatment of CNS-related diseases or disorders.

In some aspects, the present disclosure relates to a use of the glycoliposomes or pharmaceutical composition defined herein, for the treatment of a CNS-related disease or disorder.

In some aspects, the present disclosure relates to a use of the glycoliposomes or pharmaceutical composition defined herein, for the manufacture of a medicament for the treatment of a CNS-related disease or disorder.

In some aspects, the present disclosure relates to a method for treating a CNS-related disease or disorder in a patient in need thereof, said method comprising administering the glycoliposomes or pharmaceutical composition defined herein to the patient.

Items

Described herein are one or more of the following items.

Item 1. A synthetic glycolipid having the formula (I)

(I)

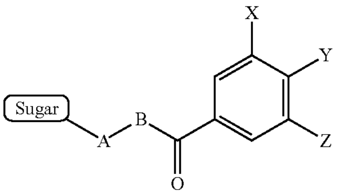

wherein

A represents $(CH_2)_n$ with n being an integer from 2 to 10 or $CH_2—CH_2—[O—CH_2—CH_2]_m$ with m being 2 or 3;

B represents $NR^3$, with $R^3$ representing H, Me, Et or n-Pr;

Sugar represents

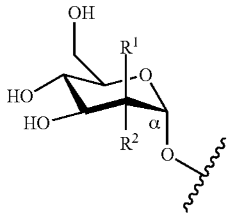

or

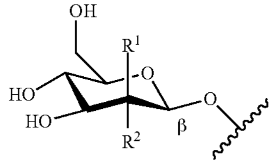

where $R^1$ represents OH and $R^2$ represents H, or where $R^1$ represents H and $R^2$ represents OH;

Y represents H when X and Z which are identical represent $O—(CH_2)_p—CH_3$, or X represents H when Y and Z which are identical represent $O—(CH_2)_p—CH_3$, with p being an integer from 5 to 18;

with the proviso that the synthetic glycolipid of formula (I) is different than the compound of formula (II) or (III)

(II)

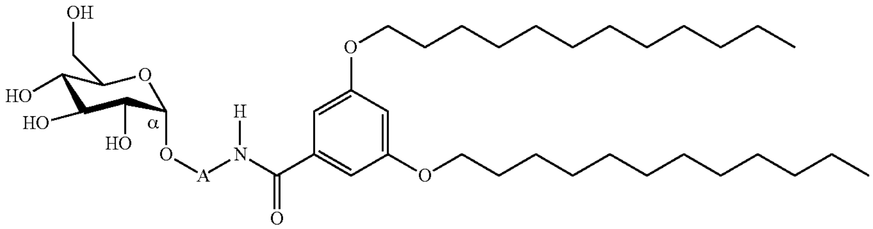

(III)

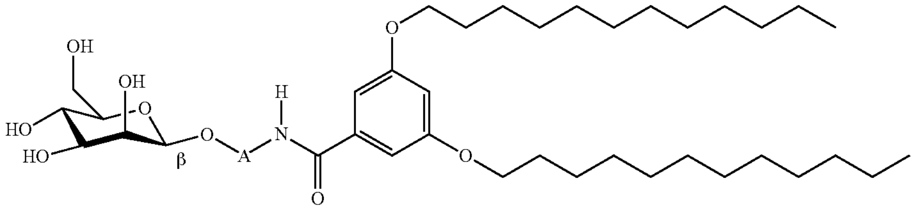

where $A=(CH_2)_{n'}$ with n'=2, 6, 10;

with the proviso that the synthetic glycolipid of formula (I) is different than the following compound

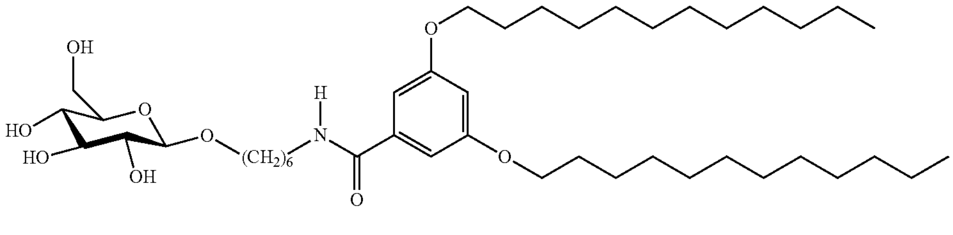

;

and with the proviso that the synthetic glycolipid of formula (I) is different than the compound of formula (IV)

(IV)

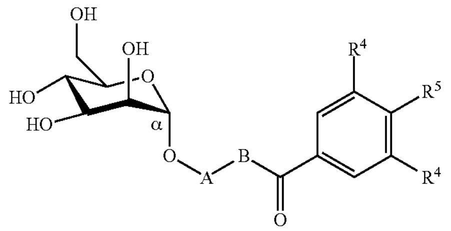

where A represents $CH_2$—$CH_2$;

and

B represents NH, R is H and $R^4$ are identical $OC_xH_y$ groups with x is 12, 14, 16, or 18 and y is 2x+1; or B represents NMe, $R^4$ is $OC_{18}H_{37}$ and R is H;

or where A represents —$(CH_2)_6$—, B represents NH, $R^5$ is H and $R^4$ are both $O(CH_2)_{12}H$.

Item 2. The synthetic glycolipid of item 1, with the further proviso that the synthetic glycolipid of formula (I) is different than the compound of formula (IV)

(IV)

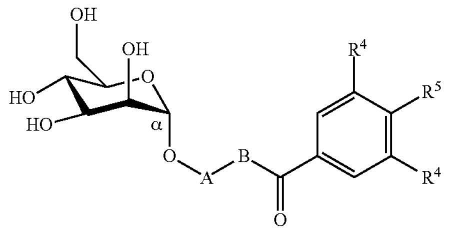

where A represents $(CH_2)_n$ with n being 2, 6 or 10; B represents NH, $R^4$ is $OC_{14}H_{29}$ and $R^5$ is H.

Item 3. The synthetic glycolipid of item 1 or 2, wherein A represents $(CH_2)_n$ with n being an integer from 2 to 10.

Item 4. The synthetic glycolipid of item 1 or 2, wherein A represents $(CH_2)_n$ with n being 2 or 6.

Item 5. The synthetic glycolipid of item 1 or 2, wherein A represents $(CH_2)_n$ with n=6.

Item 6. The synthetic glycolipid of item 1 or 2, wherein A represents $CH_2$—$CH_2$—[O—$CH_2$—$CH_2$]$_m$ with m being 2 or 3.

Item 7. The synthetic glycolipid of any one of items 1 to 6, wherein B represents $NR^3$ where $R^3$ is H or Me.

Item 8. The synthetic glycolipid of any one of items 1 to 6, wherein B represents NH.

Item 9. The synthetic glycolipid of any one of items 1 to 8, wherein X represents H, and Y and Z represent a group O—$(CH_2)_p$—$CH_3$, with p being an integer from 5 to 18.

Item 10. The synthetic glycolipid of any one of items 1 to 8, wherein X represents H, and Y and Z represent a group O—$(CH_2)_p$—$CH_3$, with p being 7, 9, 11, 13, 15 or 17.

Item 11. The synthetic glycolipid of any one of items 1 to 8, wherein Y represents H, and X and Z represent a group O—$(CH_2)_p$—$CH_3$, with p being an integer from 5 to 18.

Item 12. The synthetic glycolipid of any one of items 1 to 8, wherein Y represents H, and X and Z represent a group O—$(CH_2)_p$—$CH_3$, with p being 7, 9, 11, 13, 15 or 17.

Item 13. The synthetic glycolipid of any one of items 1 to 8, wherein Y represents H, and X and Z represent a group O—$(CH_2)_p$—$CH_3$, with p=13.

Item 14. The synthetic glycolipid of any one of items 1 to 13, wherein

Sugar represents

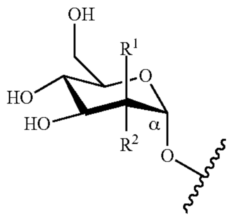

where $R^1$ represents OH and $R^2$ represents H, or where $R^1$ represents H and $R^2$ represents OH.

Item 15. The synthetic glycolipid of any one of items 1 to 13, wherein

Sugar represents

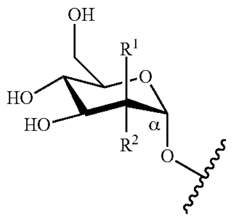

where $R^1$ represents OH and $R^2$ represents H.

Item 16. The synthetic glycolipid of any one of items 1 to 13, wherein

Sugar represents

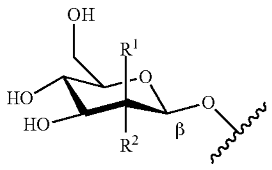

where $R^1$ represents OH and $R^2$ represents H, or where $R^1$ represents H and $R^2$ represents OH.

Item 17. The synthetic glycolipid of item 1, having the formula (Ia)

(Ia)

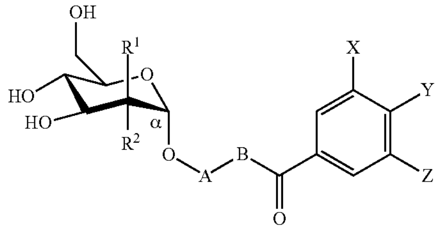

wherein

A represents $(CH_2)_n$ with n=6;

B represents NH;

$R^1$ represents OH and $R^2$ represents H;

Y represents H, and X and Z which are identical represent O—$(CH_2)_p$—$CH_3$, with p=13.

Item 18. A glycoliposome comprising or consisting essentially of a plurality of synthetic glycolipids as defined in any one of items 1 to 17.

Item 19. Use of the glycoliposome of item 18, for the delivery of a therapeutic or diagnostic agent to the central nervous system.

Item 20. A glycoliposome for use in delivering a therapeutic or diagnostic agent to the central nervous system, wherein the glycoliposome comprises or consists essentially of a plurality of synthetic glycolipids and each synthetic glycolipid has the following formula (I)

(I)

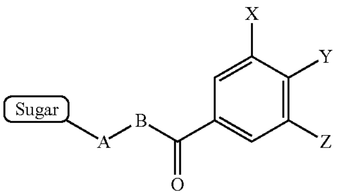

wherein

A represents $(CH_2)_n$ with n being an integer from 2 to 10 or $CH_2$—$CH_2$—[O—$CH_2$—$CH_2$]$_m$ with m being an integer from 1 to 5;

B represents $NR^3$ or $OCH_2$, with $R^3$ representing H, Me, Et or n-Pr;

Sugar represents

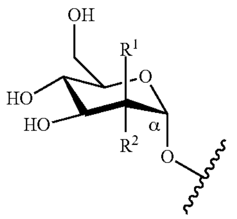

or

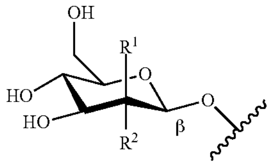

where $R^1$ represents OH and $R^2$ represents H, or where $R^1$ represents H and $R^2$ represents OH;

Y represents H when X and Z which are identical represent O—$(CH_2)_p$—$CH_3$, or X represents H when Y and Z which are identical represent O—$(CH_2)_p$—$CH_3$, with p being an integer from 5 to 18.

Item 21. The glycoliposome for use in delivering a therapeutic or diagnostic agent to the central nervous system according to item 20, wherein A represents $(CH_2)_n$ with n being an integer from 2 to 10.

Item 22. The glycoliposome for use in delivering a therapeutic or diagnostic agent to the central nervous system according to item 20, wherein A represents $(CH_2)_n$ with n being 2 or 6.

Item 23. The glycoliposome for use in delivering a therapeutic or diagnostic agent to the central nervous system according to item 20, wherein A represents $(CH_2)_n$ with n=6.

Item 24. The glycoliposome for use in delivering a therapeutic or diagnostic agent to the central nervous system according to item 20, wherein A represents $CH_2$—$CH_2$—[O—$CH_2$—$CH_2$]$_m$ with m being 2 or 3.

Item 25. The glycoliposome for use in delivering a therapeutic or diagnostic agent to the central nervous system according to any one of items 20 to 24, wherein B represents $NR^3$ where $R^3$ is as defined in item 20.

Item 26. The glycoliposome for use in delivering a therapeutic or diagnostic agent to the central nervous system according to any one of items 20 to 24, wherein B represents NH.

Item 27. The glycoliposome for use in delivering a therapeutic or diagnostic agent to the central nervous system according to any one of items 20 to 26, wherein X represents H, and Y and Z represent a group O—$(CH_2)_p$—$CH_3$, with p being an integer from 5 to 18.

Item 28. The glycoliposome for use in delivering a therapeutic or diagnostic agent to the central nervous system according to any one of items 20 to 26, X represents H, and Y and Z represent a group O—$(CH_2)_p$—$CH_3$, with p being 7, 9, 11, 13, 15 or 17.

Item 29. The glycoliposome for use in delivering a therapeutic or diagnostic agent to the central nervous system according to any one of items 20 to 26, wherein Y represents H, and X and Z represent a group O—$(CH_2)_p$—$CH_3$, with p being an integer from 5 to 18.

Item 30. The glycoliposome for use in delivering a therapeutic or diagnostic agent to the central nervous system according to any one of items 20 to 26, wherein Y represents H, and X and Z represent a group O—$(CH_2)_p$—$CH_3$, with p being 7, 9, 11, 13, 15 or 17.

Item 31. The glycoliposome for use in delivering a therapeutic or diagnostic agent to the central nervous system according to any one of items 20 to 26, wherein Y represents H, and X and Z represent a group O—$(CH_2)_p$—$CH_3$, with p=13.

Item 32. The glycoliposome for use in delivering a therapeutic or diagnostic agent to the central nervous system according to any one of items 20 to 31, wherein Sugar represents

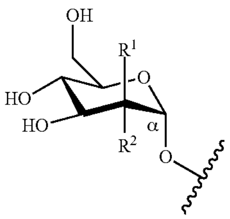

where $R^1$ represents OH and $R^2$ represents H, or where $R^1$ represents H and $R^2$ represents OH.

Item 33. The glycoliposome for use in delivering a therapeutic or diagnostic agent to the central nervous system according to any one of items 20 to 31, wherein Sugar represents

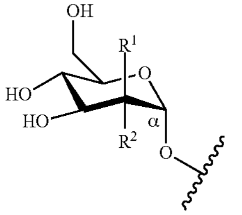

where $R^1$ represents OH and $R^2$ represents H.

Item 34. The glycoliposome for use in delivering a therapeutic or diagnostic agent to the central nervous system according to any one of items 20 to 31, wherein Sugar represents

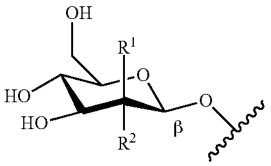

where $R^1$ represents OH and $R^2$ represents H, or where $R^1$ represents H and $R^2$ represents OH.

Item 35. The glycoliposome for use in delivering a therapeutic or diagnostic agent to the central nervous system according to item 20, wherein each synthetic glycolipid has the formula (Ia)

(Ia)

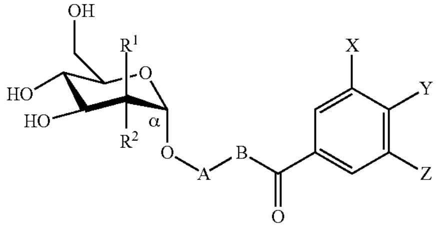

wherein

A represents $(CH_2)_n$ with n=6;

B represents NH;

$R^1$ represents OH and $R^2$ represents H;

Y represents H, and X and Z which are identical represent O—$(CH_2)_p$—$CH_3$, with p=13.

Item 36. A method for delivering a therapeutic or diagnostic agent to the central nervous system of a patient in need of the therapeutic or diagnostic agent, comprising:

entrapping the therapeutic or diagnostic agent into a glycoliposome comprising a plurality of synthetic glycolipids; and administering the glycoliposome with the entrapped therapeutic or diagnostic agent to the patient;

wherein each synthetic glycolipid has the following formula (I)

(I)

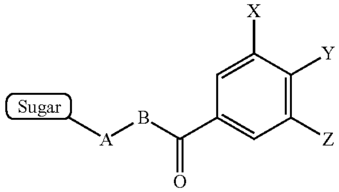

wherein

A represents $(CH_2)_n$ with n being an integer from 2 to 10 or $CH_2$—$CH_2$—[O—$CH_2$—$CH_2$]$_m$ with m being an integer from 1 to 5;

B represents $NR^3$ or $OCH_2$, with $R^3$ representing H, Me, Et or n-Pr;

Sugar represents

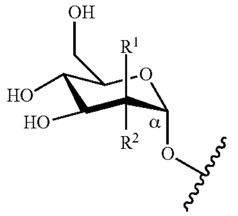

or

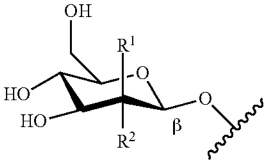

where $R^1$ represents OH and $R^2$ represents H, or where $R^1$ represents H and $R^2$ represents OH;

Y represents H when X and Z which are identical represent O—$(CH_2)_p$—$CH_3$, or X represents H when Y and Z which are identical represent O—$(CH_2)_p$—$CH_3$, with p being an integer from 5 to 18.

Item 37. The method of item 36, wherein A represents $(CH_2)_n$ with n being an integer from 2 to 10.

Item 38. The method of item 36, wherein A represents $(CH_2)_n$ with n being 2 or 6.

Item 39. The method of item 36, wherein A represents $(CH_2)_n$ with n=6.

Item 40. The method of item 36, wherein A represents $CH_2$—$CH_2$—[O—$CH_2$—$CH_2$]$_m$ with m being 2 or 3.

Item 41. The method of any one of items 36 to 40, wherein B represents $NR^3$ where $R^3$ is as defined in item 36.

Item 42. The method of any one of items 36 to 40, wherein B represents NH.

Item 43. The method of any one of items 36 to 42, wherein X represents H, and Y and Z represent a group O—$(CH_2)_p$—$CH_3$, with p being an integer from 5 to 18.

Item 44. The method of any one of items 36 to 42, X represents H, and Y and Z represent a group O—$(CH_2)_p$—$CH_3$, with p being 7, 9, 11, 13, 15 or 17.

Item 45. The method of any one of items 36 to 42, wherein Y represents H, and X and Z represent a group O—$(CH_2)_p$—$CH_3$, with p being an integer from 5 to 18.

Item 46. The method of any one of items 36 to 42, wherein Y represents H, and X and Z represent a group O—$(CH_2)_p$—$CH_3$, with p being 7, 9, 11, 13, 15 or 17.

Item 47. The method of any one of items 36 to 42, wherein Y represents H, and X and Z represent a group O—$(CH_2)_p$—$CH_3$, with p=13.

Item 48. The method of any one of items 36 to 47, wherein Sugar represents

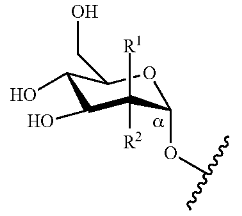

where $R^1$ represents OH and $R^2$ represents H, or where $R^1$ represents H and $R^2$ represents OH Item 49. The method of any one of items 36 to 47, wherein Sugar represents

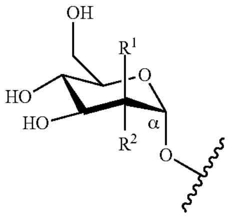

where $R^1$ represents OH and $R^2$ represents H.

Item 50. The method of any one of items 36 to 47, wherein Sugar represents

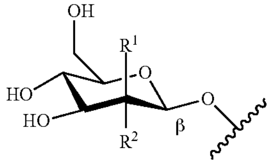

where $R'^1$ represents OH and $R^2$ represents H, or where $R^1$ represents H and $R^2$ represents OH.

Item 51. The method of item 36, wherein each synthetic glycolipid has the formula (Ia)

(Ia)

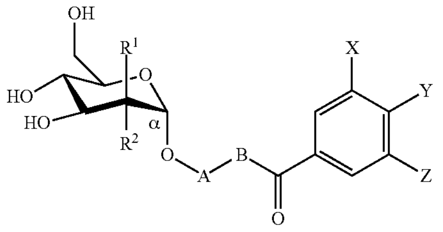

wherein

A represents $(CH_2)_n$ with n=6;

B represents NH;

$R^1$ represents OH and $R^2$ represents H;

Y represents H, and X and Z which are identical represent O—$(CH_2)_p$—$CH_3$, with p=13.

Item 52. The use of item 19, the glycoliposome for use according to any one of items 20 to 35, or the method of any one of items 36 to 51, wherein the therapeutic or diagnostic agent comprises a peptide, peptide analog, peptidomimetic (peptide mimetic), or small molecule.

Item 53. The use of item 19, the glycoliposome for use according to any one of items 20 to 35, or the method of any one of items 36 to 51, wherein the therapeutic or diagnostic agent comprises a neurotransmitter receptor ligand.

Item 54. The use of item 19, the glycoliposome for use according to any one of items 20 to 35, or the method of any one of items 36 to 51, wherein the therapeutic or diagnostic agent comprises an opioid receptor ligand.

Item 55. The use of item 19, the glycoliposome for use according to any one of items 20 to 35, or the method of any one of items 36 to 51, wherein the therapeutic or diagnostic agent comprises a κ-opioid receptor antagonist.

Item 56. The use of item 19, the glycoliposome for use according to any one of items 20 to 35, or the method of any one of items 36 to 51, wherein the therapeutic or diagnostic agent comprises Dynantin, JVA-901, Arodyn, Cyclodyn, Zyklophin, [Pro3]- and [Pro3, Arg8]-Dyn A-(1-11)$NH_2$, Norbinaltorphimine (norBIN), 5'-Guanidinonaltrindole (GNTI), JDTic, ML140, ML140-11, Fedotozine, Asimadoline, ADL 10-1010, Salvinorin A, E-2078, SK-9709, JVA-901, or fragments or analogs thereof.

Item 57. The use of item 19 or the glycoliposome for use according to any one of items 20 to 35, or the method of any one of items 36 to 51, wherein the glycoliposome is to be administered intravenously, intranasally, sublingually, orally, by inhalation, topically, intrathecally, or via transdermal administration.

Item 58. The use of item 19 or the glycoliposome for use according to any one of items 20 to 35, or the method of any one of items 36 to 51, wherein the glycoliposome is to be administered intranasally, or by inhalation.

Item 59. The use of item 19, the glycoliposome for use according to any one of items 20 to 35, or the method of any one of items 36 to 51, wherein the use or method is for the treatment of a CNS-related disease or disorder.

Item 60. The use of item 19, the glycoliposome for use according to any one of items 20 to 35, or the method of any one of items 36 to 51, wherein the use or method is for the treatment of a neurodegenerative disease or disorder, depression, post-traumatic stress disorder, stress, anxiety, addiction, drug abuse or addiction, pain, eating disorder, psychiatric or mood disorders, psychosis, or schizophrenia.

Item 61. Use of the glycoliposome of item 19, for the treatment of a CNS-related disease or disorder.

Item 62. Use of the glycoliposome of item 19, for the manufacture of a medicament for the treatment of a CNS-related disease or disorder.

Item 63. The use of item 61 or 62, wherein the CNS-related disease or disorder is a neurodegenerative disease or disorder, depression, post-traumatic stress disorder, stress, anxiety, addiction, drug abuse or addiction, pain, eating disorder, psychiatric or mood disorders, psychosis, or schizophrenia.

Item 64. A method for treating a CNS-related disease or disorder in a patient in need thereof, said method comprising administering the glycoliposome as defined in item 19 to the patient.

Item 65. The method of item 64, wherein the CNS-related disease or disorder is a neurodegenerative disease or disorder, depression, post-traumatic stress disorder, stress, anxiety, addiction, drug abuse or addiction, pain, eating disorder, psychiatric or mood disorders, psychosis, or schizophrenia.

Item 66. A process for preparing a synthetic glycolipid having the following formula (I)

(I)

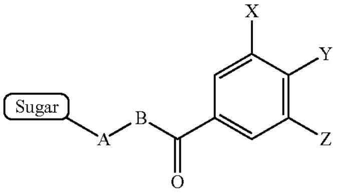

wherein

A represents $(CH_2)_n$ with n being an integer from 2 to 10 or $CH_2—CH_2—[O—CH_2—CH_2]_m$ with m being an integer from 1 to 5;

B represents NH;

Sugar represents

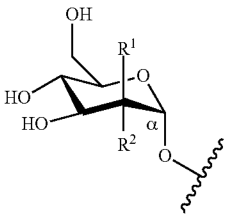

or

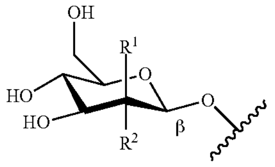

where $R^1$ represents OH and $R^2$ represents H, or where $R^1$ represents H and $R^2$ represents OH;

Y represents H when X and Z which are identical represent $O—(CH_2)_p—CH_3$, or X represents H when Y and Z which are identical represent $O—(CH_2)_p—CH_3$, with p being an integer from 5 to 18;

the process comprising:

reducing a compound of formula (V)

(V)

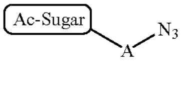

where Ac-Sugar represents

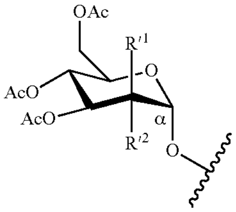

or

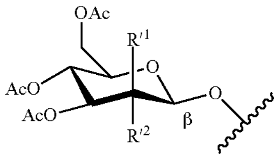

with $R'^1$ represents OAc and $R'^2$ represents H, or where $R'^1$ represents H and $R'^2$ represents OAc;

into the corresponding amine; and coupling the amine with a compound of formula (VI)

(VI)

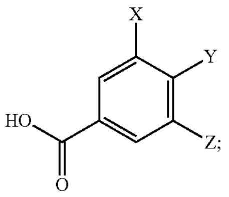

thereby forming the compound of formula $(I_{Ac})$ $(I_{Ac})$

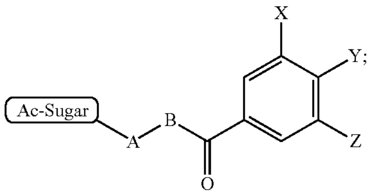

and converting the compound of formula $(I_{Ac})$ into the synthetic glycolipid of formula (I).

Item 67. The process of item 66, wherein the step of reducing and coupling are performed as a one-pot synthesis.

Item 68. The process of item 66 or 67, wherein the reducing is performed by reacting a solution of the compound of formula (V) with a phosphine to form a first mixture comprising the amine, then the compound of formula (VI) is added to the first mixture and reacted with the amine in the presence of a coupling agent, to form a second mixture comprising the compound of formula $(I_{Ac})$.

Item 69. The process of item 66 or 67, wherein the reducing is performed by reacting a solution comprising the compound of formula (V) and formula (VI) with a phosphine to form a first mixture comprising the amine and the compound of formula (VI), and the coupling is performed by adding a coupling agent to then obtain a second mixture comprising the compound of formula $(I_{Ac})$.

Item 70. The process of item 68 or 69, wherein the coupling agent is a peptide coupling agent.

Item 71. The process of item 68 or 69, wherein the coupling agent is selected from the group consisting of carbodiimides, phosphonium coupling agents, uronium coupling agents, thiouronium coupling agents, aminium coupling agents, immonium coupling agents, carbonate coupling agents, chloroformate coupling agents, imidazolium coupling agents, pyridinium coupling agents, triazole coupling agents, tetrazole coupling agents, organophosphorus agents, organosulfur agents, acid halide coupling agents, acyl azide coupling agents, acylazole coupling agents, anhydrides, active esters, and any combination thereof.

Item 72. The process of item 68 or 69, wherein the coupling agent is selected from the group consisting of N,N'-diisopropylcarbodiimide (DIC), dicyclopentylcarbodiimide (CPC), dicyclohexylcarbodiimide (DCC), N-ethyl-N'-(3-dimethylaminopropyl)carbodiimide (EDC), tert-butylmethylcarbodiimide (BMC), tert-butylethylcarbodiimide (BEC), N-cyclohexyl,N'-isopropyl carbodiimide (CIC), bis[[4-(2,2-dimethyl-1,3-dioxolyl)]-methyl]-carbodiimide (BDDC), N-phenyl,N-isopropylcarbodiimide (PIC), N-ethyl,N-phenylcarbodiimide (PEC), carbonyl diimidazole (CDI), benzotriazole-1-yl-oxy-tris-(dimethylamino) phosphonium hexafluorophosphate (BOP), benzotriazol-1-yloxytri(pyrrolidino) phosphonium hexafluorophosphate (PyBOP), N-[(1H-benzotriazol-1-yl)(dimethylamino)-methylene]-N-methylmethanaminium hexafluorophosphate N-oxide (HBTU), N-[(1H-benzotriazol-1-yl)(dimethylamino)-methylene]-N-methylmethanaminium tetrafluoroborate N-oxide (TBTU), O-(7-azabenzotriazol-1-yl)-1,1,3,3-tetramethyluronium hexafluorophosphate (HATU), O-(6-Chlorobenzotriazol-1-yl)-N,N,N',N'-tetramethyluronium hexafluorophosphate (HCTU), O-(5-Norbornene-2,3-dicarboximido)-N,N,N',N'-tetramethyluronium tetrafluoroborate (TNTU), O-(1,2-Dihydro-2-oxo-1-pyridyl-N,N,N',N'-tetramethyluronium tetrafluoroborate (TPTU), O—(N-Succinimidyl)-1,1,3,3-tetramethyl-uronium tetrafluoroborate (TSTU), 1-hydroxybenzotriazole (HOBT), 1-hydroxy-7-azabenzotriazole (HOAt), 4-aza-1-hydroxybenzotriazole (4-HOAT), 5-aza-1-hydroxybenzotriazole (5-HOAT), 6-aza-1-hydroxybenzotriazole (6-HOAT), 3,4-dihydro-3-hydroxy-4-oxo-1,2,3-benzotriazine (HODhbt), 3-hydroxy-4-oxo-3,4-dihydro-5-azabenzo-1,2,3-triazene (HODhat), (HOPfp, N-Hydroxysuccinimide (HONSu), N-hydroxytetrazole, benzyltriphenylphosphonium dihydrogen trifluoride (PTF), chlorocarbonate, isopropenylchloroformate, isobutylchloroformate, and any combination thereof.

Item 73. The process of item 68 or 69, wherein the coupling agent is selected from the group consisting of hydroxybenzotriazole (HOBT), N,N'-diisopropylcarbodiimide (DIC), and a combination thereof.

Item 74. The process of any one of items 68 to 73, wherein the phosphine is of formula $P(R'')_3$, where R" is a $C_5$-$C_6$aryl group, a $C_1$-$C_6$alkyl group, or $C_3$-$C_6$cycloalkyl group.

Item 75. The process of any one of items 68 to 74, wherein the phosphine is $PPh_3$, $P(n\text{-}Bu)_3$, $P(s\text{-}Bu)_3$ or $P(t\text{-}Bu)_3$.

Item 76. The process of any one of items 68 to 75, wherein the reaction with the phosphine comprises adding the phosphine to the solution at a temperature ranging from about 0° C. to about 10° C.

Item 77. The process of any one of items 68 to 76, wherein the solution comprises a non-aqueous polar solvent.

Item 78. The process of item 77, wherein the non-aqueous polar solvent comprises $CH_2Cl_2$ (DCM), dimethylformamide (DMF), tetrahydrofuran (THF), dioxane, N,N-dimethylacetamide (DMA), N-methyl-2-pyrrolidone (NMP), or a combination thereof.

Item 79. The process of item 77 or 78, wherein the non-aqueous polar solvent is $CH_2Cl_2$.

Item 80. The process of any one of items 68 to 79, further comprising recovering the compound of formula ($I_{Ac}$) from the second mixture and purifying the compound of formula ($I_{Ac}$).

Item 81. The process of any one of items 66 to 80, wherein A represents $(CH_2)_n$ with n being an integer from 2 to 10.

Item 82. The process of any one of items 66 to 80, wherein A represents $(CH_2)_n$ with n being 2 or 6.

Item 83. The process of any one of items 66 to 80, wherein A represents $(CH_2)_n$ with n=6.

Item 84. The process of any one of items 66 to 80, wherein A represents $CH_2$—$CH_2$—[O—$CH_2$—$CH_2$]$_m$ with m being 2 or 3.

Item 85. The process of any one of items 66 to 84, wherein X represents H, and Y and Z represent a group O—$(CH_2)_p$—$CH_3$, with p being an integer from 5 to 18.

Item 86. The process of any one of items 66 to 84, X represents H, and Y and Z represent a group O—$(CH_2)_p$—$CH_3$, with p being 7, 9, 11, 13, 15 or 17.

Item 87. The process of any one of items 66 to 84, wherein Y represents H, and X and Z represent a group O—$(CH_2)_p$—$CH_3$, with p being an integer from 5 to 18.

Item 88. The process of any one of items 66 to 84, wherein Y represents H, and X and Z represent a group O—$(CH_2)_p$—$CH_3$, with p being 7, 9, 11, 13, 15 or 17.

Item 89. The process of any one of items 66 to 84, wherein Y represents H, and X and Z represent a group O—$(CH_2)_p$—$CH_3$, with p=13.

Item 90. The process of any one of items 66 to 89, wherein

Ac-Sugar represents

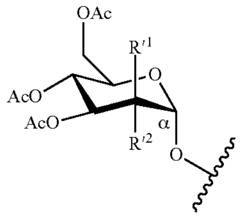

where R'1 represents OH and R'2 represents H, or where R'1 represents H and R'2 represents OH.

Item 91. The process of any one of items 66 to 89, wherein

Ac-Sugar represents

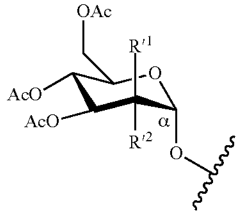

where R'1 represents OH and R'2 represents H.

Item 92. The process of any one of items 66 to 89, wherein Ac-Sugar represents

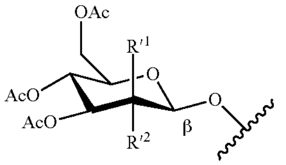

where R'[1] represents OH and R'[2] represents H, or where R'[1] represents H and R'[2] represents OH.

Item 93. The process of any one of items 66 to 80, wherein the synthetic glycolipid has the formula (Ia)

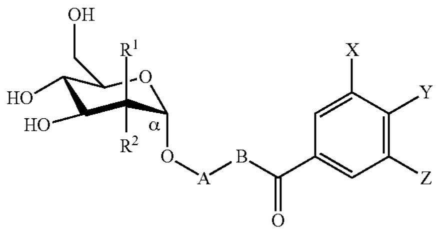

(Ia)

where

A represents $(CH_2)_n$ with n=6;

B represents NH;

$R^1$ represents OH and $R^2$ represents H;

Y represents H, and X and Z which are identical represent $O—(CH_2)_p—CH_3$, with p=13;

the compound of formula (V) is such that Ac-Sugar represents

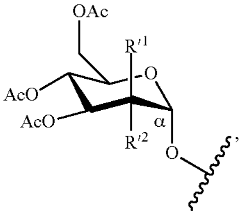

with

R'[1] represents OAc and R'[2] represents H; and the compound of formula (VI) is such that Y represents H, and X and Z which are identical represent $O—(CH_2)_p—CH_3$, with p=13.

EXAMPLES

Example 1: Materials and Methods

Reagents

Dynantin was prepared as previously described in Lewicky et al., 2020 and Lewicky et al., 2021, and was stored as a lyophilized powder at −20° C. The purity of Dynantin was determined to be ≥98% by RP-HPLC. The mannosylated glycoliposome $MG_{C12}$ was prepared as previously described in Lewicky et al., 2020. The purity of the mannosylated glycolipids was determined to be 95% as indicated by thin-layer chromatography and nuclear magnetic resonance spectroscopy. Stock solutions (50 μg/μL) of mannosylated liposome formed with 12d ($MG_{12d}$) or of $MG_{C12}$ were prepared by dissolving the compounds in (THF, HPLC grade, Fisher Scientific, Fairlawn NJ), and stored at −20° C. When required, less concentrated solutions were prepared by dilution of these stocks in THF.

Human Plasma Collection

Blood was collected from healthy volunteers in EDTA blood collection tubes (BD Vacutainer, Mississauga Canada). Plasma was collected after centrifugation at 900×g and 20° C. for 10 min with decreased deceleration, aliquoted, and stored at −80° C. All protocols were approved by the Research Ethics Board and the Biosafety Committee at Health Sciences North Research Institute (Protocol #18-061).

General Synthesis Methods

Reactions were carried out under argon atmosphere using commercially available HPLC grade. Commercially available reagents (Sigma Aldrich and Fisher Scientific, Canada) were used without further purification. N-Acetyl-D-galactosamine was provided from Rose Scientific Ltd. (Alberta, Canada). Progress of reactions was monitored by thin-layer chromatography using silica gel 60 $F_{254}$ coated plates (E. Merck). Flash chromatography was performed using ZEOprep™ silicagel 60 (40-63 m) from Canadian Life Science or FlasuPure™ system from Buchi. Detection was carried out under UV light or by spraying with 20% ethanolic sulfuric acid or molybdate or $KMnO_4$ solution followed by heating. NMR spectra were recorded on Bruker ULTRASHIELD™ 300 MHz and Bruker Avance™ III HD 400 and 600 MHz spectrometers. Proton and carbon chemical shifts (6) are reported in ppm relative to the chemical shift of residual $CHCl_3$, which was set at 7.27 ppm (H) and 77.00 ppm ($^{13}C$). Coupling constants (J) are reported in Hertz (Hz), and the following abbreviations are used for peak multiplicities: singlet (s), doublet (d), doublet of doublets (dd), doublet of doublet with equal coupling constants ($t_{ap}$), triplet (t), multiplet (m). Analysis and assignments were made using COSY (Correlated Spectroscopy) and HSQC (Heteronuclear Single Quantum Coherence) experiments. High-resolution mass spectra (HRMS) were measured with a LC-MS-TOF (Liquid Chromatography Mass Spectrometry Time of Flight) instrument from Thermo Scientific in positive and/or negative electrospray mode. Either protonated ions (M+H)+ or sodium adducts (M+Na)+ were used for empirical formula confirmation. LC method: Samples were injected (2 L) onto an PrePure™ C18 150×4.6 mm column with 5 m particles (BUCHI) using a Dionex™ Ultimate 3000 system (Thermo Scientific) with water (A) and acetonitrile (B), both containing 0.1% acetic acid, at a flow rate of 800 L/min at room temperature. The gradient started at 5% B, held for 0.5 min. It was increased to 15% B in 1 minutes, then to 27% B in 14.5 minutes, and then to 95% B in 4 minutes. The gradient was held at 95% B for 2 minutes, and it was then decreased to 5% B in 1 minute. Finally, the gradient was held at 5% B for 1 minute. The total time is 24 minutes. MS method: MS spectra were collected on an TSQ™ Quantum Access Max (Thermo Scientific) equipped with a HESI ion source in positive ion mode set at 4.5 kV source voltage, 320° C. source temperature. MS acquisition was from m/z 200-1000 in SCAN mode. The data was analyzed using Thermo XCalibur™ Qual Browser.

In Vitro Dopamine production

In vitro dopamine production was assessed as previously described in Lewicky et al., 2021. Male C57BL/6 mice (n=15) were sacrificed by $CO_2$ asphyxiation and cervical dislocation. Brains were immediately collected and dissected on ice ventral side-up by cutting along the midpoint of the anterior hypothalamic nucleus to obtain the approximate ⅓ section of brain constituting the striatum, and were gently homogenized on ice using a pellet mixer (VWR, Radnor, PA, USA). The tissues were then treated with either PBS (60 L, n=5) or Dynantin in PBS at a concentration of either 1 M (60 L, n=5) or 10 M (60 L, n=5). Samples were left for 90 min at 4° C. in the dark before being further homogenized in ice-cold absolute ethanol containing formic acid (0.1% v/v, 240 L) and 100 ng of a deuterated dopamine-D2 internal standard was added to the samples. The mixture was vigorously vortexed and then left on ice in the dark for 30 min and centrifuged at 10,000 rpm at 4° C. for 10 min. Supernatants (200 L) were carefully removed, replaced with an equal volume of acidified ethanol, and the mixture was vigorously vortexed and placed on ice for a further 30 min before being centrifuged. Combined supernatants were allowed to evaporate to dryness at room temperature in the dark overnight and reconstituted in $ddH_2O$ with formic acid (0.1% v/v, 100 L). Dopamine levels were determined by LC/MS.

Entrapment and Plasma Stability of MGs

Entrapment and plasma stability of MGs was assessed as previously described in Lewicky et al., 2020 and Lewicky et al., 2021. Briefly, glycoliposomal entrapment was done combining the stock Dynantin solution (12 L, 60 g) with $MG_{C12}$ (5:3 molar ratio of $MG_{C12}$:cholesterol) or $MG_{12d}$ (5:4 molar ratio of $MG_{12d}$:cholesterol) delivery systems (both in tert-butanol, 10 L total addition) in $ddH_2O$ to a final volume of 100 L and a final ratio of dynantin:MG of 1:5 (w/w) or in some cases 1:10 (w/w). Three sets of samples were each set up in triplicate, with the mixtures gently vortexed for 5 min. For one replicate of each sample, solids were immediately pelleted by centrifugation at 14,000 rpm and 20 C for 10 min, and supernatants carefully removed for analysis of the levels of free Dynantin that remained by RP-HPLC (10 L injections, in duplicate). The level of incorporated Dynantin is represented as the percentage of incorporated Dynantin relative to the amount determined in respective control samples comprising free Dynantin and tert-butanol (devoid of any glycolipid and cholesterol).

Dynantin stability incorporated into $MG_{C12}$ or $MG_{12d}$ was investigated using a modified version of the procedure above. The stock Dynantin solution (12 L, 60 g) was first combined with the glycolipids, with or without cholesterol (both in tert-butanol, 10 L total addition), and then thoroughly mixed before the addition of thawed human plasma (128 L). The final ratio of Dynantin:MG was 1:5 (w/w) or in some cases 1:10 (w/w). A control sample was also prepared by combining Dynantin with tert-butanol alone (10 L) and plasma (128 L). Samples were incubated at 37° C. in a heating mantle (VWR Scientific, Mississauga, ON, Canada) for varying lengths of time before being stored at −80° C. For HPLC analysis, samples were thawed, thoroughly mixed, diluted in MeOH (1/10) to destroy liposome particles, and solids pelleted by centrifugation at 10,000 rpm and 20° C. for 10 min. The supernatants were carefully removed for analysis (10 L injections, in duplicate). Stability is represented as the percentage of Dynantin remaining relative to the amount determined at T-zero.

In Vivo Dynantin Distribution and Dopamine Production

In vivo Dynantin distribution and dopamine production was assessed as previously described in Lewicky et al., 2021. Female BALB/C mice (5 per group) under isoflurane anesthesia (SomnoSuite, Kent Scientific, Torrington, CT, USA) were administered Dynantin (2.0 g total dose) intranasally (10 L, 5 L per nare dropwise by a micropipette) either alone in PBS or incorporated in either $MG_{C12}$ or $MG_{12d}$ (1:5 ratio of Dynantin:MG, w/w). Mice were sacrificed after 20 min under excess isoflurane via cardiac exsanguination and cutting of the diaphragm. For each mouse, serum was collected and lungs were removed and immediately stored on ice. Brains were immediately dissected and dopamine was extracted from striatal tissue and quantified by LC/MS, as previously described. The remaining brain tissue, sera, and lungs were kept frozen at −80° C. for extraction and analysis of Dynantin levels as described in Lewicky et al., 2020. Dynantin levels are represented as both a total recovery and a concentration normalized to the weight or volume of each sample.

Statistical Analyses

Statistical analyses in the form of either a one-way ANOVA with a Tukey HSD or Mann-Whitney t-test were performed using GraphPad™ Prism™ 5. The criterion for significance was $p<0.05$.

Evaluation of Hemolysis

Red blood cells (RBC) were isolated from the blood of three healthy volunteers by Ficoll-Paque (GE Healthcare, Uppsala Sweden) density gradient separation (approved by the Research Ethics Board and the Biosafety Committee at Health Sciences North Research Institute, protocol #18-061). Isolated RBC were diluted to 5% (v/v) in PBS containing various concentrations of 12d (12.5-100 μg/mL). PBS alone was used as a 0% hemolysis control and ACK lysing buffer (Lonza, Walkersville MD) was used as a 100% hemolysis control. Hemolysis was measured according to D. Guggi, et al. Int. J Pharm. 278 (2004) 353-360. RBC were platted in a 96 multi-well plate (200 μL) and incubated at 37° C. for 1 hour, after which the plate was centrifuged at 300 g for 10 minutes. 100 μL of the supernatants was transferred to a new plate and absorbance was read at 570 nm with a Synergy H4 Hybrid Microplate Reader (BioTek, Winooski VT).

Cell Culture and Nile Red Uptake

Murine dendritic cells JAWSII (ATCC® CRL-11904™) were grown in RPMI-1640 medium (HyClone, Logan UT) supplemented with 8% FBS (Gibco, Grand Island NY), 100 units/ml penicillin/streptomycin (HyClone, Logan UT) and 5 ng/mL of GM-CSF (Invitrogen, Frederick MD) at 37° C. and 5% $CO_2$. Once confluent, cells were collected using 0.25% Trypsin-EDTA (Gibco, Grand Island NY). Murine macrophage cells J774A.1 (ATCC® TIB-67™) and human malignant cells HeLa (ATCC® CCL-2™; Cederlane, Burlington, ON, Canada) were grown Dulbecco's minimal essential medium (DMEM) high glucose (HyClone, Logan, UT) supplemented with 10% FBS and 100 units/ml penicillin/streptomycin at 37° C. and 5% $CO_2$. Once confluent, cells were collected using a cell scraper. Viability was assessed prior to experiments by Trypan Blue (Gibco, Grand Island NY) exclusion where the viability was >90%. Cells were seeded at $3\times10^5$ cells in 300 μL in a 96 multi-well plate and left untreated or were treated with 10 μg/mL of empty liposomes $MG_{12d}$ or $MG_{C12}$, 1 μg/mL of Nile Red (Sigma, St-Louis MO), or 1 μg/mL of Nile Red encapsulated in 10 μg/mL of $MG_{12d}$ or $MG_{C12}$. Cells were collected after 1 hour at 37° C., washed once with 300 μL of PBS, and re-suspended in 300 μL of PBS. Mean fluorescence intensity was analysed using the Cytomics FC-500 flow cytometer (Beckman Coulter, Fullerton CA) using the FL3 channel where 104 events were measured. Data was analyzed using the CXP Analysis Software. Nile Red was visualized using an inverted Olympus IX73 microscope and excited with the TRITC filter at 540 nm for 2 s or phase contrast for <59 ms and merged for the final image.

Differential interference contrast and confocal microscopy images were taken using a Nikon A1R confocal microscope with 100× oil CFI NA 1.45 Plan Apochromat, objective (fluorescence) and 63× oil immersion objective upon differential interference contrast illumination (DIC). All images were captured with a pinhole size of 59.1 μm, with a calibration of 0.12 μm/pixel (radial resolution of 0.20 μm) and a Z-step of 0.15 μm. Images were captured using NIS-element software (Nikon) and Leica LAS AF imaging software.

Cytokine Analysis

The cytokine profile was assessed in peripheral blood mononuclear cells (PBMCs) isolated by Ficoll-Paque (GE Healthcare, Uppsala, Sweden) density gradient from the whole blood of three immunocompetent healthy individuals (in accordance to HSN REB #18-061). Immediately after extraction, PBMCs were seeded at 106 cells/mL in RPMI-1640 medium (HyClone, Logan UT) supplemented with 10% FBS (Gibco, Grand Island NY) and 100 units/mL of penicillin/streptomycin (HyClone, Logan UT). PBMCs were left untreated or treated with $MG_{12d}$ (10 μg/mL) for 48 hours before analysing the supernatants for IL-12p40, IL-12p70, IL-10, IL-2, TNFα and IFNγ by ELISA. ELISA kits were purchased from R&D Systems (Minneapolis MN) and ran according to the manufacturer's protocols.

Dynamic Light Scattering and Confocal Microscopy

The self-assembly of the glycoliposomes into vesicles and liposomes involved the injection method of their solution in a water miscible solvent such as ethanol or tetrahydrofuran (THF) into water or buffer. This methodology has been shown to be efficient for the self assembly of previously described amphiphilic mannosylated neoglycolipids into monodisperse vesicles (Percec, V., et al. *J Am. Chem. Soc.*, (2013), 135, 9055-9077). The resulting assemblies were first analyzed by dynamic light scattering (DLS) for size, polydispersity (PDI), and stability in time. For liposome size determination, solutions of the glycolipids (3.5 mg) in THF (1.1 mL) were then diluted in distilled water (2.2 mL) to provide final concentrations of 1.06 mg/mL. Particle size distributions were measured in water using a Zetasizer® Nano S90 from Malvern Instruments (UK) equipped with 4 mW He—Ne laser 633 nm and avalanche photodiode positioned at 90° to the beam and temperature-controlled cuvette holder. Instrument parameters were determined automatically along with measurement times. Experiments were performed in triplicate at 25° C.

Crosslinking studies were carried out in 1 mol/L phosphate buffered saline (PBS) for the plant lectin Concanavalin A (Con A) (Sigma-Aldrich) known to bind multivalent mannosylated glycoconjugates. For this, ConA (0.5 mg) was dissolved in PBS buffer (0.5 mL); aliquots of 0.5 mL (~0.5 mg) were taken from the original liposomal solutions described above and the size of the steadily increasing cross-linked aggregates were monitored as a function of time.

Differential interference contrast and confocal microscopy images were taken using a Nikon A1R confocal microscope with 100× oil CFI NA 1.45 Plan Apochromat, objective (fluorescence) and 63× oil immersion objective upon differential interference contrast illumination (DIC). All images were captured with a pinhole size of 59.1 μm, with a calibration of 0.12 m/pixel (radial resolution of 0.20 μm) and a Z-step of 0.15 μm. Images were captured using NIS-element software (Nikon) and Leica LAS AF imaging software.

Example 2: Enhanced CNS Delivery by Mannosylated Glycoliposomes (MG)

Dynantin is a potent and selective dynorphin peptide analogue antagonist of the kappa opioid receptor (KOR), which blocks the activity of endogenous dynorphin, ultimately resulting in increased dopamine levels in the striatum that are associated with a unique combination of both antidepressant and antianxiogenic effects (Brujinzeel, A. W., 2009). Delivery of Dyantin into the brain, as well as increase dopamine levels, was previously shown to be enhanced by incorporation of Dynantin into the mannosylated glycoliposome C12 ($MG_{C12}$) formed from the glycolipid $GL_{C12}$ of the formula below (Lewicky et al., 2020).

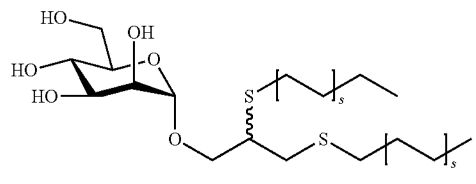

$GL_{C12}$ used to prepare the glycoliposome $MG_{C12}$

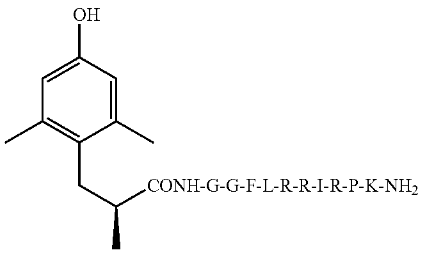

Dynantin

As described herein, a novel mannosylated glycoliposome, $MG_{12d}$, comprising the synthetic glycolipid 12d, was developed and assessed its ability to efficiently deliver Dynantin into the CNS and enhance dopamine production.

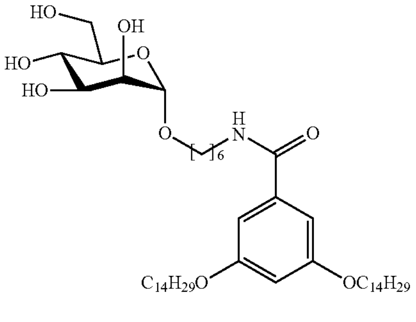

Glycolipid 12d used to prepare the glycoliposome, $MG_{12d}$

Figure 1:
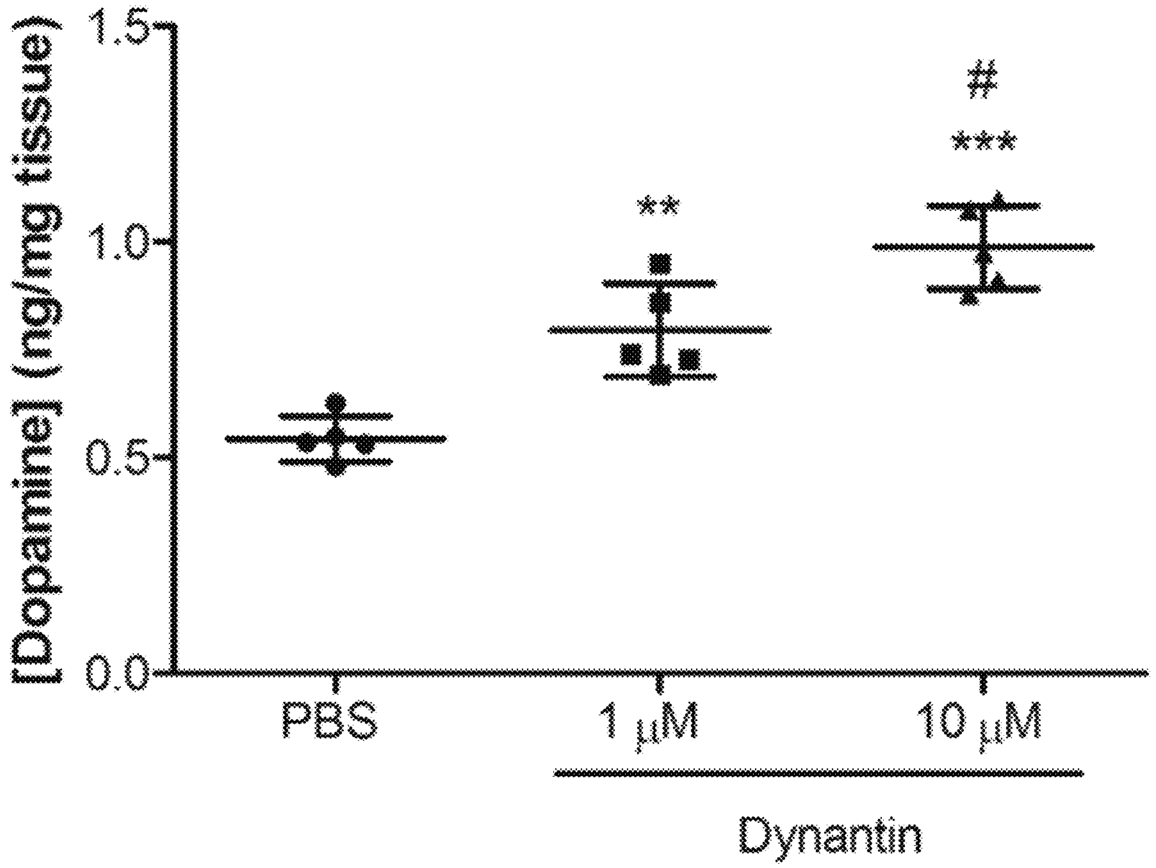
FIG. 1 shows the results of in vitro dopamine production by the striatal tissue from the brains of mice in the presence of Dynantin (1 μM and 10 μM) as compared to PBS. Data are shown as the average SD of the 5-6 mice in each group. *p<0.001 and p<0.01 as compared to the PBS treatment group, #p<0.05 as compared to the 1 μM Dynantin treatment group.

First, as a proof-of-concept, in vitro dopamine production by Dynantin in ex vivo brain striatal tissue was assessed. Striatal tissue from brains of mice were prepared as described in Example 1, and were treated with either PBS, 1 μM, or 10 μM of Dynantin for 90 minutes at 4° C. in the dark. Dopamine was then extract and quantified by LC/MS in the presence of 0.1% formic acid. As shown in FIG. 1, dopamine levels were significantly elevated upon treatment with increasing concentrations of Dynantin. The levels of striatal dopamine measured in the PBS treated control group were found to be within the normal range of baseline levels reported in the literature for mice, indicating that the dissection and extraction processes did not have any significant effect on dopamine production.

Figure 2A:
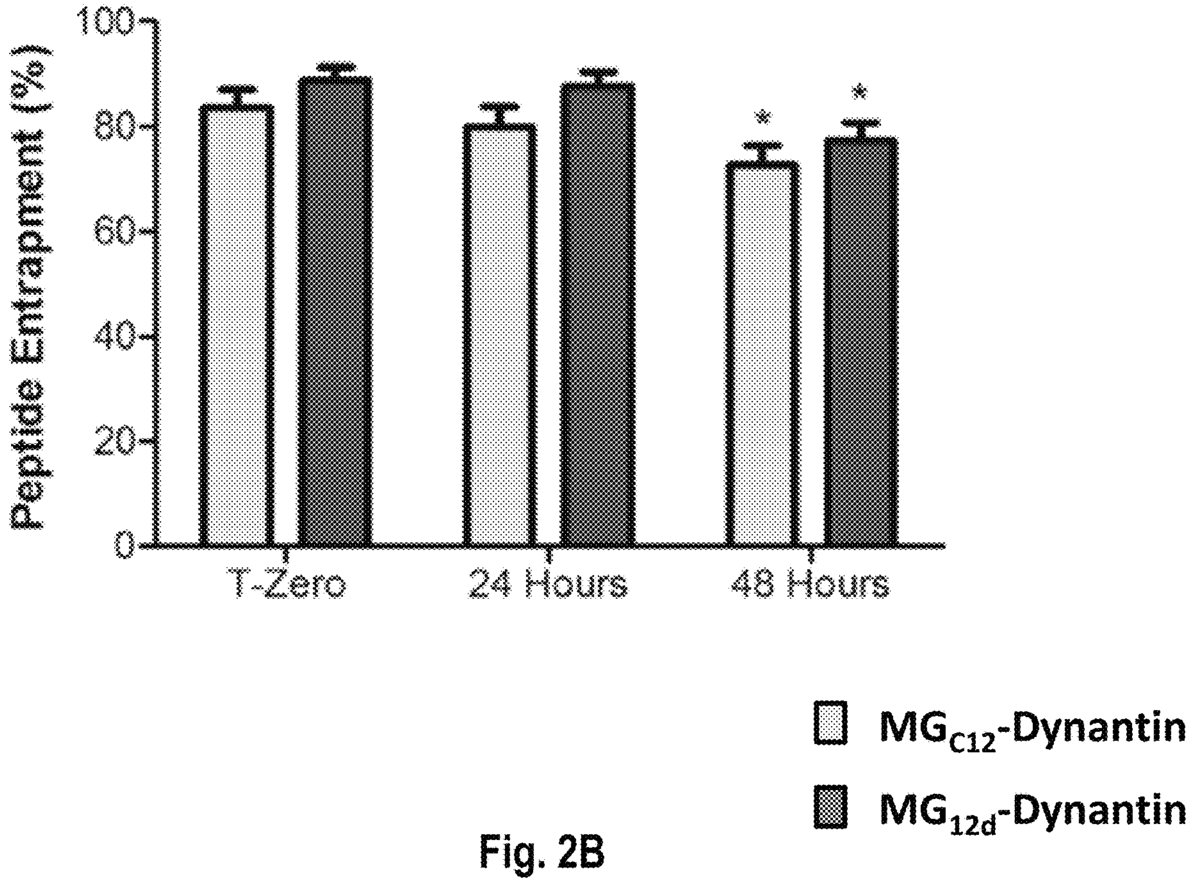
FIG. 2A shows the results at a final ratio of dynantin:MG of 1:5 (w/w). Stability results were calculated relative to the quantities determined at time point zero.
Figure 2B:
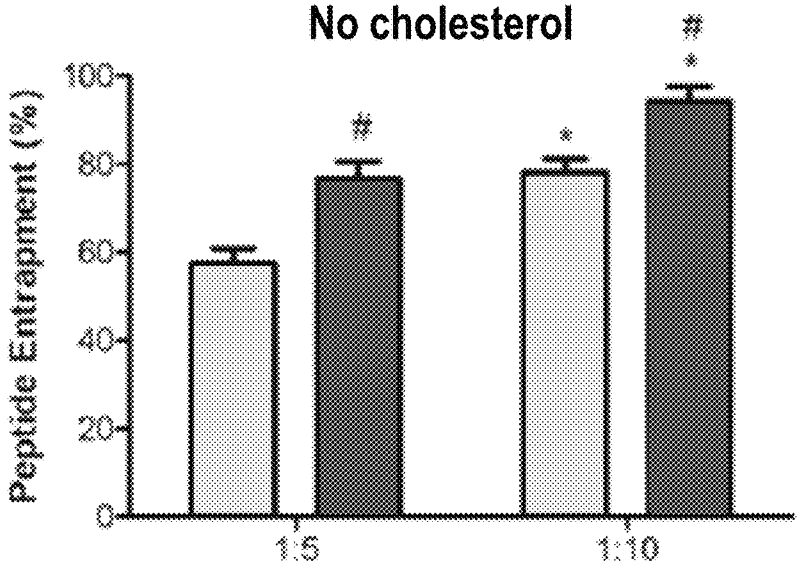
FIGS. 2B and 2D show entrapment efficacy and plasma stability results, respectively, in MG formulations in the absence of cholesterol. All data are shown as the average SEM of three separate experiments. *p<0.05 as compared to T-zero; ^^^p<0.001 as compared to the respective formulation at 24 h; #p<0.05 as compared to the DS1 formulation at the respective time point.
Figure 2C:
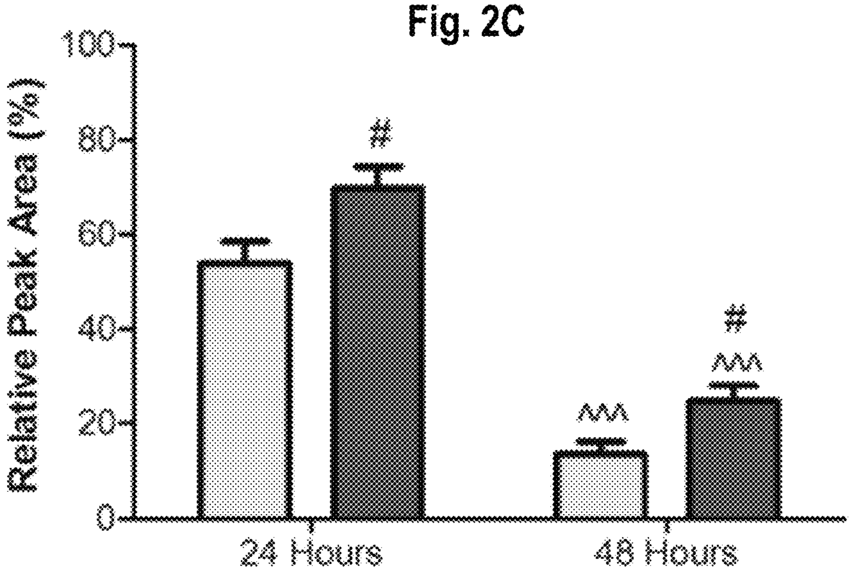
FIG. 2 shows the results of the entrapment efficacity (FIGS. 2A and 2B) and plasma stability (FIGS. 2C and 2D) of mannosylated glycoliposomes (MG), $MG_{C12}$ and $MG_{12d}$, incorporated with Dynantin. Entrapment results are shown as the percentage of entrapped Dynantin relative the amount determined in control samples with Dynantin alone (unincorporated into MG).
Figure 2D:
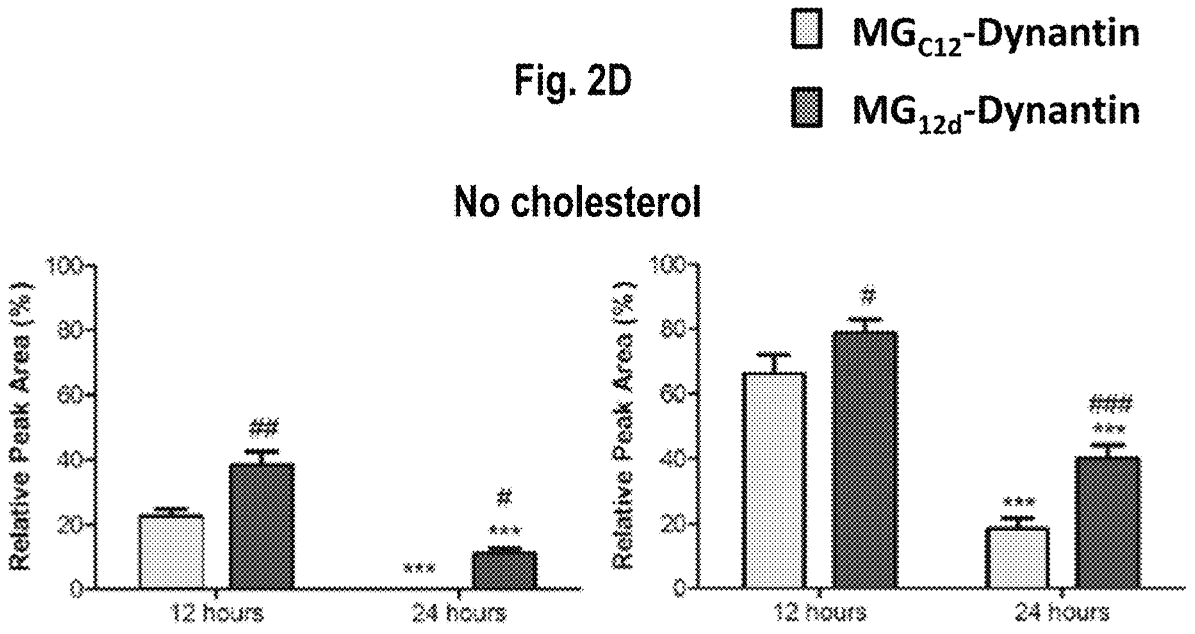

Next, the ability of $MG_{12d}$ to incorporate Dynantin and protect it from proteolytic degradation in the presence of human plasma was evaluated. Similar to $MG_{C12}$ (Lewicky et al., 2020), $MG_{12d}$ contains glycolipids and cholesterol, and was incorporated with Dynantin at a final ratio of dynantin: MG of 1:5 (w/w). As shown in FIGS. 2A and 2B, both $MG_{C12}$ and $MG_{12d}$ provided a high degree of initial entrapment (84%±4% for $MG_{C12}$ and 88%±3% for $MG_{12d}$) that was maintained after 24 h (80%±4% for $MG_{C12}$ and 87%±3% for $MG_{12d}$). After 48 h, Dynantin levels began to decrease (73%±4% for $MG_{C12}$ and 78%±3% for $MG_{12d}$), however, $MG_{12d}$ was consistently more efficient at retaining Dynantin as compared to $MG_{C12}$. Furthermore, both $MG_{C12}$ and $MG_{12d}$ adequately protected Dynantin from proteolytic enzymes in the presence of human plasma (FIGS. 2C and 2D). Interestingly, $MG_{12d}$ was found to have greater plasma stability. Similar results for peptide entrapment and plasma stability were seen at a final ratios of dynantin:MG of 1:5 and 1:10 (w/w), in the absence of cholesterol (FIGS. 2B and 2D). These results suggest that particles formed with the $MG_{12d}$ are more resistant to degradation.

Figure 3A:
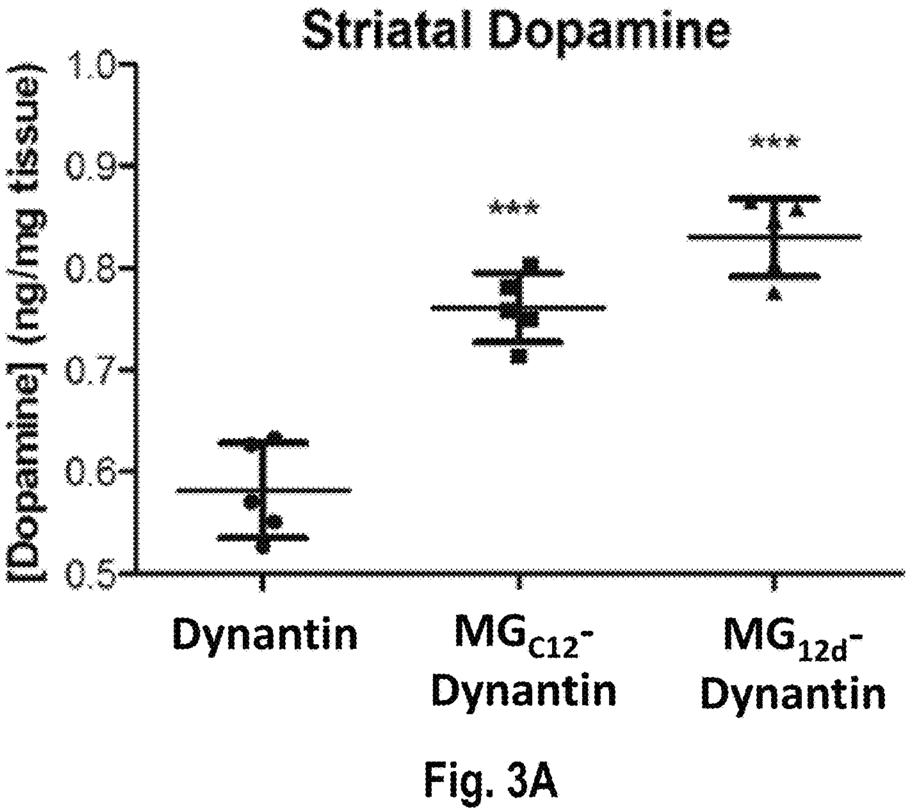
FIG. 3A shows dopamine production by striatal tissue from brains of treated mice. Dynantin was then extracted and quantified from the remaining brain tissue (B), sera (C), and lungs (D) after lyophilisation and levels of Dynantin quantified by RP-HPLC in the presence of 0.1% trifluoroacetic acid and detection by absorbance. Data are shown as the average SD of the 5 mice in each group. ***p<0.001 as compared to Dynantin alone.
Figure 3B:
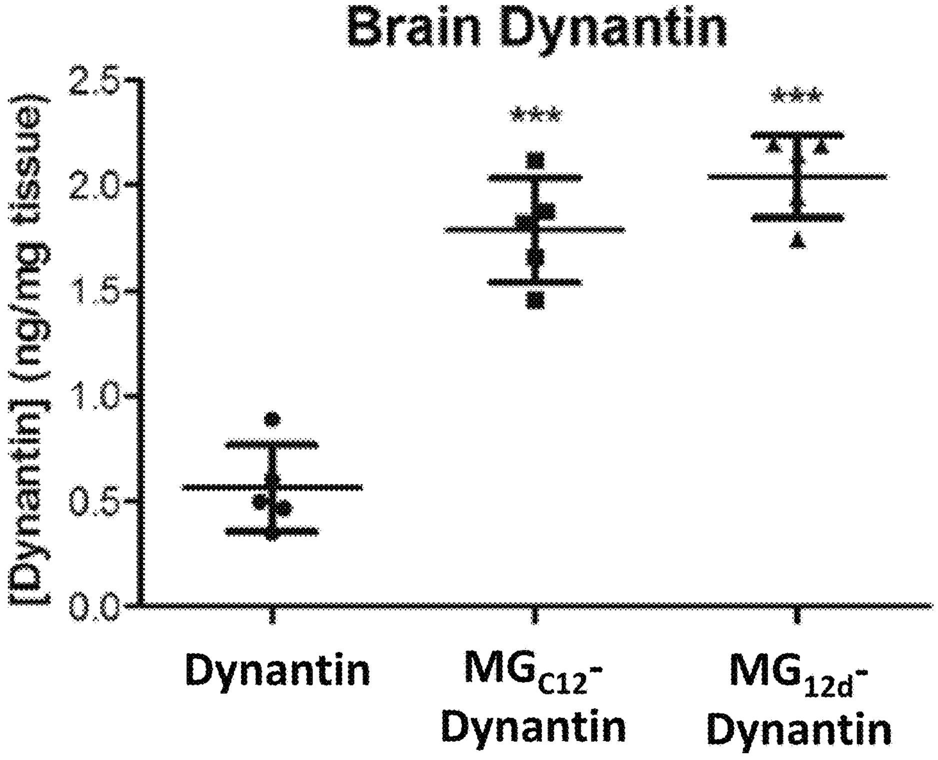
FIG. 3 shows the results of the Dynantin distribution and dopamine modulation in vivo upon intranasal treatment with $MG_{C12}$ or $MG_{12d}$, incorporated with Dynantin, or with Dynantine alone.
Figure 3C:
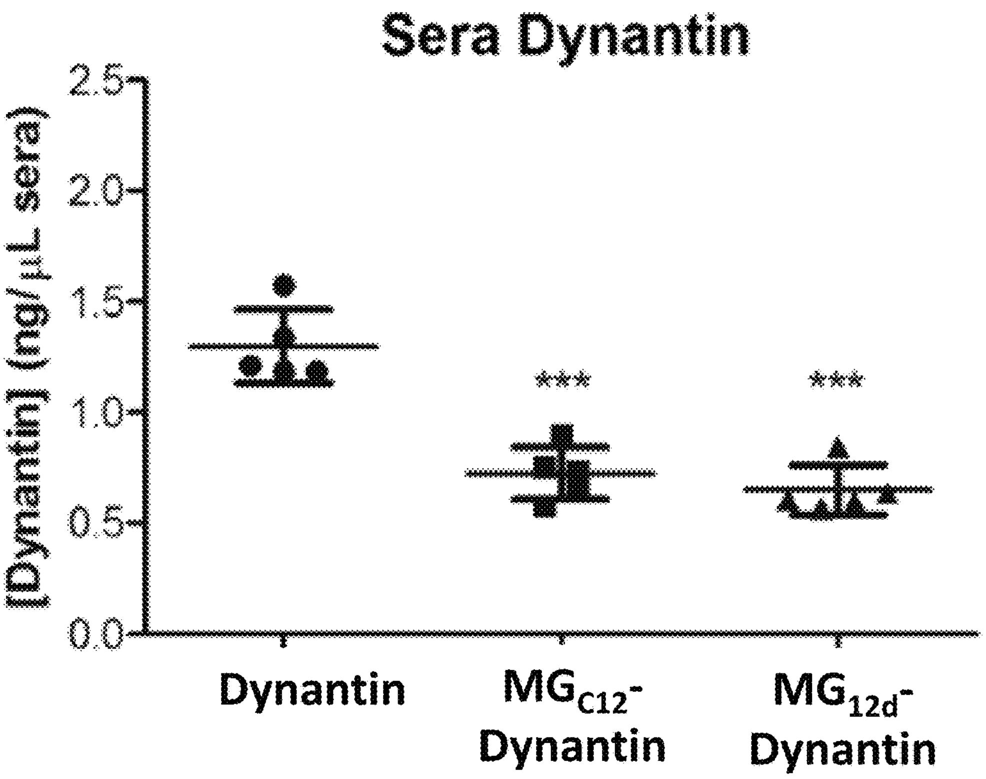
Figure 3D:
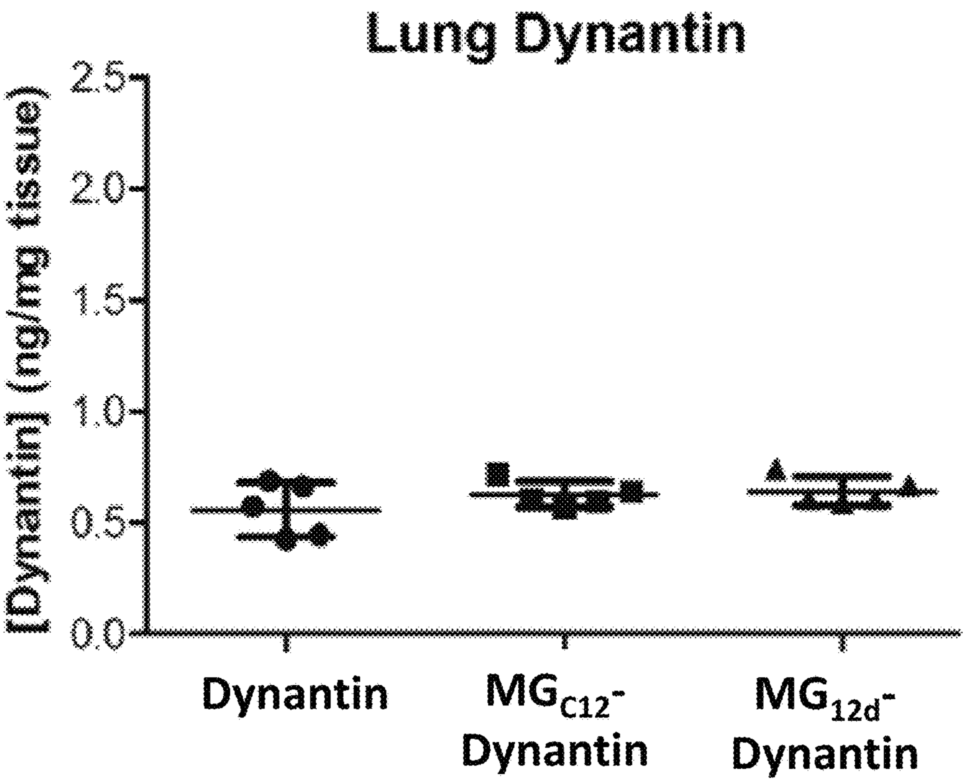

The ability of $MG_{12d}$ to deliver Dynantin into the brain and enhance dopamine production in vivo was next evaluated. BALB/c were intranasally administer with Dynantin (2 μg) either alone or incorporated within $MG_{C12}$ or $MG_{12d}$. Mice were sacrificed 20 minutes later and blood (sera), lungs and brains were collected. First, striatum tissue from the brains of treated mice were assessed for dopamine levels. As shown in FIG. 3A, dopamine levels were significantly enhanced upon treatment with Dynantin incorporated within $MG_{C12}$ (0.76±0.04 ng/mg) or $MG_{12d}$ (0.83±0.05 ng/mg), as compared to Dynantin alone (0.58±0.05 ng/mg). In addition, $MG_{12d}$ was shown to be more efficient than $MG_{C12}$ at inducing dopamine levels in the brain. Furthermore, Dynantin levels and distribution was assessed in the brain, lung, and sera (blood) of treated mice. As shown in FIG. 3B, while there were detectable levels of Dynantin in the brains of the mice that were administered Dynantin alone, significantly higher levels were found in the brains of the mice treated with $MG_{C12}$-Dynantin (1.79±0.25 ng/mg), and even higher in the brains of the mice treated with $MG_{12d}$-Dynantin (2.04±0.20 ng/mg). In the sera, the opposite was seen whereby lower levels of Dynantin was observed in mice treated with $MG_{C12}$- or $MG_{12d}$-Dynantin, as compared to Dynantin alone (FIG. 3C). Finally, similar levels of Dyantin were observed in the lung in all treated group (FIG. 3D). In vivo quantification and distribution of Dynantin as the percentage of total dose recovered from organ and sera samples is summarized in Table 1 below. Interestingly, $MG_{C12}$ and $MG_{12d}$ improve the overall distribution of the peptide into the brain by approximately 3.0 and 3.5 times, respectively.

TABLE 1

In vivo quantification and distribution of Dynantin

| | Brain (%) | Sera (%) | Lung (%) |
|---|---|---|---|
| Dynantin | 8.15 ± 3.06 | 21.66 ± 3.99 | 4.93 ± 0.89 |
| $MG_{C12}$-Dynantin | 24.89 ± 4.39 | 14.03 ± 3.02 | 5.05 ± 0.98 |
| $MG_{12d}$-Dynantin | 28.03 ± 3.51 | 11.68 ± 1.18 | 5.50 ± 0.53 |

Data shown are average SD of the 5 mice in each group

These data clearly demonstrate the brain targeting ability offered by the mannosylation of the glycoliposomes, in that there is significantly less peptide remaining in the systemic circulation. Taken together, the results clearly highlight the ability of MGs, particularly $MG_{12d}$, to improve both the delivery and activity of dynantin in the brain, where the resulting higher levels of the peptide translate into significant positive modulations of striatal dopamine levels.

Example 3: Synthesis of the Synthetic Glycolipids

General Procedure for Derivatives Methyl Dihydroxybenzoates (A) (2a-2b)

FIG. 4: To a solution of dihydroxybenzoic acid (1a-1b) in dry methanol, was added (0.15 eq.) Conc. $H_2SO_4$. The reaction mixture was heated 70° C. for 7 h. The solution was evaporated under reduced pressure. The solid was treated carefully with a saturated $NaHCO_3$ aqueous solution, and the product was extracted with EtOAc. The organic phase was washed with water and brine and finally evaporated to afford white solid of final products. The product was used for the next reactions without further purification.

Methyl 3,5-dihydroxybenzoate (2a) (Percec et al., 2013)

3,5-dihydroxybenzoic acid (1a) (5.00 g, 32.4 mmol, 1.0 eq.), methanol (40 mL, 988 mmol, 30.5 eq.) and sulfuric acid (0.25 mL, 4.80 mmol, 0.15 eq.) was heated at 70° C. for 7 h. The reaction was cooled to room temperature and the methanol was removed. The solid was treated carefully with a saturated aqueous $NaHCO_3$ solution, and the product was extracted with ethyl acetate. The organic phase was washed with water and brine and finally evaporated to give methyl 3,5-dihydroxybenzoate (2a) as a white solid (5.00 g, 92%). The product was used for the next reaction without further purification. $^1H$ NMR (300 MHz, DMSO-$d_6$) δ 9.66 (s, 2H, OH), 6.85 (d, J=3 Hz, 2H, H-arom), 6.48 (dd, J=3 Hz, 1H, H-arm), 3.83 (s, 3H, $OCH_3$). $^{13}C$ NMR (75 MHz, DMSO-$d_6$) δ 166.4 (CO), 158.7 ($C_{arom}$), 131.5 ($C_{arom}$), 107.3 (2× $CH_{arom}$), 52.1 ($OCH_3$).

Methyl 3,4-dihydroxybenzoate (2b)

Slightly grey-colored solid (2.27 g, 13.5 mmol, 83%). $^1H$-NMR (300 MHz, DMSO-$d_6$) δ 7.34 (d, J=2.1 Hz, 1H), 7.30 (dd, J=8.2, 2.1 Hz, 1H), 6.79 (d, J=8.2 Hz, 1H), 3.75 (s, 3H). $^{13}C$-NMR (75 MHz, DMSO-$d_6$) δ 167.7, 151.7, 146.3, 123.2, 121.8, 117.5, 116.6, 53.0.

General Procedure for Derivatives Methyl bis (alkyloxy) benzoates (B) (3a-31)

To a mixture of Methyl dihydroxybenzoate (2a-2b) (1.0 eq.), $K_2CO_3$ (2.7 eq.) and KI (0.1 eq.) in DMF was added 1-bromoalkane (2.4 eq.). The solution mixture was stirred at 90° C. for 24 hr. It was cooled and diluted with DCM (100 ml). The solution was washed with water twice and brine then dried over $Na_2SO_4$. The solvent was removed, and a solid residue was obtained. The solid was filtered and washed with methanol and dried. The crude product was further purified by passing through a column of silica gel (by gradient, 100% hexanes to 4% EtOAc in hexanes as eluents) to afford desire compound as white solids (51%-91%).

Methyl 3,5-bis(octyloxy)benzoate (3a)

White solid (1.19 g, 30.0 mmol, 51%). $^1H$-NMR (300 MHz, $CDCl_3$) δ 7.16 (s, 2H, $H_{arom}$), 6.63 (s, 1H, $H_{arom}$), 3.96 (t, J=6 Hz, 4H, $CH_2$), 3.89 (s, 3H, $OCH_3$), 1.77 (m, 4H, $CH_2$), 1.45-1.29 (m, 20H, $CH_2$), 0.89 (t, J=6 Hz, 6H, $2\times CH_3$). $^{13}$C-NMR (75 MHz, $CDCl_3$) δ 167.1 (CO); 160.3 ($C_{arom}$), 131.9 ($C_{arom}$), 107.7 ($CH_{arom}$); 106.7 ($CH_{arom}$), 68.4, 52.3, 31.9, 29.5, 29.4, 29.3, 26.2, 22.8, 14.3 ($OCH_3$).

Methyl 3,5-bis(decyloxy)benzoate (3b)

White solid (2.00 g, 75%). $^1$H-NMR (300 MHz, $CDCl_3$) δ 7.16 (s, 2H, $H_{arom}$), 6.63 (s, 1H, $H_{arom}$), 3.97 (t, J=6 Hz, 4H, $CH_2$), 3.90 (s, 3H, $OCH_3$), 1.77 (m, 4H, $CH_2$), 1.45-1.27 (m, 28H, $CH_2$), 0.88 (t, J=6 Hz, 6H, $2\times CH_3$). $^{13}$C-NMR (75 MHz, $CDCl_3$) δ 167.1 (CO), 160.3 ($C_{arom}$), 131.9 ($C_{arom}$), 107.7 ($CH_{arom}$), 106.7 ($CH_{arom}$), 68.4, 52.3, 32.0, 29.7, 29.5, 29.3, 26.1, 22.8, 14.2 ($OCH_3$).

Methyl 3,5-bis(dodecyloxy)benzoate (3c)

White solid (2.37 mg, 4.70 mmol, 78%). $^1$H-NMR (300 MHz, $CDCl_3$) δ 7.15 (s, 2H, $H_{arom}$), 6.63 (s, 1H, $H_{arom}$), 3.96 (t, J=6 Hz, 4H, $CH_2$), 3.89 (s, 3H, $OCH_3$), 1.77 (m, 4H, $CH_2$), 1.45-1.27 (m, 36H, $CH_2$), 0.88 (t, J=6 Hz, 6H, $2\times CH_3$). $^{13}$C-NMR (75 MHz, $CDCl_3$) δ 167.1 (CO), 160.3 ($C_{arom}$), 132.0 ($C_{arom}$), 107.8 ($CH_{arom}$), 106.7 ($CH_{arom}$), 68.5, 52.3, 32.1, 29.8, 29.7, 29.5, 29.3, 26.2, 22.8, 14.3 ($OCH_3$).

Methyl 3,5-bis(tetradecyloxy)benzoate (3d) (Diroll et al., 2016)

To a stirred solution of methyl 3,5-dihydroxybenzoate (2a) (1.00 g, 5.95 mmol, 1.0 eq.) and 1-bromotetradecane (3.96 g, 14.28 mmol, 2.4 eq.) in DMF (25 mL) was added $K_2CO_3$ (2.22 g, 16.1 mmol, 2.7 eq.) and KI (69 mg, 417 nmol, 0.07 eq.) and the resulting mixture stirred at 90° C. for 12 h. The reaction mixture was cooled, diluted with $CHCl_3$, washed with $H_2O$ (100 mL) and brine (100 mL), dried over anhydrous $Na_2SO_4$, filtered and the filtrate concentrated under reduced pressure. To the residue was added MeOH to induce the precipitation. The precipitate was collected by filtration and dried to obtain methyl 3,5-bis(tetradecyloxy) benzoate (3d) as a white solid (2.44 g, 72%). $^1$H NMR (300 MHz, $CDCl_3$) δ 7.16 (s, 2H, $H_{arom}$), 6.63 (s, 1H, $H_{arom}$), 3.96 (t, J=6 Hz, 4H, $CH_2$), 3.89 (s, 3H, $OCH_3$), 1.77 (m, 4H, $CH_2$), 1.44-1.26 (m, 44H, $CH_2$), 0.88 (m, 6H, $2\times CH_3$). $^{13}$C NMR (75 MHz, $CDCl_3$) δ 167.1 (CO), 160.3 ($C_{arom}$), 131.9 ($C_{arom}$), 107.7 ($CH_{arom}$), 106.7 ($CH_{arom}$), 68.4, 52.3, 32.1, 29.8, 29.7, 29.5, 29.3, 26.2, 22.8, 14.3 ($OCH_3$).

Methyl 3,5-bis(hexadecyloxy)benzoate (3e)

White solid (2.68 g, 73%). $^1$H-NMR (300 MHz, $CDCl_3$) δ 7.15 (s, 2H, $H_{arom}$), 6.63 (s, 1H, $H_{arom}$), 3.96 (t, J=6 Hz, 4H, $CH_2$), 3.90 (s, 3H, $OCH_3$), 1.77 (m, 4H, $CH_2$), 1.45-1.26 (m, 52H, $CH_2$), 0.88 (t, J=6 Hz, 6H, $2\times CH_3$). $^{13}$C-NMR (75 MHz, $CDCl_3$) δ 167.1 (CO), 160.3 ($C_{arom}$), 131.9 ($C_{arom}$), 107.8 ($CH_{arom}$), 106.7 ($CH_{arom}$), 68.4, 52.3, 32.1, 29.9, 29.8, 29.7, 29.5, 29.3, 26.2, 22.8, 14.3 ($OCH_3$).

Methyl 3,5-bis(octadecyloxy)benzoate (3j)

White solid (2.49 g, 78%). $^1$H-NMR (300 MHz, $CDCl_3$) δ 7.16 (s, 2H, $H_{arom}$), 6.63 (s, 1H, $H_{arom}$), 3.96 (t, J=6 Hz, 4H, $CH_2$), 3.89 (s, 3H, $OCH_3$), 1.77 (m, 4H, $CH_2$), 1.44-1.26 (m, 60H, $CH_2$), 0.88 (t, J=6 Hz, 6H, $2\times CH_3$). $^{13}$C-NMR (75 MHz, $CDCl_3$) δ 167.1 (CO), 160.3 ($C_{arom}$), 131.9 ($C_{arom}$), 107.8 ($CH_{arom}$), 106.7 ($CH_{arom}$), 68.4, 52.3, 32.1, 29.9, 29.8, 29.7, 29.5, 29.3, 26.2, 22.9, 14.3 ($OCH_3$).

General Procedure for Hydrolysis of Methyl Ester (C) (4a-41)

The mixture solution of Methyl bis(alkyloxyl)benzoate (3a-31) (1.0 eq.) with KOH (4.0 eq.) in water and ethanol (7:1, v/v) were refluxed for 4 h. Then reaction mixture was cooled to room temperature and concentrated. 1N Hydrochloric acid solution was then added carefully until pH=1 followed by extraction with dichloromethane. The combined organic solvents were separated, dried over MgSO4 and evaporated to yield bis (alkylooxyl) benzoic acid.

3,5-bis(octyloxy)benzoic acid (4a)

White solid (855 mg, 87%). $^1$H-NMR (300 MHz, $CDCl_3$) δ 7.23 (s, 2H, $H_{arom}$), 6.69 (s, 1H, $H_{arom}$), 3.98 (t, J=6 Hz, 4H, $CH_2$), 1.79 (m, 4H, $CH_2$), 1.46-1.25 (m, 20H, $CH_2$), 0.89 (t, J=6 Hz, 6H, $2\times CH_3$). $^{13}$C-NMR (75 MHz, $CDCl_3$) δ 172.5 (COOH); 160.4 ($C_{arom}$), 131.1 ($C_{arom}$), 108.3 ($CH_{arom}$), 107.6 ($CH_{arom}$), 68.5, 32.0, 29.5, 29.4, 29.3, 26.2, 22.9, 14.2 ($CH_3$).

3,5-bis(decyloxy)benzoic acid (4b)

White solid (1.31 g, 90%). $^1$H-NMR (300 MHz, $CDCl_3$) δ 7.22 (s, 2H, $H_{arom}$), 6.69 (s, 1H, $H_{arom}$), 3.98 (t, J=6 Hz, 4H, $CH_2$), 1.79 (m, 4H, $CH_2$), 1.48-1.27 (m, 28H, $CH_2$), 0.89 (t, J=6 Hz, 6H, $2\times CH_3$). $^{13}$C-NMR (75 MHz, $CDCl_3$) δ 172.4 ($C_{COOH}$), 160.4 ($C_{arom}$), 131.1 ($C_{arom}$), 108.3 ($CH_{arom}$), 107.6 ($CH_{arom}$), 68.5, 32.1, 29.7, 29.5, 29.3, 26.2, 22.8, 14.3 ($CH_3$).

3,5-bis(dodecyloxy)benzoic acid (4c)

White solid (2.08 g, 97%). $^1$H-NMR (300 MHz, $CDCl_3$) δ 7.22 (s, 2H, $H_1$, $H_{arom}$), 6.69 (s, 1H, $H_{arom}$), 3.98 (t, J=6 Hz, 4H, $CH_2$), 1.79 (m, 4H, $CH_2$), 1.46-1.27 (m, 36H, $CH_2$), 0.88 (t, J=6 Hz, 6H, $2\times CH_3$). $^{13}$C-NMR (75 MHz, $CDCl_3$) δ 172.4 ($C_{COOH}$), 160.4 ($C_{arom}$), 131.1 ($C_{arom}$), 108.3 ($CH_{arom}$), 107.6 ($CH_{arom}$), 68.5, 32.1, 29.8, 29.7, 29.5, 29.3, 26.2, 22.9, 14.3 ($CH_3$).

3,5-bis(tetradecyloxy)benzoic acid (4d)

Methyl 3,5-bis(tetradecyloxy)benzoate (3d) (1.50 g, 2.67 mmol, 1.0 eq.), KOH (599 mg, 10.68 mmol, 4.0 eq.) in water (9 mL) and ethanol (60 mL) were refluxed for 4 h. Then reaction mixture was cooled to room temperature and concentrated. 1N Hydrochloric acid solution was then added carefully until pH=1 followed by extraction with dichloromethane. The combined organic solvents were separated, dried over MgSO4 and evaporated to yield 3,5-bis(tetradecyloxy)benzoic acid (4d) as a white solid (1.03 g, 69%). $^1$H NMR (300 MHz, $CDCl_3$) δ 7.22 (s, 2H, $H_{ar}$), 6.69 (s, 1H, $H_{ar}$), 3.98 (t, J=6 Hz, 4H, $CH_2$), 1.79 (m, 4H, $CH_2$), 1.46-1.26 (m, 44H, $CH_2$), 0.88 (m, 6H, $2\times CH_3$). $^{13}$C NMR (75 MHz, $CDCl_3$) δ 172.4 (COOH), 160.4 ($CH_{ar}$), 131.1 ($CH_{ar}$), 108.3 ($CH_{ar}$), 107.6 ($CH_{ar}$), 68.5, 32.1, 29.8, 29.7, 29.5, 29.3, 26.2, 22.9, 14.3 ($CH_3$).

3,5-bis(hexadecyloxy)benzoic acid (4e)

White solid (1.43 g, 97%). $^1$H-NMR (300 MHz, $CDCl_3$) δ 7.22 (s, 2H, $H_{arom}$), 6.68 (s, 1H, $H_{arom}$), 3.98 (t, J=6 Hz, 4H, $CH_2$), 1.78 (m, 4H, $CH_2$), 1.45-1.26 (m, 52H, $CH_2$), 0.88 (t, J=6 Hz, 6H, 2×$CH_3$). $^{13}$C-NMR (75 MHz, $CDCl_3$) δ 172.4 (CO), 160.4 ($C_{arom}$), 131.1 ($C_{arom}$), 108.3 ($CH_{arom}$), 107.6 ($CH_{arom}$), 68.5, 32.1, 29.9, 29.8, 29.5, 29.3, 26.2, 22.9, 14.3 ($CH_3$).

3,5-bis(octadecyloxy)benzoic acid (4f)

White solid (1.69 g, 86%). $^1$H-NMR (300 MHz, $CDCl_3$) δ 7.22 (s, 2H, $H_{arom}$), 6.68 (s, 1H, $H_{arom}$), 3.98 (t, J=6 Hz, 4H, $CH_2$), 1.78 (m, 4H, $CH_2$), 1.45-1.26 (m, 60H, $CH_2$), 0.88 (t, J=6 Hz, 6H, 2×$CH_2$). $^{13}$C-NMR (75 MHz, $CDCl_3$) δ 172.3 (C), 160.4 ($C_{arom}$), 131.1 ($C_{arom}$), 108.3 ($CH_{arom}$), 107.6 ($CH_{arom}$), 68.5, 32.1, 29.9, 29.8, 29.5, 29.3, 26.2, 22.9, 14.3 ($CH_3$).

General Procedure to Synthesis of Penta-O-Acetyl-Hexapyranoses (5a, 5b)

FIG. 5: To a solution of D-mannose or D-glucose (5.00 g, 27.8 mmol, 1.0 equiv.) in acetic anhydride (53.0 mL, 561 mmol, 20.2 eq.) cooled down with an iced-water bath was slowly added pyridine (67.0 mL, 831 mmol, 29.9 eq.). The mixture was then stirred at room temperature for 22 h. The mixture was diluted in cold water and extracted with DCM. To the organic phase was washed with 1N HCl solution severe times and, then washed with a saturated $NaHCO_3$ solution. The combinate organic layer was then washed with water, brine, dried over $NaSO_4$. The solvent was removed under reduced pressure to afford:

Penta-O-acetyl D-mannopyranose (5a)

White solid (7.60 g, 70%). $^1$H NMR (300 MHz, $CDCl_3$): δ=6.07 (d, 1H, $^3J_{1,2}$=1.9 Hz, H-1α), 5.33 (m, 2H, H-3, H-4), 5.24 (dd, 1H, $^3J_{2,3}$=2.2 Hz, H-2), 4.27 (dd, 1H, $^3J_{6a,6b}$=4.8 Hz, $^3J_{5,6}$=12.4 Hz, H-6a), 4.80 (m, 2H, H-6b, H-5), 2.16, 2.153, 2.08, 2.04, 1.99 ppm (5×s, 15H, $COCH_3$); $^{13}$C NMR (75 MHz, $CDCl_3$): δ=170.6, 169.9, 169.7, 169.5, 168.0 ($COCH_3$), 90.5 (C-1), 70.5 (C-5), 68.7 (C-3), 68.3 (C-2), 65.4 (C-4), 62.0 (C-6), 20.8, 20.7, 20.6, 20.6 ppm ($COCH_3$).

Penta-O-acetyl β-D-glucopyranosyl (5b)

(3.746 g, 9.6 mmol, 87%). $^1$H-NMR (300 MHz, CDCl3): δ=5.68 (d, J=8.3 Hz, 1H), 5.40 (dd, J=3.4, 0.9 Hz, 1H), 5.03-5.25 (m, 2H), 4.1 (dd, J=12.52, 4.49 Hz, 2H), 3.75-3.81 (m, 1H), 2.14-1.07 (4s, 12H, OAc). $^{13}$C NMR (75 MHz, CDCl3): δ=170.4-169.0 (4×CO), 92.2 (C-1), 71.8, 70.9, 67.0, 66.9, 61.1, 20.9-20.6 (4×$CH_3$).

2-Bromoethyl tetra-O-acetyl-α-D-mannopyranoside (8a) (Grabosch et al., 2010)

Penta-O-acetyl mannopyranose 2 (3 g, 7.7 mmol, 1 eq.) and 2-bromoethanol (1.6 mL, 23.1 mmol, 3 eq.) was dissolved in 15 mL of DCM. At 0° C., $BF_3Et_2O$ (5 mL, 40.5 mmol, 5.2 eq.) was added dropwise over 30 minutes. The mixture was then stirred for 1 hour at 0° C. and then kept at room temperature overnight. The mixture is then neutralized with 100 ml of a saturated aqueous $NaHCO_3$ solution. The organic phase was washed with water and then dried with anhydrous sodium sulfate. The solvent was evaporated under reduced pressure. The product was purified by a chromatographic column on silica gel with a gradient of Hexane/EtOAc as eluent. The desire product was obtained as white solid. Part was crystallized in DCM/Hexane mixture, thus giving colorless crystals. (2.158 g, 0.61%). Rf=0.40 (Toluene/EtOAc, 7:3): $^1$H-NMR (300 MHz, $CDCl_3$): 5.39-5.26 (m, 3H, $H_2$, and 4), 4.88 (d, 1H, J=3 Hz, H1), 4.28 (dd, 1H, J=12 Hz, J=6 Hz, H6a), 4.16-4.13 (m, 2H, H6b and H5), 3.94 (m, 2H, OCH2), 3.53 (t, 2H, J=6 Hz, CH2Br), 2.17-2.01 (4s, 12H, 4×$CH_3$).

2-Bromoethyl tetra-O-acetyl-β-D-glucopyranoside (8b) (Grabosch et al., 2010)

A mixture of β-D-glucose pentaacetate (6.2 g, 15.9 mmol), 2-bromoethanol (1.4 mL) and powdered molecular sieves (1.5 g) in DCM (50 mL) was stirred at room temperature for 30 minutes. The solution was cooled down to 0° C. and $BF_3.Et_2O$ (6 mL) was added dropwise. The mixture was stirred at room temperature for 5 hr. The mixture was quenched with saturated $NaHCO_3$. The mixture was diluted with DCM. DCM layer was separated and washed with $NaHCO_3$ solution until neutral and finally with saturated NaCl solution. The organic phase was dried over $Na_2SO_4$, and the solvent was evaporated, and the crude material was purified by column chromatography over silica gel (Hexane-EtOAc: 0-30% followed by Hexane-EtOAc-DCM: 7:3:2 and 5:4:2) and, then 3.4 g of product which was further purified by crystallization from EtOAc and hexanes (2.54 g, 35%).

6-Chlorohexyl tetra-O-acetyl-α-D-mannopyranoside (6a) (Tosin et al., 2002; Dhaware et al., 2013)

Penta-O-acetyl-D-mannopyranose (507 mg, 1.30 mmol, 1.0 eq.) and 6-chlorohexanol (340 μL, 2.56 mmol, 2.0 eq.) were dissolved in dry DCM (10 mL) at 0° C. $Et_2O·BF_3$ (480 μL, 3.90 mmol, 3.0 eq.) was added dropwise. The mixture is stirred at 0° C. for one hour and then at 40° C. for 17 h. The solution was neutralized by adding $NaHCO_3$ saturated solution (10 mL). The organic phase was extracted, washed with water, and dried. The DCM was removed, and the raw product was dried under vacuum (769 mg). The product was purified by column chromatography on silica gel (Gradient Hexane/EtOAc, 100:0 to 90:30) to afford the desired chlorohexyl-tetra-O-acetyl-α-D-mannopyranose 6a as a colorless oil (404 mg, 66%). $^1$H-NMR (300 MHz, $CDCl_3$) δ 5.34 (dd, J=9 Hz, J=3 Hz, 1H), 5.30-5.21 (m, 2H), 4.80 (d, J=3 Hz, 1H), 4.28 (dd, J=12 Hz, J=3 Hz, 2H), 4.12-4.08 (m, 1H), 4.00-3.94 (m, 1H), 2.15 (s, 3H, $CH_3$), 2.10 (s, 3H, $CH_3$), 2.04 (s, 3H, $CH_3$), 1.99 (s, 3H, $CH_3$), 1.81-1.74 (m, 2H), 1.62-1.48 (m, 2H), 1.50-1.37 (m, 4H). $^{13}$C-NMR (75 MHz, $CDCl_3$) δ 170.7-169.8 (4×CO), 97.6, 69.7, 69.2, 68.5 ($CH_2O$), 68.3, 66.3, 62.6; 45.0, 32.5 ($CH_2$), 29.2 ($CH_2$), 26.6 ($CH_2$), 25.5 ($CH_2$), 21.0-20.7 (4×$CH_3$).

6-Bromohexyl tetra-O-acetyl-α-D-mannopyranoside (6b) (Grabosch et al., 2010)

Penta-O-acetyl-D-mannopyranose (2 g, 5.12 mmol, 1 eq.) and 6-bromohexanol (1.6 mL, 12.2 mmol, 2.4 eq.) was dissolved in 10 mL of DCM. At 0° C., $BF_3·ET_2O$ (4 mL, 32.4 mmol, 6.3 eq.) was added dropwise over 30 minutes. The mixture is then stirred for one hour at 0° C. and then overnight at room temperature. The mixture was then neutralized with 50 mL of a saturated aqueous $NaHCO_3$ solution. The organic phase was washed with water and then dried with anhydrous sodium sulfate. The solvent was evaporated. The product was purified by a chromatographic column on silica gel with a gradient of Hexane/EtOAc as eluent. The pure product was obtained in the form of colorless oil (602 mg, 1.18 mmol, 23%). (eluent: hexane/EtOAc, 6:4): Rf=0.51; $^1$H-NMR (300 MHz, $CDCl_3$): δ=5.12-5.00 (m, 3H, H2,3 and 4), 4.60 (d, 1H, J=3 Hz, H1), 4.05 (dd, 1H, J=12 Hz and J=3 Hz, H6a), 3.88 (dd, 1H, J=12 Hz and J=3 Hz, H6b), 3.76 (m, 1H, H5), 3.50 (m, 1H, $OCH_2$), 3.23 (m, 4H, $OCH_2$, $CH_2Br$), 1.93-1.77 (s, 12H, 4×$CH_3$), 1.67 (m, 2H, $CH_2$), 1.43 (m, 2H, $CH_2$), 1.23 (m, 5H, $CH_2$). $^{13}$C-NMR (75 MHz, $CDCl_3$): δ=170.6-169.8 (CO), 97.6 (C1), 69.7 (C4), 69.2 (C3), 69.0 (C5), 68.7 ($OCH_2$), 66.3 (C2), 62.5 (C6), 34.0 ($CH_2Br$), 32.8 ($CH_2$), 29.6 ($CH_2$), 28.4 ($CH_2$), 25.8 ($CH_2$), 20.9-20.7 (4×$CH_3$).

2-Azidoethyl tetra-O-acetyl-α-D-mannopyranoside (9a) (Lindhorst et al., 2001)

2-Bromoethyl tetra-O-acetyl-mannopyranoside (1.656 g, 3.64 mmol, 1 eq.), sodium azide (1.183 g, 8.05 mmol, 5 eq.) and tetrabutylammonium bromide (235 g, 0.73 mmol) was dissolved in 5 mL of anhydrous DMF. The mixture was stirred for 20 h at 80° C. The solution was diluted with cold water. The aqueous phase is extracted 3 times with EtOAc. The organic phase was washed with water severe times and then dried over anhydrous sodium sulfate and the solvent was evaporated to afford the desire compound without any purification as colorless oil (1.399 g, 3.35 mmol, 92%). $^1$H-NMR (300 MHz, $CDCl_3$): δ=5.34-5.26 (m, 1H, H2, 3 and 4), 4.86 (d, 1H, J=3 Hz, H1), 4.28 (dd, 1H, J=12 Hz and J=6 Hz, H6a), 4.07 (dd, 1H, J=12 Hz and J=3 Hz, H6b), 4.03 (m, 1H, H5), 3.86 (m, 1H, $OCH_2$), 3.67 (m, 1H, $OCH_2$), 3.46 (m, 2H, $CH_2N3$), 2.15-1.99 (s, 12H, 4×$CH_3$). $^{13}$C-NMR (75 MHz, $CDCl_3$): δ=170.6-169.75 (4×CO), 97.8 (C1), 69.4 (C5), 68.9 (C3), 67.0 ($OCH_2$), 66.0 (C2), 62.5 (C6), 50.4 (C—$N_3$), 20.8-20.6 (4×$CH_3$). IR: 2937.67 (νC—H), 2104.90 (azide).

2-Azidoethyl tetra-O-acetyl-β-D-glucopyranoside (9b) (Grabosch et al., 2010)

According to the same synthesis procedure of 9a, The compound 9b was isolated as white solid (3.13 g, 7 mmol, 95%)$^1$H-NMR (300 MHz, $CDCl_3$) δ 5.22 (t, J=9.4 Hz, 1H), 5.17-4.96 (m, 2H), 4.60 (d, J=7.9 Hz, 1H), 4.26 (dd, J=12.3, 4.6 Hz, 1H), 4.16 (dd, J=12.3, 2.4 Hz, 1H), 4.04 (ddd, J=10.6, 4.7, 3.5 Hz, 1H), 3.78-3.65 (m, 2H), 3.58-3.42 (m, 1H), 3.29 (ddd, J=13.4, 4.6, 3.4 Hz, 1H), 2.05 (4s, 12H). IR: ν $N_3$: 2104.90.

6-Azidohexyl 2,3,4,6-tetra-O-acetylα-D-mannopyranoside (7a) (Tosin et al., 2002; Dhaware et al., 2013)

The above 6-chlorohexyl derivative (551 mg, 1.18 mmol, 1.0 eq.) was dissolved in dry DMF (5 mL). Sodium azide (385 mg, 5.92 mmol, 5.0 eq.) and sodium iodide (40 mg, 0.22 eq.) were added into the solution. The solution was stirred at 80° C. for 24 h. After cooled down to room temperature, the mixture was diluted with water and the aqueous phase was extracted 3 times with EtOAc. The organic phase was washed with water severe times, dried and concentrated under reduced pressure. The product was purified by silica gel column chromatography (Toluene/EtOAc, 3:2) to afford compound as a colorless oil (521 mg, 1.10 mmol, 93%); $R_f$=0.67 (Toluene/EtOAc, 3:2). $^1$H-NMR (300 MHz, $CDCl_3$): δ 5.36 (dd, 1H, $J_{2,3}$=3.3 Hz, $J_{3,4}$=10 Hz, H-3), 5.32-5.22 (m, 2H, H-4, H-2), 4.81 (d, 1H, $J_{1,2}$=1.6 Hz, H-1), 4.29 (dd, 1H, $J_{6a,6b}$=12.2 Hz $J_{5,6a}$=5.3 Hz, H-6a), 4.09 (dd, 1H, $J_{6a,6b}$=12.2 Hz, $J_{5,6b}$=2.4 Hz, H-6b), 3.98 (ddd, 1H, $J_{4,5}$=9.4 Hz, $J_{5,6a}$=5.3 Hz, $J_{5,6b}$=2.4 Hz, H-5), 3.76-3.66 (m, 1H. OCHH), 3.49-3.42 (m, 1H, OCHH), 3.29 (t, 1H, $J_{H—H}$=6.8 Hz, $CH_2$—$N_3$), 2.15-1.99 (s, 12H, $CH_3$), 1.73-1.50 (m, 4H), 1.50-1.29 (m, 4H). $^{13}$C-NMR (75 MHz, $CDCl_3$): 170.6-169.7 (4×CO), 97.6 ($C_1$), 69.7, 69.1, 68.4, 68.3, 66.3, 62.5, 51.3 ($CH_2N_3$), 29.1 ($CH_2$), 28.7 ($CH_2$), 26.5 ($CH_2$), 25.7 ($CH_2$), 20.9-20.7 (4×$CH_3$); IR: (2104 $cm^{-1}$ for $N_3$).

General Procedure to Synthesis Compounds (D) (10a-l, 10a'-l', 11a-l, 1a'-l')

To a solution of azidoalkyl 2,3,4,6-tetra-O-acteylα-D-mannopyranosides (7a-7b, 9a-9b) (1.0 equiv.) and bis (alkyloxy) benzoic acid (1.0 equiv.) in DCM (8.0 mL) was added Tributylphopshine (1.5 equiv.) at 0° C. and the mixture was stirred at 0° C. for 2 h and then at the room temperature for 24 h. The presence of amine was confirmed by TLC. To the reaction mixture, hydroxybenzotriazole (HOBT) (1.6 equiv.) and N,N'-diisopropylcarbodiimide (DIC) (2.1 equiv.) were added, and was stirred at room temperature for 96 h. The reaction was then diluted in ethyl acetate and the organic phase was washed with saturated $NaHCO_3$ solution and brine, dried and concentrated. The crude product was purified by column chromatography on silica gel (Hexane/AcOEt 1:0 to 7:3) to obtain compounds (10a-l, 10a'-l', 11a-l, 11a'-l')

C8 Tetraacetylated Mannosyl Monomer (10a)

C8 tetraacetylated mannosyl monomer (10a) was prepared according to general procedure D as a colorless oil compound (127 mg, 0,157 mmol, 74%). $^1$H-NMR (300 MHz, $CDCl_3$) δ 6.87 (d, 2H, $^4J_{Hortho-Hpara}$=2.2 Hz, H-ortho), 6.55 (t, 1H, $^4J_{Hpara-Hortho}$=2.2 Hz, H-para), 6.22 (t, 1H, $J_{Hamide-Hf}$=5.6 Hz, H-amide), 5.35 (dd, 1H, $J_{H3-H4}$=10 Hz, $J_{H3-H2}$=3.3 Hz, H3), 5.29 (d, 1H, $J_{H4-H3}$=9.6 Hz, H4), 5.23 (dd, 1H, $J_{H2-H3}$=3.2 Hz, $J_{H2-H1}$=1.7 Hz, H2), 4.81 (d, 1H, $J_{H1-H2}$=1.3 Hz, H1), 4.29 (dd, 2H, $^2J_{H6b-H6a}$=12.2 Hz, $J'_{H6a-H5}$=5.3 Hz, H6a), 4.11 (dd, 1H, $^2J_{H6b-H6a}$=12.2 Hz, $J'_{H6b-H5}$=2.3 Hz, H6b), 4.01-4.00 (m, 1H, H5), 3.96 (t, 4H, $J_{Hg-Hh}$=6.5 Hz, Hg), 3.73-3.66 (m, 1H, Ha), 3.49-3.40 (m, 3H, Ha', Hf), 2.16-2.00 (4s, 12H, $CH_3$), 1.81-1.72 (m, 4H, Hh), 1.68-1.61 (m, 4H, Hb, He), 1.44-1.42 (m, 8H, He, Hd, Hi), 1.31-1.28 (m, 16H, Hj, Hm), 0.89 (t, 6H, $J_{Hn-Hm}$=6.7 Hz, Hn).

C12 Tetraacetylated Mannosyl Monomer (10c)

C12 tetraacetylated mannosyl monomer (10c) was prepared according to general procedure D, the compound 10c was isolated as a colorless oil (155 mg, 0,168 mmol, 78%). $^1$H-NMR (300 MHz, $CDCl_3$) δ 6.86 (d, 2H, $^4J_{Hortho-Hpara}$=2.1 Hz, H-ortho), 6.52 (t, 1H, $^4J_{Hpara-Hortho}$=2.1 Hz, H-para), 6.34 (t, 1H, $J_{Hamide-Hf}$=5.7 Hz, H-amide), 5.33 (dd, 1H, $J_{H3-H4}$=10 Hz, $J_{H3-H2}$=3.3 Hz, H3), 5.27 (d, 1H, $J_{H4-H3}$=9.6 Hz, H4), 5.21 (dd, 1H, $J_{H2-H3}$=3.2 Hz, $J_{H2-H1}$=1.7 Hz, H2), 4.78 (d, 1H, $J_{H1-H2}$=1.3 Hz, H1), 4.27 (dd, 2H, $^2J_{H6b-H6a}$=12.2 Hz, $J'_{H6a-H5}$=5.3 Hz, H6a), 4.08 (dd, 1H, $^2J_{H6b-H6a}$=12.2 Hz, $J'_{H6b-H5}$=2.3 Hz, H6b), 3.99-3.97 (m, 1H, H5), 3.93 (t, 4H, $J_{Hg-Hh}$=6.5 Hz, Hg), 3.71-3.63 (m, 1H, Ha), 3.47-3.37 (m, 3H, Ha', Hf), 2.13-1.97 (4s, 12H, $CH_3$), 1.76-1.69 (m, 4H, Hh), 1.60-1.58 (m, 4H, Hb, He), 1.41-1.39 (m, 8H, He, Hd, Hi), 1.27-1.24 (m, 32H, Hj, Hq), 0.86 (t, 6H, $J_{Hr-Hq}$=6.6 Hz, Hr).

C14 Tetraacetylated Mannosyl Monomer (10d)

6-Azidohexyl tetra-O-acetyl-α-D-mannopyranoside (7a) (107 mg, 226 nmol, 1.0 eq.) and 3,5-bis(tetradecyloxy)

benzoic acid (4d) (121 mg, 221 nmol, 1.0 eq.) were dissolved in DCM at 0° C. $Bu_3P$ (55 μL, 223 nmol, 1.0 eq.) was added and the mixture was stirred at 0° C. for 2 h and then at room temperature for 25 h. The presence of amine was confirmed by TLC then HOBT (46 mg) and DIC (80 μL) were added, and the mixture was stirred at room temperature for 22 h. The reaction was not complete, HOBT (20 mg) and DIC (40 μL) were added, and the mixture was stirred at room temperature for 20 h. The mixture was diluted in EtOAc and washed with $NaHCO_3$ saturated solution and brine. The organic phase was dried with $Na_2SO_4$ and concentrated under reduced pressure. The crude product (304 mg) was purified by column chromatography on silica gel (Hexane/EtOAc 100:0 to 70:30) to yield 6-bis(tetradecyloxy)benzamido-N-hexyl tetra-O-acetyl-α-D-mannopyranoside (10d) as a white solid (132 mg, 61%). $^1$H NMR (300 MHz, $CDCl_3$) δ 6.86 (s, 2H, $CH_{ar}$), 6.54 (s, 1H, $CH_{ar}$), 6.19 (t, J=5.7 Hz, 1H, NH), 5.35 (dd, J=10.0 Hz, J=3.3 Hz, 1H), 5.30-5.27 (m, 1H, H), 5.23-5.22 (m, 1H, H), 4.80 (d, J=1.5 Hz, 1H), 4.28 (dd, J=12.2 Hz, J=5.3 Hz, 1H), 4.10 (dd, J=12.2 Hz, J=2.4 Hz, 1H), 4.00-3.93 (m, 4H, H), 3.69 (dt, J=9.6 Hz, J=6.4 Hz, 1H), 3.49-3.39 (m, 3H), 2.15-1.99 (4×s, 12H, 4×$CH_3$), 1.81-1.71 (m, 4H), 1.62 (t, J=6 Hz, 5H), 1.43-1.41 (m, 8H), 1.28 (d, J=9 Hz, 37H), 0.87 (t, J=6 Hz, 6H). $^{13}$C NMR (75 MHz, $CDCl_3$) δ 170.6, 170.1, 170.0, 169.7, 167.4, 160.3, 136.8, 105.3, 104.2, 97.5, 69.7, 69.2, 69.1, 68.4, 68.2, 66.3, 62.5, 40.0, 31.9, 29.7, 29.6, 29.4, 22.7, 11.1.

C14 Tetraacetylatedglucose Ethylene Monomer (11d')

Prepared according to general procedure D. As colorless oil (30 mg, 0.033 mmol, 72%). $^1$H-NMR (300 MHz, $CDCl_3$) δ 6.87 (d, J=2.2 Hz, 2H), 6.53 (m, 2H), 5.21 (t, J=9.5 Hz, 1H), 5.14-4.95 (m, 2H), 4.53 (d, J=7.9 Hz, 1H), 4.24 (dd, J=12.4, 4.9 Hz, 1H), 4.17-4.02 (m, 1H), 3.96 (t, J=6.5 Hz, 5H), 3.89-3.63 (m, 3H), 3.65-3.49 (m, 1H), 2.11-1.97 (3s, 9H), 1.94 (s, 3H), 1.85-1.69 (m, 4H), 1.53-1.18 (m, 42H), 0.97-0.79 (m, 6H). $^{13}$C-NMR (75 MHz, $CDCl_3$) δ 170.6, 170.1, 169.5, 169.4, 167.3, 160.4, 136.2, 105.3, 104.3, 101.0, 72.6, 72.0, 71.2, 69.0, 68.3, 61.7, 39.6, 31.9, 29.6, 29.6, 29.6, 29.6, 29.4, 29.3, 29.2, 26.0, 22.7, 20.6, 20.6, 20.5, 14.1. ESI+-HRMS: $[M+H]^+$ calculated for $C_{51}H_{85}NO_{13}$: 919.6021. Found: 920.6098.

General Procedure to Synthesis Compounds (E) (14-17a)

Figure 6:
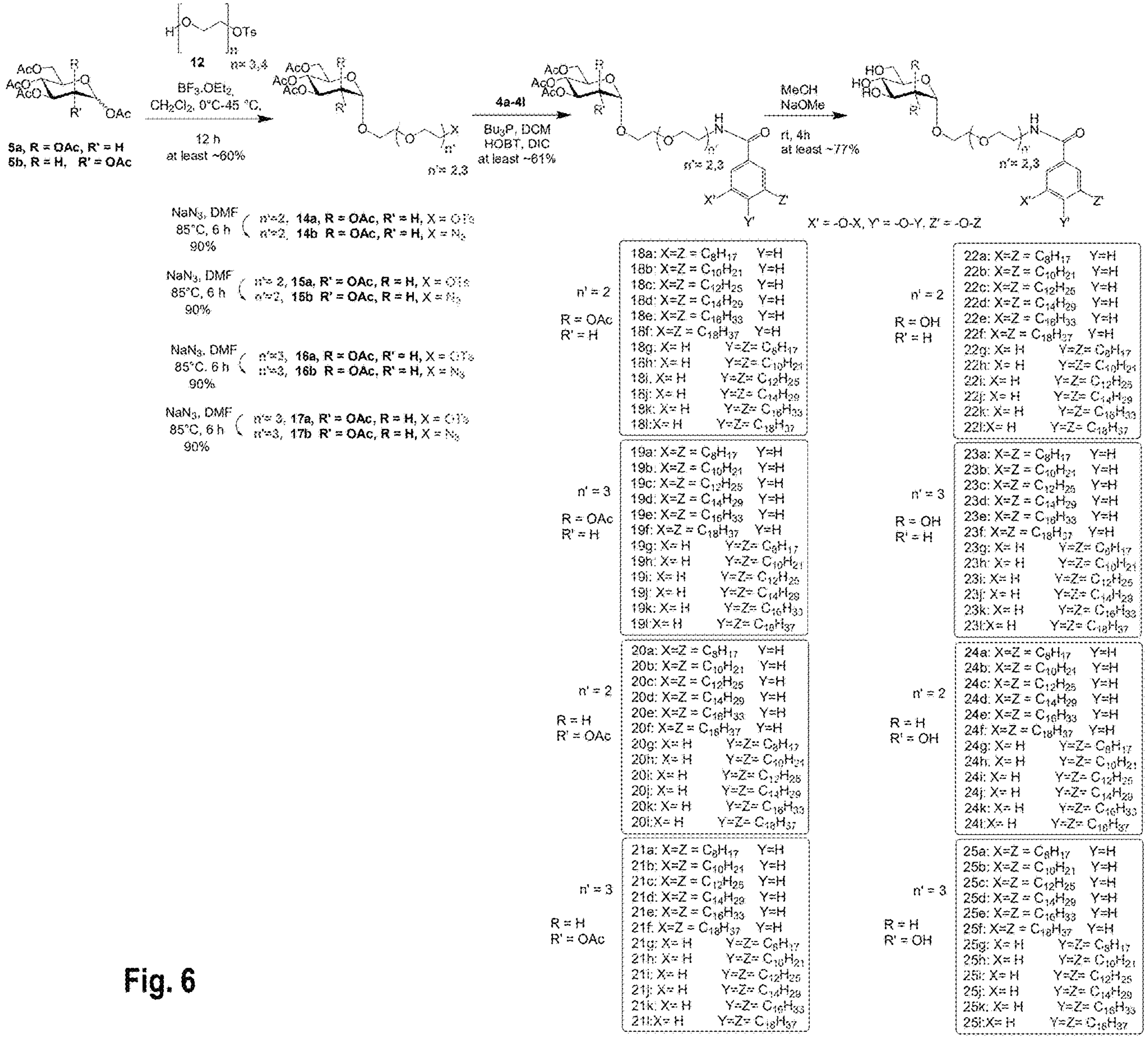
FIG. 6 shows the synthesis scheme of synthetic glycolipids 22a-25l.
Figure 7:
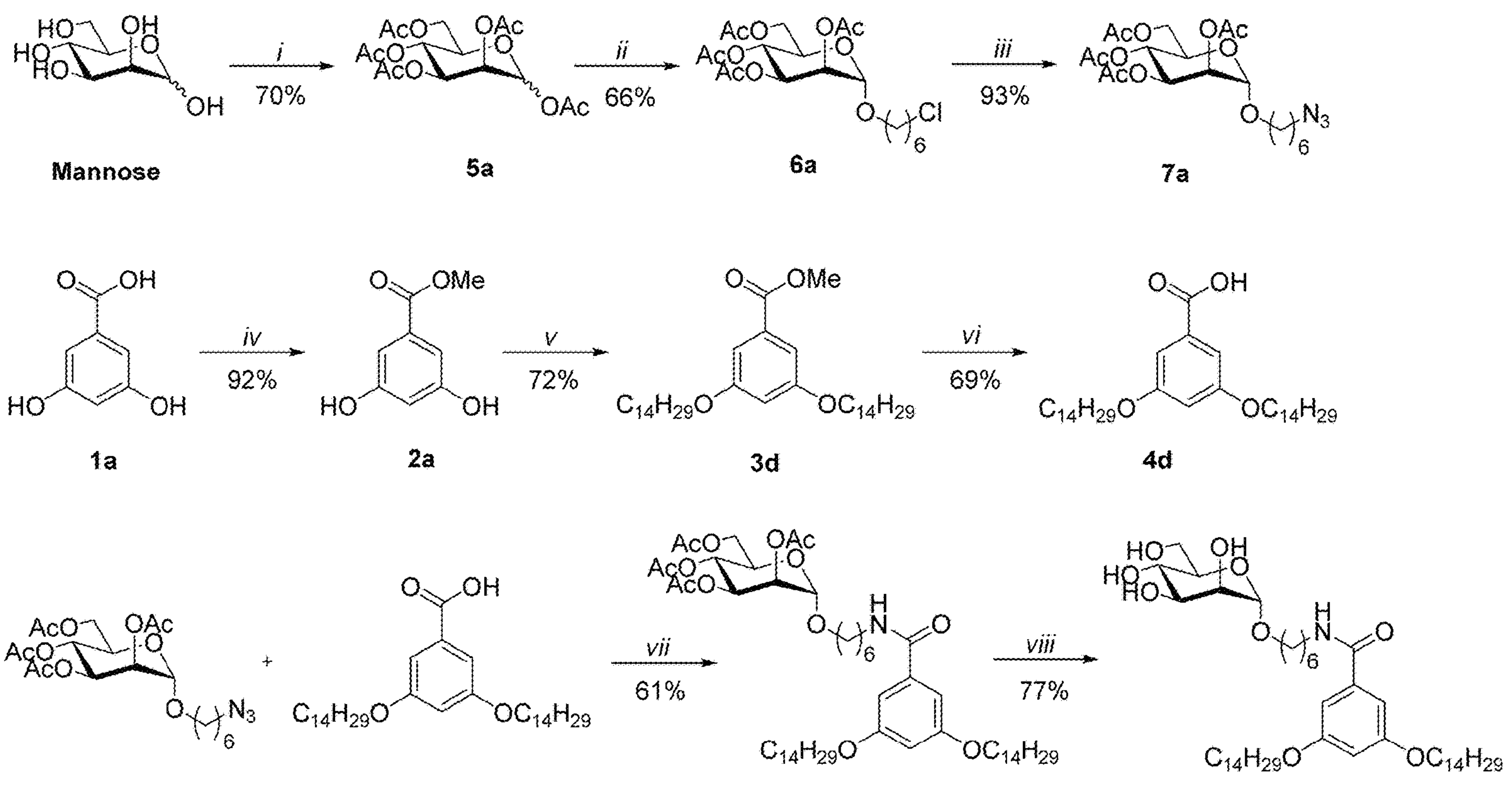
FIG. 7 shows the synthesis scheme of compound 12d also referred to as "$MG_{12d}$".

FIG. 6: To a solution of Penta-O-acetyl D-mannopyranose or β-D-glucose pentaacetate (1 eq.) was added triethylene or tetra ethylene glycol monotosylate (2.3 eq.) in dry DCM. Boron trifluoride diethyl etherate (2.3 eq.) was added dropwise at 0° C. under argon atmosphere and was stirred at this temperature for 40 min. Temperature was increased up to 40° C. and the reaction mixture was stirred for 17 h. Ice was added in the reaction mixture and stirred for additional 30 min. Extraction was performed with DCM. Organic layer was washed with saturated $NaHCO_3$ and dried over $Na_2SO_4$. After purification on column chromatography on silica gel (hexane/ethyl acetate 6:4) afford the desired products as colorless oil.

2-[2-(2-toluene-4-sulfonyloxy)ethoxy]ethoxyl (2,3,4,6-tetra-O-acetyl-α-D-Mannopyranosides (14a) (Grabosch et al., 2010)

This compound was obtained as a colorless oil (2.357 g, 3.71 mmol, 61%). $R_f$=0.32 (hexane/ethyl acetate 6:4). $^1$H-NMR (300 MHz, $CDCl_3$) δ 7.80 (d, J=8.3 Hz, 2H, $H_{arom}$), 7.34 (d, J=8.0 Hz, 2H, $H_{arom}$), 5.38-5.25 (m, 3H, H-2, 3 and 4), 4.87 (d, J=1.6 Hz, 1H, H-1), 4.28 (dd, 1H, J=5.0 and 12.3 Hz, H-6a), 4.09 (dd, 1H, J=2.5 and 12.3 Hz, H-6b), 4.18-4.01 (m, 3H, $OCH_2$ and H-5), 3.85-3.75 (m, 1H), 3.73-3.56 (m, 9H, OCH2), 2.45 (s, 3H, $CH_3$·Ph), 2.16-2.09 (s, 12H, 4×$CH_3$). $^{13}$C-NMR (75 MHz, $CDCl_3$): δ 170.8, 170.2, 170.1, 169.9, 144.5, 133.0, 129.6, 127.9, 97.9, 71.0, 70.9, 70.3, 70.2, 69.7, 69.2, 68.6, 67.6, 66.3, 62.6, 50.8, 21.6, 21.0, 20.9, 20.8, 20.7.

2-[2-(2-toluene-4-sulfonyloxy)ethoxy]ethoxyl (2,3,4,6-tetra-O-acetyl-/3-D-glucopyranoside (15a) (Lindhorst et al., 2001)

Physical data matched those published using a related procedure and the compound was obtained as a colorless oil (394 mg, 0.83 mmol, 52%). $R_f$=0.20 (hexane/ethyl acetate: 1:1), $^1$H-NMR (300 MHz, $CDCl_3$): δ=7.79 (d, 2H, $^3$J=8.29 Hz, H-arom), 7.34 (d, $^3$J=8.29 Hz, 2H, H-arom), 5.20 (dd, $^3J_{2,3}$=9.6 Hz, 1H, H-3), 5.08 (ddt, $^3J_{3,4}$=9.7 Hz, 1H, H-4), 4.98 (dd, $^3J_{1,2}$=8.0 Hz, $^3J_{2,3}$=9.6 Hz, 1H, H-2), 4.6 (d, $^3J_{1,2}$=8.0 Hz, 1H, H-1), 4.25 (dd, $^3J_{5,6}$=4.7 Hz, $^2J_{6,6'}$=12.3 Hz, 1H, H-6a), 4.16-4.12 (m, 3H, $OCH_2$ and H-6b), 3.94-3.91 (m, 1H, $CH_2$), 3.74-3.67 (m, 4H, $CH_2$, H-5), 3.64-3.55 (m, 6H, $CH_2$), 2.44 (s, 3H, $CH_3$), 2.07, 2.02, 2.01, 2.00 (s, 12H, 4×$CH_3$); $^{13}$C-NMR (75 MHz, $CDCl_3$): δ=170.7, 170.3, 169.4, 169.4 (4×CO), 144.8, 133.0, 129.8, 128.0, 100.9, 72.8, 71.8, 71.3, 70.8, 70.7, 70.3, 69.2, 69.1, 68.7 ($CH_2$), 68.4 (C-4), 62.0 (C-6), 21.6 ($CH_3$), 20.7, 20.7, 20.6, 20. (4×$CH_3$).

General Procedure to Synthesis Compounds (14-17b) (F)

The compounds 14a, 15a, 16a and 17a was dissolved in 4 ml dry DMF. $NaN_3$ (8.00 equiv.) and NaI (0.50 equiv.) were added into the solution and stirred under $N_2$ overnight. The mixture of reaction was diluted in water and extracted with ethyl acetate and washed with water severe times. The organic layer was dried over $Na_2SO_4$ and concentrated under reduced pressure to afford desired compound without purification.

2-(2-(2-Azidoethoxy)ethoxy)ethyoxyl (2,3,4,6-tetra-O-acetyl-α-D-Mannopyranosides (14b)

According to the procedure F, the compound 14b was isolated as colorless oil (75 mg, 0.148 mmol, 94%). $^1$H-NMR (300 MHz, $CDCl_3$): δ 5.39 (dd, 1H, $^3J_{2,3}$=3.3 Hz, $^3J_{3,4}$=10 Hz, H-3), 5.30 (dd, 1H, $^3J_{3,4}$=$^3J_{4,5}$ 10 Hz, H-4), 5.26 (dd, 1H, $^3J_{1,2}$=2 Hz, $^3J_{2,3}$=3.7 Hz, H-2), 4.89 (d, 1H, $^3J_{1,2}$=1.6 Hz, H-1), 4.28 (dd, 1H, $^3J_{5,6a}$=5.0 Hz, $J_{6a,6b}$=12.3 Hz, H-6a), 4.09 (dd, 1H, $^3J_{5,6a}$=2.5 Hz, $J_{6a,6b}$=12.3 Hz, H-6b), 4.05 (m, 1H, H-5), 3.81 (m, 1H, $OCH_2$), 3.71-3.64 (m, 9H, $OCH_2$), 3.42 (t, 2H, J=4.8 Hz, $CH_2N_3$), 2.18-2.03 (s, 12H, 4×$CH_3$), $^{13}$C-NMR (75 MHz, $CDCl_3$): δ 170.9, 170.6, 170.0, 169.9, 169.7, 97.9, 71.0, 70.9, 70.3, 70.2, 69.7, 69.2, 68.6, 67.6, 66.2, 62.6, 50.6, 21.1, 20.9, 20.7, 20.7.

2-(2-(2-Azidoethoxy)ethoxy)ethyoxyl (2,3,4,6-tetra-O-acetyl-β-D-glucopyranoside (15b)

According to the procedure F, the compound 14b was isolated as colorless oil (70 mg, 0.138 mmol, 88%), $^1$H-NMR (300 MHz, $CDCl_3$): δ=5.22 (dd, $^3J_{2,3}$=9.5 Hz, 1H, H-3), 5.09 (dd, $^3J_{3,4}$=9.6 Hz, 1H, H-4), 5.00 (dd, $^3J_{1,2}$=8.0

Hz, $^3J_{2,3}$=9.5 Hz, 1H, H-2), 4.66 (d, $^3J_{1,2}$=8.0 Hz, 1H, H-1), 4.27 (dd, $^3J_{5,6}$=4.7 Hz, $^3J_{6,6}$=12.3 Hz, 1H, H-6), 4.15 (dd, $^3J_{6,6}$=2.7 Hz, $^3J_{6,6}$=12.3 Hz, H-6'), 3.95-3.91 (m, 1H, $CH_2$), 3.74-3.67 (m, 3H, $CH_2$, H-5), 3.64-3.55 (m, 8H, $CH_2$), 3.41 (t, 2H, J=4.8 Hz, $CH_2N_3$), 2.09-2.03 (s, 12H, 4×$CH_3$); $^{13}$C-NMR (75 MHz, $CDCl_3$): δ=170.7, 170.3, 169.4, 169.4, 100.8, 72.8, 71.7, 71.7, 70.7, 70.7, 70.4, 70.0, 69.5, 69.0, 68.4, 61.9, 50.6, 20.7, 20.6, 20.6, 20.6.

General Procedure to Synthesis Compounds (18a-l, 19a-l, 20a-l, and 21a-l) (G)

To a solution of azido products (14b-17b) (1.0 equiv.) and bis (alkyloxy) benzoic acid (4a-l) (1.0 equiv.) in DCM (8.0 mL) was added tributylphopshine (1.5 equiv.) at 0° C., and the mixture was stirred at 0° C. for 2 h, and then at the room temperature for 24 h. The presence of amine was confirmed by TLC. To reaction mixture hydroxybenzotriazole (HOBT) (1.6 equiv.) and N, N'-diisopropylcarbodiimide (DIC) (2.1 equiv.) were added and was stirred at room temperature for 96 h. The reaction was then diluted in ethyl acetate and the organic phase was washed with saturated $NaHCO_3$ solution and brine, dried and concentrated. The crude product was purified by column chromatography on silica gel (Hexane/AcOEt 1:1) to obtain compounds (18a-l, 19a-l, 20a-l, and 21a-l).

C14 Monomer Man-Peg 3-Acid Lipid (18d)

According to the procedure G, the compound 18d was isolated as colorless oil (60 mg, 0.06 mmol, 35%). $R_f$=0.30 (hexane/ethyl acetate 1:1), $^1$H-NMR (300 MHz, $CDCl_3$) δ 6.90 (d, 2H, $^4J_{Hortho-Hpara}$=2.2 Hz, $H_{Ortho}$), 6.71 (s, 1H, NH), 6.50 (s, 1H, $H_{Para}$), 5.36 (dd, 1H, $J_{H2-H3}$=3.3 Hz, $J_{H3,H4}$=10 Hz, H3), 5.30 (dd, 1H, $J_{H3-H4}$=9.7 Hz, $J_{H4-H5}$=1.2 Hz, H4), 5.26 (dd, 1H, $J_{H2-H1}$=1.7 Hz, $J_{H2-H3}$=3.1 Hz, H2), 4.87 (d, 1H, $J_{H1-H2}$=1.4 Hz, H1), 4.28 (dd, 2H, $^3J_{H6a-H5}$=5.2 Hz, $^2J_{H6b-H6a}$=12.3 Hz, H6a), 4.09 (dd, 1H, $^3J_{H6b-5}$=2.2 Hz, $2J_{H6b-H6a}$=12.3 Hz, H6b), 4.06-4.02 (m, 1H, H5), 3.96 (t, 4H, J=6.6 Hz, $OCH_2$), 3.85-3.76 (m, 1H, $OCH_2$), 3.72-3.60 (m, 11H, $OCH_2$), 2.18-1.76 (S, 12H, 3×$CH_3$), 1.90-1.57 (m, 6H, $CH_2$), 1.50-1.39 (m, 5H, $CH_2$), 1.38-1.19 (m, 42H, $CH_2$), 0.98-0.81 (m, 7H, $CH_2$). $^{13}$C-NMR (75 MHz, $CDCl_3$) δ 169.6, 169.0, 168.9, 168.7 (4×CO), 166.4 (CO), 159.3 ($C_{arom}$), 135.6 ($C_{arom}$), 104.4 ($CH_{arom}$), 103.1 ($CH_{arom}$), 96.7 (C-1), 69.6, 69.3, 69.0, 68.5, 68.0, 67.4, 61.4, 38.8, 30.9, 28.6, 28.6, 28.6, 28.6, 28.5, 28.5, 28.3, 28.3, 24.9, 21.3, 19.7, 19.6, 13.0, 12.9, 12.5. ESI$^+$-HRMS: $[M+H]^+$ calculated for $C_{55}H_{94}NO_{15}$: 1008.6622. Found 1008.6618.

C16 Monomer Man-Peg 3-Acid Lipid (18e)

According to the procedure F, the compound 18e was isolated as colorless oil (52 mg, 0.047 mmol, 32%). $R_f$=0.20 (hexane/ethyl acetate 1:1), $^1$H-NMR (300 MHz, $CDCl_3$) δ 6.91 (d, 2H, $^4J_{Hortho-Hpara}$=2.2 Hz, $H_{Ortho}$), 6.75 (s, 1H, NH), 6.57 (s, 1H, $H_{para}$), 5.38 (dd, 1H, $J_{H2,H3}$=3.3 Hz, $J_{H3,H4}$=10.5 Hz, H3), 5.32 (dd, 1H, $J_{H3-H4}$=9.6 Hz, $J_{H4,H5}$=1.2 Hz, H4), 5.28 (dd, 1H, $J_{H2,H1}$=1.7 Hz, $J_{H2-H3}$=4.3 Hz, H2), 4.88 (d, 1H, $J_{H1-H2}$=1.4 Hz, H1), 4.3 (dd, 2H, $^3J_{H6a-H5}$=5.2 Hz, $^2J_{H6b-H6a}$=12.4 Hz, H6a), 4.16-4.02 (m, 1H, H6b, H5), 3.97 (t, 4H, J=6.5 Hz, $OCH_2$), 3.89-3.77 (m, 2H, $OCH_2$), 3.74-3.61 (m, 11H, $OCH_2$), 2.18-1.76 (S, 12H, 4×$CH_3$), 1.90-1.57 (m, 5H, $CH_2$), 1.52-1.10 (m, 50H, $CH_2$), 0.98-0.81 (m, 7H, $CH_2$). $^{13}$C-NMR (75 MHz, $CDCl_3$) δ 170.7, 170.0, 169.9, 167.7 (4×CO), 167.5 (CO), 160.3 ($C_{arom}$), 136.5 ($C_{arom}$), 105.4 ($CH_{arom}$), 104.2 ($CH_{arom}$), 97.7 (C-1), 70.6, 69.5, 69.1, 68.4, 68.3, 66.1, 62.5, 42.3, 39.6, 31.9, 29.7, 29.6, 29.6, 29.4, 29.4, 29.3, 29.2, 28.3, 26.0, 23.3, 22.7, 20.8, 20.7, 20.7, 20.6, 14.12, 13.5. ESI$^+$-HRMS: $[M+]^+$ calculated for $C_{59}H_{102}NO_{15}$: 1064.7244. Found 1064.7210.

General Procedure for De-O-Acetylation (H) (12a-12l, 12'a-l, 13a-l and 13'a-l; 22a-l, 23a-l, 24a-l, and 25a-l)

The acetylated compounds (10a-10l, 10'a-l, 11a-l and 11'a-l; 18a-l, 19a-l, 20a-l and 21a-l) was dissolved in dry MeOH (3 mL), a solution of sodium methoxide (1 M in MeOH, 0.5 eq.) was added until pH 8 to 9 in the solution, and the reaction mixture was stirred at room temperature until disappearance of the starting material and only one spot on TLC. The solution was then, neutralized by addition of ion-exchange resin $H^+$ (Amberlite™ IR 120), filtered, washed with MeOH and then the solvent was removed in vacuo. The residue was then lyophilized to yield the fully deprotected final products without any purification.

6-Bis(octacyloxy)benzamido-N-hexyl α-D-mannopyranoside (12a)

(92 mg, 0.144 mmol, 92%)$^1$H-NMR (300 MHz, $CDCl_3$) δ 6.88 (d, 2H, $^4J_{Hortho-Hpara}$=2.0 Hz, H-ortho), 6.85 (1H, H-para), 6.51 (1H, H-amide), 4.79 (s, 1H, H1), 3.90-3.35 (14H, H3, H4, H2, H6a, H6b, H5, Hg, Ha, Ha', Hf), 1.73-1.66 (m, 4H, Hh), 1.54 (4H, Hb, He), 1.38-1.25 (24H, He, Hd, Hi-Hm), 0.87 (t, 6H, $J_{Hn-Hm}$=6.6 Hz, Hn). $^{13}$C-NMR (75 MHz, $CDCl_3$) δ 167.7 (CO), 160.3 ($C_{arom}$), 136.6 ($C_{arom}$), 105.4 ($CH_{arom}$), 104.4 ($CH_{arom}$), 97.6, 68.3, 31.9, 29.7, 29.6, 29.4, 29.3, 29.2, 26.1, 22.7, 14.1. ESI$^+$-HRMS: $[M+H]^+$, calculated for $C_{35}H_{61}NO_9$: 640.4380 found 640.4423.

6-Bis(dodecyloxy)benzamido-N-hexyl α-D-mannopyranoside (12c)

(89 mg, 0.118 mmol, 70%). $^1$H-NMR (300 MHz, $CDCl_3$) δ 6.88 (2H, H-ortho), 6.77 (1H, H-para), 6.51 (1H, H-amide), 4.80 (s, 1H, H1), 3.90-3.36 (14H, H3, H4, H2, H6a, H6b, H5, Hg, Ha, Ha', Hf), 1.74-1.69 (m, 4H, Hh), 1.55 (4H, Hb, He), 1.32-1.26 (40H, He, Hd, Hi-Hq), 0.88 (t, 6H, $J_{Hr-Hq}$=6.4 Hz, Hr). $^{13}$C-NMR (75 MHz, $CDCl_3$) δ 167.7 (CO), 160.4 ($C_{arom}$), 136.6 ($C_{arom}$), 105.4 ($CH_{arom}$), 104.4 ($CH_{arom}$), 97.6, 68.3, 32.0, 29.79, 29.75, 29.71, 29.5, 29.4, 29.3, 26.1, 22.7, 14.2 ($CH_3$). ESI$^+$-HRMS: $[M+H]^+$, calculated for $C_{43}H_{77}NO_9$: 752.5632, found 752.5661.

6-bis(tetradecyloxy)benzamido-N-hexyl α-D-mannopyranoside (12d)

6-bis(tetradecyloxy)benzamido-N-hexyl tetra-O-acetyl-α-D-mannopyranoside (10d) (132 mg, 135 nmol, 1.0 eq.) was dissolved in dry MeOH (13 mL) and 0.5 M NaOMe solution was added to the mixture until pH=8 to 9. The mixture was then stirred at room temperature for 4 h. After total consumption of starting material showed by TLC, IR-120 $H^+$ resin was added, and the mixture was stirred for 20 minutes until pH 7. The mixture was filtrated, washed with MeOH and DCM and concentrated under reduce pressure. The product was purified on column chromatography on silica gel (by gradient: 2, 4, 6 and 8% of MeOH in DCM) to yield 6-bis(tetradecyloxy)benzamido-N-hexyl α-D-mannopyranoside (12d) as a white solid (84 mg, 77%). $^1$H NMR (300 MHz, $CDCl_3$) δ 6.86 (s, 2H, $CH_{ar}$), 6.54 (s, 1H, $CH_{ar}$), 6.46 (t, J=5.7 Hz, 1H, NH), 4.88 (s, 1H), 4.80 (s, 1H), 4.72 (s, 1H), 4.28 (s, 1H), 3.93-3.74 (m, 9H), 3.6 (dd, J=30 Hz, J=9 Hz, 2H), 3.38 (d, J=6 Hz, 3H), 2.10 (s, 1H), 1.76-1.71 (m, 4H), 1.55-1.25 (m, 52H), 0.87 (t, J=6 Hz, 6H).

C14 Monomer Glucose Ethyl Benzoic Acid (13d')

Prepared according to general procedure H and isolated as white solid. $^1$H-NMR (300 MHz, $CDCl_3$) δ 7.52 (s, 1H), 6.91 (s, 2H, J=1.6 Hz, $H_{Ortho}$), 6.48 (s, 1H), 4.38 (m, 5H), 3.76 (m, 8H), 3.66-3.10 (m, 6H), 1.67 (d, J=6.5 Hz, 4H), 1.29 (d, J=21.8 Hz, 44H), 0.88 (t, J=6.6 Hz, 6H). $^{13}$C-NMR (75 MHz, $CDCl_3$) δ 168.2, 160.2, 136.0, 105.7, 68.3, 31.9, 29.7, 29.7, 29.5, 29.4, 29.2, 26.0, 22.7, 14.1. ESI$^+$-HRMS: $[M+H]^+$ calculated for $C_{43}H_{77}NO_9$: 751.5598. Found: 752.5677.

C14 Monomer Mannose Triethylene Glycole (23d)

Prepared according to general procedure H and isolated as white solid (32 mg, 0.038 mmol, 63%). $^1$H-NMR (300 MHz, $CDCl_3$) δ 6.98 (s, 1H, NH), 6.90 (d, 2H, J=1.6 Hz, $H_{Ortho}$), 6.53 (1H, $H_{para}$), 4.83 (s, 1H, H1), 3.98-3.8 (m, 8H), 3.79-3.48 (m, 15H) 1.82-1.69 (m, 4H), 1.51-1.15 (m, 46H), 1.39-1.25 (48H, He, Hd, Hi and Hs), 0.9-0.78 (m, 7H). $^{13}$C-NMR (75 MHz, $CDCl_3$) δ 160.3 (CO), 136.8 ($C_{arom}$), 105.2 ($CH_{arom}$), 104.0 ($CH_{arom}$), 100.1 (C-1), 69.7, 69.1, 68.4, 68.2, 66.2, 62.5, 31.9, 29.6, 29.7, 29.6, 29.5, 29.4, 29.4, 29.2, 26.0, 22.6, 14.1 ($CH_3$). ESI$^+$-HRMS: $[M+H]^+$, calculated for $C_{47}H_{85}NO_{11}$: 839.6123. found 840.6160.

D-Mannopyranose Pentaacetate (5a) (Tosin et al., 2002)

To a solution of D-mannose (5.00 g, 27.8 mmol, 1.0 eq.) in acetic anhydride (53.0 mL, 561.0 mmol, 20.2 eq.) cooled down with an iced-water bath was slowly added pyridine (67.0 mL; 831.0 mmol, 29.9 eq.). The mixture was then stirred at room temperature for 22 h. A TLC analysis confirmed that the starting material has completely reacted. The mixture was diluted in cold water and extracted with DCM. To the organic phase was washed with 1N HCl solution severe times and, then washed with a saturated $NaHCO_3$ solution. The combinate organic layer was then washed with water, brine, dried over $NaSO_4$. The solvent was removed under reduced, and the product was dried under vacuum to afford D-mannopyranose pentaacetate (5a) as a white solid (7.60 g, 70%). $^1$H NMR (300 MHz, $CDCl_3$): δ=6.07 (d, 1H, $^3J_{1,2}$=1.9 Hz, H-1α), 5.33 (m, 2H, H-3, H-4), 5.24 (dd, 1H, $^3J_{2,3}$=2.2 Hz, H-2), 4.27 (dd, 1H, $^3J_{6a,6b}$=4.8 Hz, $^3J_{5,6}$=12.4 Hz, H-6a), 4.80 (m, 2H, H-6b, H-5), 2.16, 2.153, 2.08, 2.04, 1.99 ppm (5×s, 15H, $COCH_3$); $^{13}$C NMR (75 MHz, $CDCl_3$): δ=170.6, 169.9, 169.7, 169.5, 168.0 ($COCH_3$), 90.5 (C-1), 70.5 (C-5), 68.7 (C-3), 68.3 (C-2), 65.4 (C-4), 62.0 (C-6), 20.8, 20.7, 20.6, 20.6 ppm ($COCH_3$).

6-Chlorohexyl tetra-O-acetyl-α-D-mannopyranoside (6a) (Dhaware et al., 2013)

D-mannopyranose pentaacetate (5a) (507 mg, 1.30 mmol, 1.0 eq.) and 6-chlorohexanol (340 μL, 2.56 mmol, 2.0 eq.) were dissolved in dry DCM (10 mL) at 0° C. $Et_2O{\cdot}BF_3$ (480 μL, 3.90 mmol, 3.0 eq.) was added dropwise. The mixture is stirred at 0° C. for 1 h and then at 40° C. for 17 h. The solution was neutralized by adding $NaHCO_3$ saturated solution (10 mL). The organic phase was extracted, washed with water, and dried. The DCM was removed under reduced pressure and then, was purified by column chromatography on silica gel (Gradient Hexane/EtOAc, 100:0 to 90:30) to afford 6-Chlorohexyl tetra-O-acetyl-α-D-mannopyranoside (6a) as a colorless oil (404 mg, 66%). $^1$H NMR (300 MHz, $CDCl_3$) δ 5.34 (dd, J=9 Hz, J=3 Hz, 1H), 5.30-5.21 (m, 2H), 4.80 (d, J=3 Hz, 1H), 4.28 (dd, J=12 Hz, J'=3 Hz, 2H), 4.12-4.08 (m, 1H), 4.00-3.94 (m, 1H), 2.15 (s, 3H, $CH_3$), 2.10 (s, 3H, $CH_3$), 2.04 (s, 3H, $CH_3$), 1.99 (s, 3H, $CH_3$), 1.81-1.74 (m, 2H), 1.62-1.48 (m, 2H), 1.50-1.37 (m, 4H). $^{13}$C NMR (75 MHz, $CDCl_3$) δ 170.67-169.79 (4×CO), 97.62, 69.74, 69.17, 68.48 ($CH_2O$), 68.31, 66.31, 62.59, 45.01, 32.48 ($CH_2$), 29.15 ($CH_2$), 26.62 ($CH_2$), 25.47 ($CH_2$), 20.95-20.74 (4×$CH_3$).

6-Azidohexyl tetra-O-acetyl-α-D-mannopyranoside (7a) (Dhaware et al., 2013)

6-Chlorohexyl tetra-O-acetyl-α-D-mannopyranoside (6a) (551 mg, 1.18 mmol, 1.0 eq.) was dissolved in dry DMF (5 mL). Sodium azide (385 mg, 5.92 mmol, 5.0 eq.) and sodium iodide (40 mg, 0.2 mmol, 0.2 eq.) were added into the solution. The mixture was stirred at 80° C. for 24 h and then at room temperature for 16 h. The mixture was diluted in water and the aqueous phase was extracted 3 times with EtOAc. Organic phase was washed with water, dried, and concentrated under reduced pressure. The product was purified by column chromatography on silica gel (Hex/EtOAc 100:0 to 70:30) to afford the desire compound 6-azidohexyl tetra-O-acetyl-α-D-mannopyranoside (7a) as colorless oil (521 mg, 93%). $^1$H NMR (300 MHz, $CDCl_3$) δ 5.34 (dd, 1H, J=12 Hz et J'=3 Hz, H3), 5.28 (d, 1H, J=9 Hz, H4), 5.22 (m, 1H, H2), 4.80 (d, 1H, J=3 Hz, H1), 4.28 (dd, 1H, J=12 Hz et J'=6 Hz, H6a), 4.10 (dd, 1H, J=12 Hz et J'=3 Hz, H6b), 3.98 (m, 1H, H5), 3.68 (m, 1H, $OCH_{2a}$), 3.45 (m, 1H, $OCH_{2b}$), 3.28 (t, 2H, J=6 Hz, $CH_2N_3$), 2.15-1.99 (4×s, 12H, 4×$CH_3$), 1.63 (t, 4H, 2×$CH_2$), 1.41 (t, 4H, 2×$CH_2$). $^{13}$C NMR (75 MHz, $CDCl_3$) δ 170.7-169.8 (4×CO), 97.6 ($C_1$), 69.7, 69.2, 68.5, 68.3, 66.3, 62.6, 51.4 ($CH_2N_3$), 29.2 ($CH_2$), 28.8 ($CH_2$), 26.5 ($CH_2$), 25.8 ($CH_2$), 21.0-20.8 (4×$CH_3$).

Methyl 3,5-dihydroxybenzoate (2a) (Percec et al., 2013)

3,5-dihydroxybenzoic acid (1a) (5.00 g, 32.4 mmol 1.0 eq.), methanol (40 mL, 988.0 mmol, 30.5 eq.) and sulfuric acid (0.25 mL, 4.80 mmol, 0.15 eq.) was heated at 70° C. for 7 h. The reaction was cooled to room temperature and the methanol was removed. The solid was treated carefully with a saturated aqueous $NaHCO_3$ solution, and the product was extracted with ethyl acetate. The organic phase was washed with water and brine and finally evaporated to give methyl 3,5-dihydroxybenzoate (Aa) as a white solid (5.00 g, 92%). The product was used for the next reaction without further purification. $^1$H NMR (300 MHz, DMSO-$d_6$) δ 9.66 (s, 2H, OH), 6.85 (d, J=3 Hz, 2H, H-arom), 6.48 (dd, J=3 Hz, 1H, H-arm), 3.83 (s, 3H, $OCH_3$). $^{13}$C NMR (75 MHz, DMSO-$d_6$) δ 166.4 (CO), 158.7 ($C_{arom}$), 131.5 ($C_{arom}$), 107.3 (2×$CH_{arom}$), 52.1 ($OCH_3$).

Methyl 3,5-bis(tetradecyloxy)benzoate (3d) (Diroll et al., 2016)

To a stirred solution of methyl 3,5-dihydroxybenzoate (2a) (1.00 g, 5.95 mmol, 1.0 eq.) and 1-bromotetradecane (3.96 g, 14.28 mmol, 2.4 eq.) in DMF (25 mL) were added $K_2CO_3$ (2.22 g, 16.1 mmol, 2.7 eq.) and KI (69 mg, 417 nmol, 0.07 eq.) and, then the resulting mixture was stirred at 90° C. for 12 h. The reaction mixture was cooled, and diluted with $CHCl_3$, washed with $H_2O$ (100 mL) and brine (100 mL), dried over anhydrous $Na_2SO_4$, filtered and the filtrate was concentrated under reduced pressure. To the residue was added MeOH to induce the precipitation. The precipitate was collected by filtration, washed with methanol, and dried to obtain methyl 3,5-bis(tetradecyloxy)benzoate (3d) as a white solid (2.44 g, 72%). $^1H$ NMR (300 MHz, $CDCl_3$) δ 7.16 (s, 2H, H-arom), 6.63 (s, 1H, H-arom), 3.96 (t, J=6 Hz, 4H, $CH_2$), 3.89 (s, 3H, $OCH_3$), 1.77 (m, 4H, $CH_2$), 1.44-1.26 (m, 44H, $CH_2$), 0.88 (m, 6H, 2×$CH_3$). $^{13}C$ NMR (75 MHz, $CDCl_3$) δ 167.1 (CO), 160.3 ($CH_{ar}$), 131.9 ($CH_{ar}$), 107.7 ($CH_{ar}$), 106.7 ($CH_{ar}$), 68.4, 52.3, 32.1, 29.8, 29.7, 29.5, 29.3, 26.2, 22.8, 14.3 ($CH_3$).

3,5-bis(tetradecyloxy)benzoic acid (4d)

Methyl 3,5-bis(tetradecyloxy)benzoate (3d) (1.50 g, 2.67 mmol, 1.0 eq.), KOH (599 mg, 10.68 mmol, 4.0 eq.) in water (9 mL) and ethanol (60 mL) were refluxed for 4 h. Then reaction mixture was cooled to room temperature and concentrated. 1N Hydrochloric acid solution was then added carefully until pH=1 followed by extraction with dichloromethane. The combined organic solvents were separated, dried over MgSO4 and evaporated to yield 3,5-bis(tetradecyloxy)benzoic acid (4d) as a white solid (1.03 g, 69%). $^1H$ NMR (300 MHz, $CDCl_3$) δ 7.22 (s, 2H, $H_{ar}$), 6.69 (s, 1H, $H_{ar}$), 3.98 (t, J=6 Hz, 4H, $CH_2$), 1.79 (m, 4H, $CH_2$), 1.46-1.26 (m, 44H, $CH_2$), 0.88 (m, 6H, 2×$CH_3$). $^{13}C$ NMR (75 MHz, $CDCl_3$) δ 172.4 (COOH), 160.4 ($CH_{ar}$), 131.1 ($CH_{ar}$), 108.3 ($CH_{ar}$), 107.6 ($CH_{ar}$), 68.5, 32.1, 29.8, 29.7, 29.5, 29.3, 26.2, 22.9, 14.3 ($CH_3$).

6-bis(tetradecyloxy)benzamido-N-hexyl α-D-mannopyranoside tetraacetate (10d)

6-Azidohexyl tetra-O-acetyl-α-D-mannopyranoside (7a) (107 mg, 226 nmol, 1.0 eq.) and 3,5-bis(tetradecyloxy) benzoic acid (4d) (121 mg, 221 nmol, 1.0 eq.) were dissolved in DCM at 0° C. $Bu_3P$ (55 μL, 223 nmol, 1.0 eq.) was added and the mixture was stirred at 0° C. for 2 h and then at room temperature for 25 h. The presence of amine was confirmed by TLC then HOBT (46 mg) and DIC (80 μL) were added, and the mixture was stirred at room temperature for 22 h. The reaction was not complete, HOBT (20 mg) and DIC (40 μL) were added, and the mixture was stirred at room temperature for 20 h. The mixture was diluted in EtOAc and washed with $NaHCO_3$ saturated solution and brine. The organic phase was dried with $Na_2SO_4$ and concentrated under reduced pressure. The crude product (304 mg) was purified by column chromatography on silica gel (Hexane/EtOAc 100:0 to 70:30) to yield 6-bis(tetradecyloxy)benzamido-N-hexyl tetra-O-acetyl-α-D-mannopyranoside (10d) as a white solid (132 mg, 61%). $^1H$ NMR (300 MHz, $CDCl_3$) δ 6.86 (s, 2H, $CH_{ar}$), 6.54 (s, 1H, $CH_{ar}$), 6.19 (t, J=5.7 Hz, 1H, NH), 5.35 (dd, J=10.0 Hz, J=3.3 Hz, 1H), 5.30-5.27 (m, 1H, H), 5.23-5.22 (m, 1H, H), 4.80 (d, J=1.5 Hz, 1H), 4.28 (dd, J=12.2 Hz, J=5.3 Hz, 1H), 4.10 (dd, J=12.2 Hz, J=2.4 Hz, 1H), 4.00-3.93 (m, 4H, H), 3.69 (dt, J=9.6 Hz, J=6.4 Hz, 1H), 3.49-3.39 (m, 3H), 2.15-1.99 (4×s, 12H, 4×$CH_3$), 1.81-1.71 (m, 4H), 1.62 (t, J=6 Hz, 5H), 1.43-1.41 (m, 8H), 1.28 (d, J=9 Hz, 37H), 0.87 (t, J=6 Hz, 6H). $^{13}C$ NMR (75 MHz, $CDCl_3$) δ 170.6, 170.1, 170.0, 169.7, 167.4, 160.3, 136.8, 105.3, 104.2, 97.5, 69.7, 69.2, 69.1, 68.4, 68.2, 66.3, 62.5, 40.0, 31.9, 29.7, 29.6, 29.4, 22.7, 11.1.

6-bis(tetradecyloxy)benzamido-N-hexyl α-D-mannopyranoside (12d)

6-bis(tetradecyloxy)benzamido-N-hexyl tetra-O-acetyl-α-D-mannopyranoside (10d) (132 mg, 135 nmol, 1.0 eq.) was dissolved in dry MeOH (13 mL) and 0.5 M NaOMe solution was added to the mixture until pH=8 to 9. The mixture was then stirred at room temperature for 4 h. After total consumption of starting material showed by TLC, IR-120 $H^+$ resin was added and the mixture was stirred for 20 minutes until pH 7. The mixture was filtrated, washed with MeOH and DCM and concentrated under reduce pressure. The product was purified on column chromatography on silica gel (by gradient: 2, 4, 6 and 8% of MeOH in DCM) to yield 6-bis(tetradecyloxy)benzamido-N-hexyl α-D-mannopyranoside (12d) as a white solid (84 mg, 77%). $^1H$ NMR (300 MHz, $CDCl_3$) δ 6.86 (s, 2H, $CH_{ar}$), 6.54 (s, 1H, $CH_{ar}$), 6.46 (t, J=5.7 Hz, 1H, NH), 4.88 (s, 1H), 4.80 (s, 1H), 4.72 (s, 1H), 4.28 (s, 1H), 3.93-3.74 (m, 9H), 3.6 (dd, J=30 Hz, J=9 Hz, 2H), 3.38 (d, J=6 Hz, 3H), 2.10 (s, 1H), 1.76-1.71 (m, 4H), 1.55-1.25 (m, 52H), 0.87 (t, J=6 Hz, 6H).

Example 4: Preparation of Mannosylated Glycoliposomes (MGs)

Liposomes were prepared by the injection method, as previously described in Goyard et al., 2016. Briefly, 100 μL of a solution of MG (e.g., 12d) in a water miscible solvent (typically tetrahydrofuran or EtOH) were injected via micropipet in 2 mL of nanopure water, followed by 5 seconds of vortexing. Giant vesicles were prepared by film hydration. Briefly, 25 μL of a 5 mg/mL solution of MG in $CHCl_3$ were uniformly deposited on a confocal microscopy slide and left to evaporate at room temperature for 16 hours. The slide was then immersed in nanopure water, heated at 60° C. and left to hydrate overnight. For confocal microscopy visualization, 5 μL of a 0.1 mg/mL solution of hydrophobic nile red were added to the MG solution prior to evaporation on the microscope slide.

Example 5: Characterization of Mannosylated Glycoliposomes (MGs)

Dynamic Light Scattering (DLS) Spectra of MG at Various Concentrations in THF and EtOH Different solutions of 12a (C8), 12c (C12), 12d (C14), 12e (C16), 22c (C12), 22d (C14), 22e (C16) in THF and EtOH were prepared from 0.5 mg/mL to 10 mg/mL. 100 μL of these preparations were injected in a constant 2 mL of nanopure water followed by 5 seconds of vortexing, and analyzed by DLS, to determine the diameter size of the MGs, as shown in Table 2.

TABLE 2

DLS Results of different MGs by carbon chain length of hydrophobic segment

| Mannosylated Glycopliposomes (compound No) | Carbon chain length of hydrophobic segment | Diameter (nm) | Polydispersity Index (PDI) |
|---|---|---|---|
| 12a | C8 | 300[a] | 0.178 |
| 12c | C12 | 267 [a] | 0.202 |
| 12d | C14 | 286 [a] | 0.040 |
| 12e | C16 | 766 nm (not soluble) | 0.908 |

TABLE 2-continued

| DLS Results of different MGs by carbon chain length of hydrophobic segment | | | |
|---|---|---|---|
| Mannosylated Glycopliposomes (compound No) | Carbon chain length of hydrophobic segment | Diameter (nm) | Polydispersity Index (PDI) |
| 22c | C12 | 386 [b] | 0.130 |
| 22d | C14 | 343 [c] | 0.240 |
| 22e | C16 | 136 | 0.190 |

[a] At 3.2 mg/mL THF
[b] At 2.5 mg/mL EtOH
[c] At 1 mg/mL EtOH

Binding and Agglutination Abilities of Mannoliposomes

Figure 8:
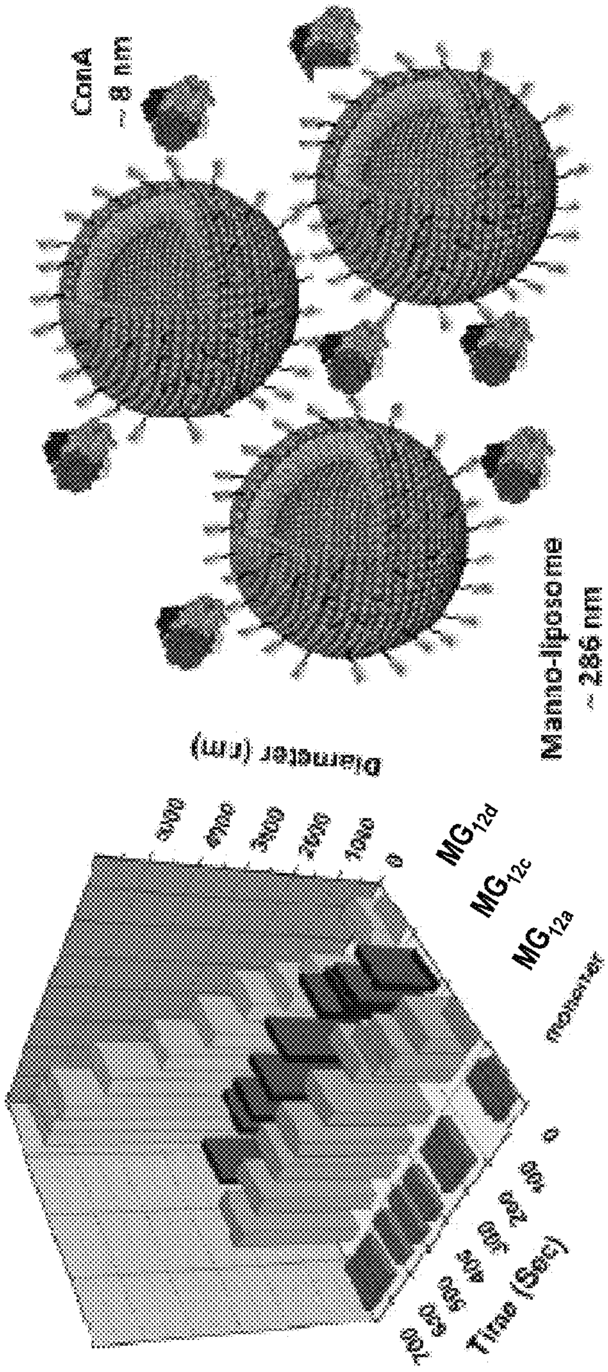
FIG. 8 shows the time scale agglutination of mannosylated glycoliposomes (MG) formed with 12a (C8), 12c (C12), and 12d (C14) in the presence of Con A (4 binding sites/mol) at 0.5 mg/mL (100 L) in PBS.

Next, the ability of MGs to bind and agglutinate with lectins was assessed via cross-linking with concanavalin A (ConA) from *Canavalia ensiformis* (Jack bean). Since lectins, such as ConA, bind various carbohydrate receptors that are widely expressed by different cells (e.g., immune cells such as Dendritic cells), MGs may be used to target specific cells. As shown in FIG. 8, $MG_{12a}$, $MG_{12c}$, and $MG_{12d}$ (in the absence of cholesterol) rapidly form larger aggregates in the presence of tetrameric lectin ConA. $MG_{12d}$ was shown to form the largest aggregates with ConA. In comparison to the data in Goyard et al. (2016), agglutination of ConA with $MG_{12d}$ occurs more rapidly than with $MG_{C12}$ Comparing the agglutination timesstudies with those previously performed with $MG_{C12}$, the agglutination of particles formed with 12d occurs much more rapidly and to a greater extent than those formed with $MG_{C12}$. This suggests that the mannose residue in 12d is more freely available for protein binding, confirming our hypothesis about an inadequate distance between the sugar head group and lipid tails outlined earlier. In fact, the enhanced agglutination of liposomes assembled from 12d occurred under a Con A concentration approximately 4× lower than that with $MG_{C12}$, further supporting that the additional alkyl linker between the mannose residue and the aromatic lipid architecture in 12d translates into glycoliposomes with a more freely available sugar group.

Cellular Uptake Ability of Mannoliposomes

Figure 9A:
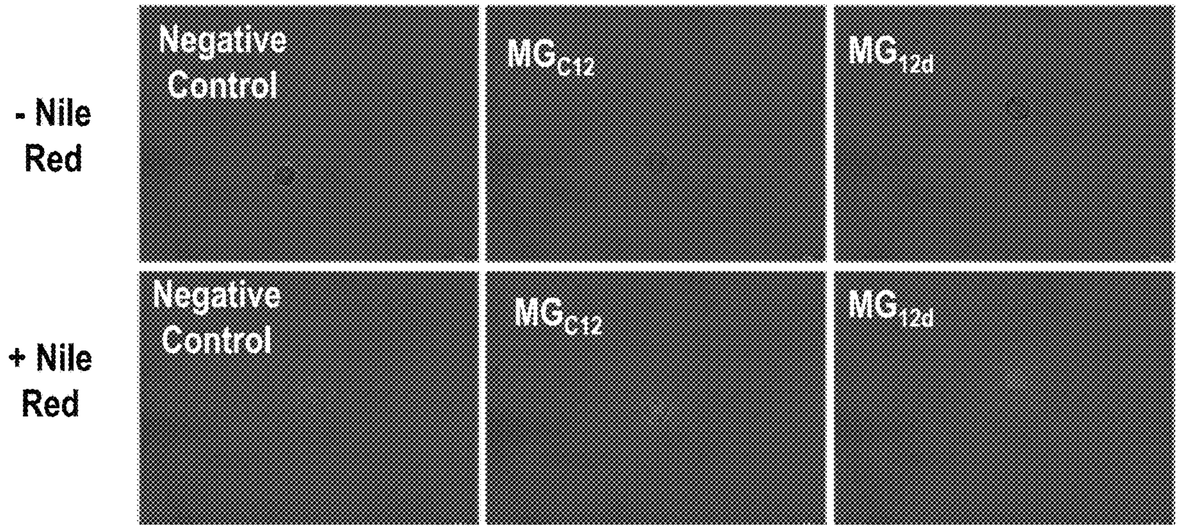
FIG. 9 shows the visualization of Nile Red with and without mannosylated glycoliposomes formed with 12d ($MG_{12d}$) or with $MG_{C12}$ in JAWSII (FIG. 9A) and J774A.1 (FIG. 9B). Cells were treated for 1 hour without (top panels)
Figure 9B:
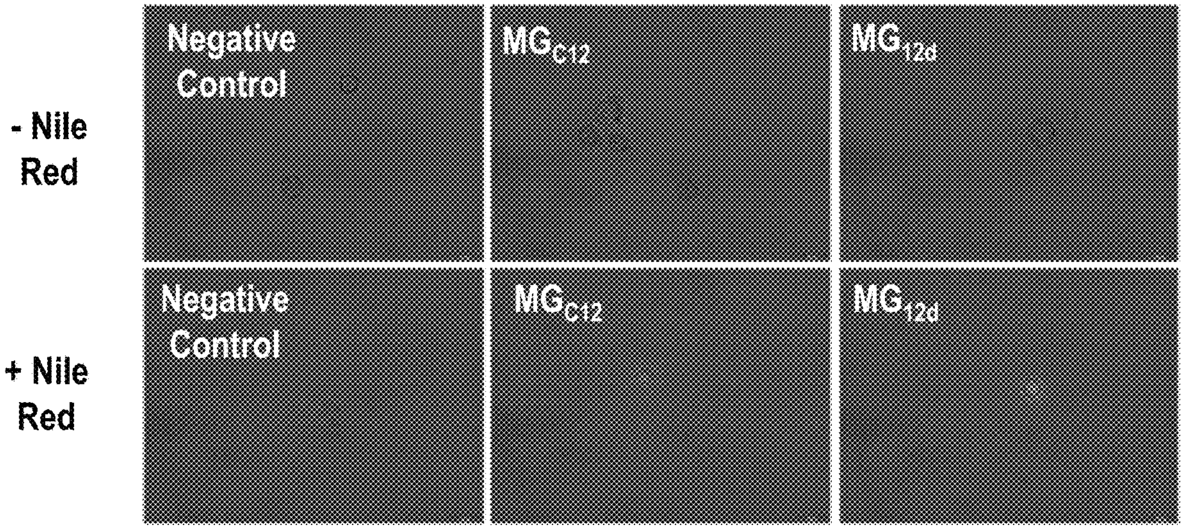

Next, to assess cellular uptake ability of MGs, different cell types were treated with MGs incubated with Nile Red. The murine JAWSII dendritic cell and J774A.1 macrophage cell lines were chosen to represent immunological cell targeting, and by extension, the macrophages and microglia of the blood-brain barrier (BBB), while the human HeLa cell line was chosen to represent targeting to cancerous cells. FIG. 9 shows the visualization of Nile Red by fluorescence microscopy with and without mannosylated glycoliposomes formed with 12d ($MG_{12d}$) or with $MG_{C12}$ (without cholesterol) in JAWSII (FIG. 9A) and J774A.1 (FIG. 9B). FIG. 10 shows the results of Nile Red uptake by Flow cytometry. Importantly, cellular uptake was greatly enhanced by either MGs. No statistical differences, however, were observed between either MG. This may be due to experimental conditions not being fully optimized or possible being optimized in the presence of cholesterol. Furthermore, Nile Red was also observed with an additional formulation, $MG_{22}$a (FIG. 11)

Immunogenicity Assessment of Mannoliposomes

Next, immunogenicity of MGs was assessed in order to determine their potential safety in vivo. Immune responses in PBMCs (isolated from 3 healthy volunteers) were measured in FIG. 12. PBMCs were seeded at $10^6$ cells/mL and left untreated or treated with glycoliposomes formed from $MG_{12d}$ (10 g/mL). Cells were incubated for 48 hours and supernatants were analysed for the production of cytokines by ELISA. As shown in FIG. 12, there were no statistical difference in cytokine production between untreated cells and cells treated with $MG_{12d}$ (no cholesterol). Furthermore, as shown in Table 3, $MG_{12d}$ did not induce any hemolysis at all concentrations tested. ACK lysis buffer was used as a positive control.

The data demonstrate the potential safety of MGs for use in vivo.

TABLE 3

| Hemolytic assay with $MG_{12d}$ | | |
|---|---|---|
| Compound | Concentration (μg/mL) | % Hemolysis (±SEM) |
| $MG_{12d}$ | 100 | 0 |
| | 50 | 0 |
| | 25 | 0 |
| | 12.5 | 0 |
| PBS | — | 0 |
| ACK Lysis Buffer | — | 100 ± 2 |

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

All publications and patent applications cited in this specification are herein incorporated by reference as if each individual publication or patent application were specifically and individually indicated to be incorporated by reference.

REFERENCES

Brujinzeel, A. W. (2009). Kappa-opioid receptor signalling and brain reward function. *Brain Res. Rev.* 62, 127-146.

Dhaware, V., A. Y, Shaikh., M, Kar., S, Hotha, S. S, Gupta. *Langmuir*. (2013), 29, 5659-5667

Diroll, B. T.; Jishkariani, D.; Cargnello, M.; Murray, C. B.; Donnio, B. *J. Am. Chem. Soc*. (2016), 138, 10508.

El-Faham et al., "Peptide Coupling Reagents, More than a Letter Soup", *Chem. Rev.* 2011, 111, 6557-6602.

Grabosch, C., et al., *Synthesis*. (2010) 0828-0836.

Goyard, D.; Shiao, T. C. et al., *J Mater. Chem. B*. (2016), 4, 4227.

D. Guggi, N. Langoth, M. H. Hoffer, M. Wirth, A. Bernkop-Schnmrch. Comparative evaluation of cytotoxicity of a glucosamine-TBA conjugate and a chitosan-TBA conjugate. *Int. J. Pharm.* 278 (2004) 353-360.

Lewicky et al., (2020). Mannosylated glycoliposomes for the delivery of a peptide kappa opioid receptor antagonist to the brain. *European Journal of Pharmaceutics and Biopharmaceutics,* 154; 290-296.

Lewicky et al., (2021). Improving the Utility of a Dynorphin Peptide Analogue Using Mannosylated Glycoliposomes. *Int. J. Mol. Sci.,* 22, 7996, 1-13.

Lindhorst, T. K.; Kotter, S.; Krallmann-Wenzel, U.; Ehlers, S, *J Chem. Soc*., (2001), 823-831.

Percec, V., Leowanawat, P., Sun, H-J., Kulikov, O., Nusbaum, C. D., Tran, T. M., Bertin, A., Wilson, D. A., Peterca, M., Zhang, S., Kamat, N. P., Vargo, K., Moock, D., Johnston, E. D., Hammer, D. A., Pochan, D. J., Chen, Y., Chabre, Y. M., Shiao, T. C., Bergeron-Brlek, M., Andre, S., Roy, R., Gabius, H-J., Heiney, P. A. *J. Am. Chem. Soc.*, (2013), 135, 9055-9077.

Tamiaki, H.; Azefu, Y.; Shibata, R.; Sato, R.; Toma, K. (2006). Oligomethylene spacer length dependent interaction of synthetic galactolipids incorporated in phospholipid layers with ricin. *Colloids Surf B Biointerfaces,* 53, 87-93.

Tosin, T. V, Murphy. *Org. Lett.*, (2002), 4, 3675-3678.

The invention claimed is:

1. A synthetic glycolipid having the formula (I)

(I)

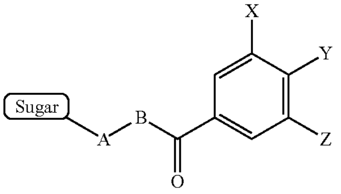

wherein

A represents $(CH_2)_n$ with n being an integer from 2 to 10 or $CH_2—CH_2—[O—CH_2—CH_2]_m$ with m being 2 or 3;

B represents $NR^3$, with $R^3$ representing H, Me, Et or n-Pr;

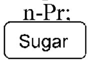 represents

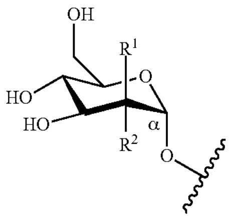

or

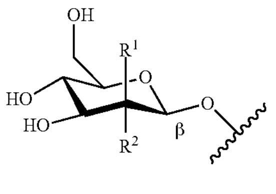

where $R^1$ represents OH and $R^2$ represents H, or where $R^1$ represents H and $R^2$ represents OH;

Y represents H when X and Z which are identical represent $O—(CH_2)_p—CH_3$, or X represents H when Y and Z which are identical represent $O—(CH_2)_p—CH_3$, with p being an integer from 5 to 18;

with the proviso that the synthetic glycolipid of formula (I) is different than the compound of formula (II) or (III)

(II)

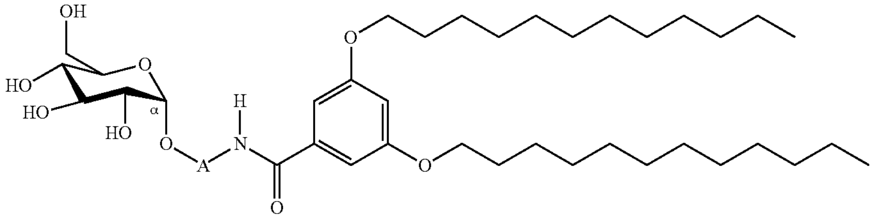

(III)

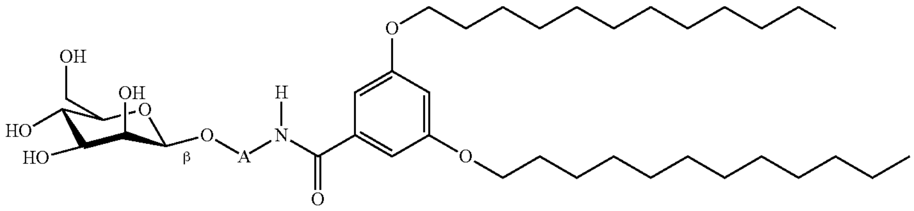

where $A=(CH_2)_{n'}$, with n'=2, 6, 10;

with the proviso that the synthetic glycolipid of formula (I) is different than the following compound

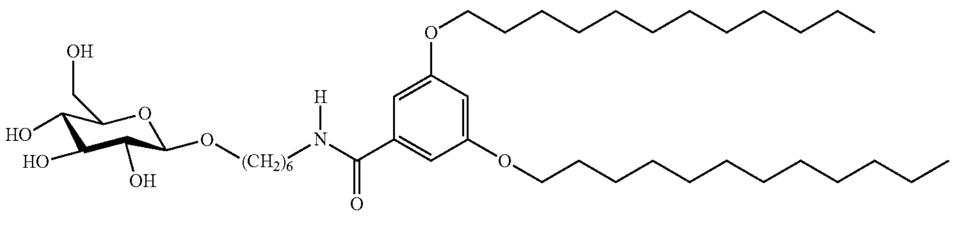

;

and with the proviso that the synthetic glycolipid of formula (I) is different than the compound of formula (IV)

(IV)

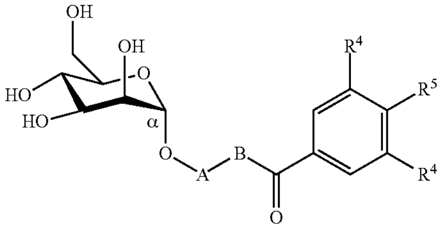

where A represents $CH_2$—$CH_2$;

and

B represents NH, $R^5$ is H and $R^4$ are identical $OC_xH_y$ groups with x is 12, 14, 16, or 18 and y is 2x+1; or B represents NMe, $R^4$ is $OC_{18}H_{37}$ and $R^5$ is H;

or where A represents —$(CH_2)_6$—, B represents NH, $R^5$ is H and $R^4$ are both $O(CH_2)_{12}H$.

2. The synthetic glycolipid of claim 1, wherein A represents ($CH_2$) n with n being an integer from 2 to 10.

3. The synthetic glycolipid of claim 1, wherein A represents ($CH_2$) n with n being 2 or 6.

4. The synthetic glycolipid of claim 1, wherein A represents $CH_2$—$CH_2$—[O—$CH_2$—$CH_2$]$_m$ with m being 2 or 3.

5. The synthetic glycolipid of claim 1, wherein B represents $NR^3$ where $R^3$ is H or Me.

6. The synthetic glycolipid of claim 1, wherein X represents H, and Y and Z represent a group O—$(CH_2)_p$—$CH_3$, with p being an integer from 5 to 18.

7. The synthetic glycolipid of claim 1, wherein Y represents H, and X and Z represent a group O—$(CH_2)_p$—$CH_3$, with p being an integer from 5 to 18.

8. The synthetic glycolipid of claim 1, wherein

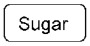 represents

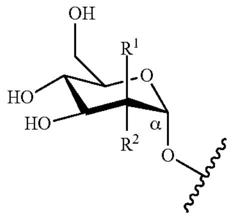

where $R^1$ represents OH and $R^2$ represents H, or where $R^1$ represents H and $R^2$ represents OH.

9. The synthetic glycolipid of claim 1, wherein

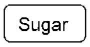 represents

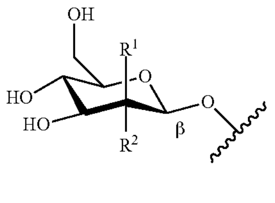

where $R^1$ represents OH and $R^2$ represents H, or where $R^1$ represents H and $R^2$ represents OH.

10. The synthetic glycolipid of claim 1, having the formula (Ia)

(Ia)

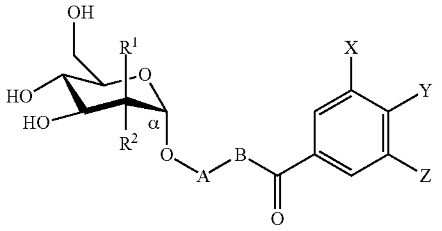

wherein

A represents $(CH_2)_n$ with n=6;

B represents NH;

$R^1$ represents OH and $R^2$ represents H;

Y represents H, and X and Z which are identical represent O—$(CH_2)_p$—$CH_3$, with p=13.

11. A method for delivering a therapeutic or diagnostic agent to the central nervous system of a patient in need of the therapeutic or diagnostic agent, the method comprising:

entrapping the therapeutic or diagnostic agent into a glycoliposome comprising a plurality of synthetic glycolipids; and administering the glycoliposome with the entrapped therapeutic or diagnostic agent to the patient;

wherein each synthetic glycolipid has the following formula (I)

(I)

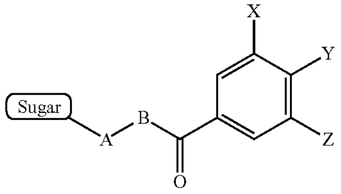

wherein

A represents ($CH_2$) n with n being an integer from 2 to 10 or $CH_2$—$CH_2$—[O—$CH_2$—$CH_2$]$_m$ with m being an integer from 1 to 5;

B represents $NR^3$, with $R^3$ representing H, Me, Et or n-Pr;

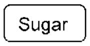 represents

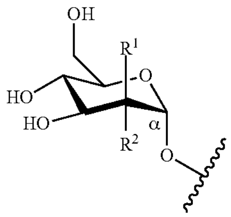

or

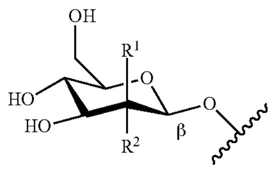

where $R^1$ represents OH and $R^2$ represents H, or where $R^1$ represents H and $R^2$ represents OH;

Y represents H when X and Z which are identical represent O—$(CH_2)_p$—$CH_3$, or X represents H when Y and Z which are identical represent O—$(CH_2)_p$—$CH_3$, with p being an integer from 5 to 18.

12. The method of claim 11, wherein each synthetic glycolipid has the formula (Ia)

(Ia)

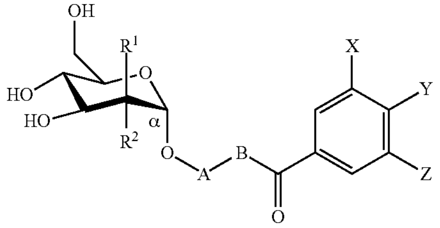

wherein

A represents $(CH_2)$ n with n=6;

B represents NH;

$R^1$ represents OH and $R^2$ represents H;

Y represents H, and X and Z which are identical represent O—$(CH_2)_p$—$CH_3$, with p=13.

13. The method of claim 11, wherein the therapeutic or diagnostic agent comprises:

(i) a peptide, peptide analog, peptidomimetic (peptide mimetic), or small molecule;

(ii) a neurotransmitter receptor ligand;

(iii) an opioid receptor ligand;

(iv) a k-opioid receptor antagonist; or (v) Dynantin, JVA-901, Arodyn, Cyclodyn, Zyklophin, [Pro3]- and [Pro3, Arg8]-Dyn A-(1-11)$NH_2$, Norbinaltorphimine (norBIN), 5'-Guanidinonaltrindole (GNTI), JDTic, ML140, ML140-11, Fedotozine, Asimadoline, ADL 10-1010, Salvinorin A, E-2078, SK-9709, JVA-901, or fragments or analogs thereof.

14. The method of claim 11, wherein the glycoliposome is administered intravenously, intranasally, sublingually, orally, by inhalation, topically, intrathecally, or via transdermal administration.

15. The method of claim 11, wherein the method is for the treatment of a CNS-related disease or disorder.

16. The method of claim 11, wherein the method is for the treatment of a neurodegenerative disease or disorder, depression, post-traumatic stress disorder, stress, anxiety, addiction, drug abuse or addiction, pain, eating disorder, psychiatric or mood disorders, psychosis, or schizophrenia.

17. A process for preparing a synthetic glycolipid having the following formula (I)

(I)

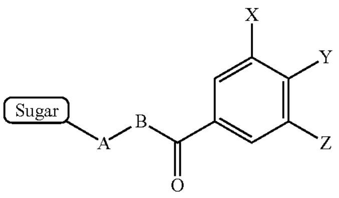

wherein

A represents $(CH_2)$ n with n being an integer from 2 to 10 or $CH_2$—$CH_2$—[O—$CH_2$—$CH_2$]$_m$ with m being an integer from 1 to 5;

B represents NH;

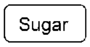 represents

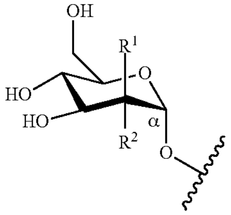

or

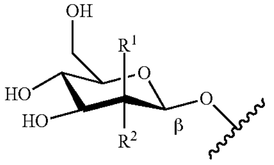

where $R^1$ represents OH and $R^2$ represents H, or where $R^1$ represents H and $R^2$ represents OH;

Y represents H when X and Z which are identical represent O—$(CH_2)_p$—$CH_3$, or X represents H when Y and Z which are identical represent O—$(CH_2)$ p-$CH_3$, with p being an integer from 5 to 18;

the process comprising:

reducing a compound of formula (V)

(V)

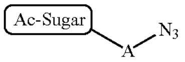

where 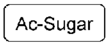 represents

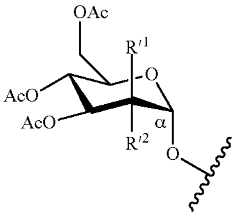

or

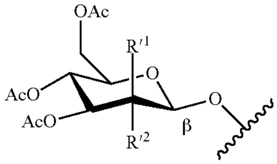

, $R'^1$ represents OAc and $R'^2$ represents H, or where $R'^1$ represents H and $R'^2$ represents OAc;

into the corresponding amine; and coupling the amine with a compound of formula (VI)

(VI)

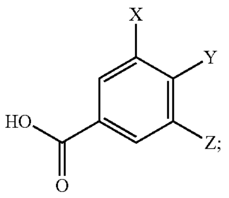

thereby forming the compound of formula ($I_{Ac}$)

($I_{Ac}$)

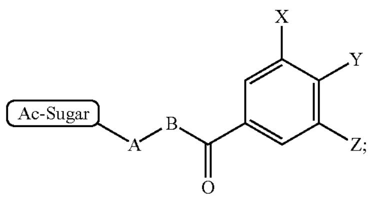

and converting the compound of formula ($I_{Ac}$) into the synthetic glycolipid of formula (I).

18. The process of claim 17, wherein the step of reducing and coupling are performed as a one-pot synthesis.

19. The process of claim 17, wherein the reducing is performed by reacting a solution of the compound of formula (V) with a phosphine to form a first mixture comprising the amine, then the compound of formula (VI) is added to the first mixture and reacted with the amine in the presence of a coupling agent, to form a second mixture comprising the compound of formula ($I_{Ac}$).

20. The process of claim 17, wherein the reducing is performed by reacting a solution comprising the compound of formula (V) and formula (VI) with a phosphine to form a first mixture comprising the amine and the compound of formula (VI), and the coupling is performed by adding a coupling agent to then obtain a second mixture comprising the compound of formula ($I_{Ac}$).

* * * * *